US012668604B2

(12) United States Patent
Zhang et al.

(10) Patent No.: US 12,668,604 B2
(45) Date of Patent: Jun. 30, 2026

(54) HETEROARYL COMPOUNDS AS INHIBITORS OF RIP2 KINASE, COMPOSITION AND APPLICATION THEREOF

(71) Applicants: Accro Bioscience (HK) Limited, Wan Chai (HK); Xiaohu Zhang, Suzhou (CN)

(72) Inventors: Xiaohu Zhang, Suzhou (CN); Sudan He, Suzhou (CN)

(73) Assignee: Accro Bioscience (HK) Limited, Hong Kong (CN)

( * ) Notice: Subject to any disclaimer, the term of this patent is extended or adjusted under 35 U.S.C. 154(b) by 387 days.

(21) Appl. No.: 18/281,600

(22) PCT Filed: Mar. 12, 2022

(86) PCT No.: PCT/US2022/020082
§ 371 (c)(1),
(2) Date: Sep. 12, 2023

(87) PCT Pub. No.: WO2022/192760
PCT Pub. Date: Sep. 15, 2022

(65) Prior Publication Data

US 2024/0190904 A1 Jun. 13, 2024

(30) Foreign Application Priority Data

Mar. 12, 2021 (CN) ......................... 202110272207.4
Dec. 2, 2021 (CN) ......................... 202111460309.5

(51) Int. Cl.
*C07F 9/53* (2006.01)
*A61K 31/675* (2006.01)

(52) U.S. Cl.
CPC .......... *C07F 9/5325* (2013.01); *A61K 31/675* (2013.01)

(58) Field of Classification Search
CPC ..................................................... C07F 9/5325
See application file for complete search history.

(56) References Cited

U.S. PATENT DOCUMENTS

2012/0041024 A1 2/2012 Charnley et al.
2017/0128437 A1 5/2017 Bury et al.

FOREIGN PATENT DOCUMENTS

CN 114014890 A 2/2022
WO 2006034491 A2 3/2006

OTHER PUBLICATIONS

International Search Report for PCT/US2022/020082.

*Primary Examiner* — Yong S. Chong

(57) ABSTRACT

The present disclosure provides heterocycle compounds with RIP2 kinase inhibitory activity, pharmaceutical compositions comprising the same, methods using the same and applications thereof. The present disclosure provides compounds of Formula (I), as inhibitors of RIP2 kinase. These compounds can be used for preventing and/or treating RIP2 kinase-related diseases and/or conditions.

(I)

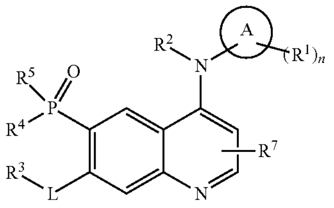

18 Claims, 4 Drawing Sheets

| CYP | Probe Substrate | Stock Conc. | Final Conc.(µM) | Selective Inhibitors | Stock Conc. | Final Conc. (µM) | Microsomes Conc. (mg/mL) | Incubation time (min) | Prepare 4 × substrate |
|---|---|---|---|---|---|---|---|---|---|
| 1A2 | Phenacetin | 6 mM in ACN | 30 | α-Naphthoflavon | 0.3 mM in DMSO | 0.3 | 0.1 | 10 | 120 µM in in K-buffer: 40 µL substrate stock + 1960 µL K-buffer |
| 2C9 | Diclofenac | 10 mM in $H_2O$ | 10 | Sulfaphenazole | 10 mM in DMSO | 10 | 0.1 | 10 | 40 µM in K-buffer: 8 µL substrate stock + 1992 µL K-buffer |
| 2C19 | S-Mephenytoin | 35 mM in ACN | 35 | Omeprazole | 100 mM in DMSO | 100 | 0.5 | 45 | 140 µM in 1.6 mg/ml HLM 8 µL substrate stock + 160 µL microsome stock + 1832 µL K-buffer |
| 2D6 | Bufuralol | 10 mM in $H_2O$ | 10 | Quinidine | 2.5 mM in DMSO | 2.5 | 0.1 | 10 | 40 µM in K-buffer 8 µL substrate stock + 1992 µL K-buffer |
| 3A4 | Testosterone | 10 mM in ACN | 80 | Ketoconazole | 2.5 mM in DMSO | 2.5 | 0.1 | 5 | 320 µM in K-buffer: 64 µL substrate stock + 1936 µL K-buffer |
| | Midazolam | 1 mM in ACN | 5 | | | | | | 20 µM in K-buffer: 40 µL substrate + 1960 µL K-buffer |

FIG. 4

| Compound | | Stock Solution (in DMSO) | | apical Buffer | basolateral buffer | Final DMSO concentration |
|---|---|---|---|---|---|---|
| | | Test cmpd | Verapamil | | | |
| Erythromycin+ Metoprolol+ Atenolol | A-to-B dosing solution | 10 mM 3 μL | -- | 0.1% DMSO HBSS + LY 3 mL | - | 0.4% |
| | A-to-B Receiver solution | -- | -- | -- | 0.4% DMSO HBSS 3 mL | 0.4% |
| | B-to-A dosing solution | 10 mM 3 μL | -- | -- | 0.1% DMSO HBSS 3 mL | 0.4% |
| | B-to-A Receiver solution | -- | -- | 0.4% DMSO HBSS+LY 3 mL | -- | 0.4% |
| compounds | A-to-B dosing solution | 10 mM 3 μL | -- | 0.3% DMSO HBSS + LY 3 mL | -- | 0.4% |
| | A-to-B Receiver solution | -- | -- | -- | 0.4% DMSO HBSS 3 mL | 0.4% |
| | B-to-A dosing solution | 10 mM 3 μL | -- | -- | 0.3% DMSO HBSS 3 mL | 0.4% |
| | B-to-A Receiver solution | -- | -- | 0.4% DMSO HBSS+LY 3 mL | -- | 0.4% |

FIG. 5

HETEROARYL COMPOUNDS AS INHIBITORS OF RIP2 KINASE, COMPOSITION AND APPLICATION THEREOF

CROSS REFERENCE TO RELATED APPLICATIONS

This application claims the benefit of Chinese Patent Applications 202110272207.4, filed on Mar. 12, 2021; and 202111460309.5, filed on Dec. 2, 2021; all of which are hereby incorporated by reference in their entirety.

FIELD OF INVENTION

The present invention is in the medical technology field, and generally relates to heteroaryl compounds and, more particularly, relates to novel aminoquinolin compounds that are inhibitors of nucleotide-binding oligomerization domain (NOD)/receptor-interacting protein 2 (RIP2) pathways. The present invention also relates to compositions comprising the aminoquinolin compounds, their method of making, and their applications in therapies targeting the prevention and/or treatment of diseases associated with RIP2 receptor inhibition, including receptor-interacting protein kinase-2 (RIP2) related diseases, including tumors, autoimmune diseases, neurodegenerative diseases, metabolic diseases, and genetic diseases.

BACKGROUND OF THE INVENTION

NOD-like receptors (NLRs) such as NOD1 and NOD2 (i.e., nucleotide-binding oligomerization domain-containing proteins 1 and 2) are pattern recognition receptors (PRRs). Activation of either NOD1 or NOD2 may lead to cellular cascades response (Cell. Signal. 18 (2006) 2223-2229).

NOD2-mediated signaling relies on receptor-interacting protein kinase 2 (RIP2). For example, normally, the leucine-rich repeat (LPR) domain of NOD2 folds and enter the intermediate domain, thereby becoming self-inhibitory. However, when LPR is recognized and bound by its substrate muramyl dipeptide (MDP), NOD2 changes its conformation and self-activates (Science 300 (2003) 1584-1587; J. Biol. Chem. 278 (2003) 5509-5512), thereby recruiting and activating downstream RIP2 through CARD-CRAD (i.e., caspase activation and recruitment domain) interaction between NOD2 and RIP2. RIP2 then undergoes autophosphorylation and is ubiquitinated by a series of E3 ubiquitin ligases, including X chromosome-linked inhibitor of apoptosis protein (XIAP) and cellular inhibitor of apoptosis protein 1 (cIAP1). Polyubiquitinated RIP2 oligomerizes to promote polyubiquitination of NF-κB essential modulator (NEMO, also known as inhibitor of nuclear factor kappa-B kinase subunit gamma (IKK-γ)) and activation of transforming growth factor-β-activated kinase 1 (TAK1), subsequently regulates the recruitment of TAK1 adaptor proteins TAB1 and TAB2/3 and leads to the activation of mitogen-activated protein kinases (MAPK) signaling pathway (extracellular signal-regulated kinase (ERK), p38, c-Jun N-terminal kinase (JNK)) and the activation of nuclear factor kappa B (NF-κB). For example, the TAB protein of the TAK1/TAB2/TAB3 complex binds the lysine-63 (K63)-linked polyubiquitin chain, allowing TAK1 to phosphorylate and activate the IKK complex. The activation of IKK complex promotes the phosphorylation of inhibitor of κB molecules alpha (IκBα), thereby leading to the dissociation of IκB and the activation of the NF-κB pathway. The activated heterodimeric p65/p50 then translocates to the nucleus and activates transcription of genes involved in immune responses, cell death pathways and growth control (Clinical Immunology (2021), 223, 108648).

Receptor-interacting protein kinase 2 (RIP2, also known as RIPk2, RICK, CARDIAK or CARD3) is a member of the receptor interacting serine/threonine protein kinase family involved in innate immune signaling, encoded by the RIP2 gene located on human chromosome 8. The 61 kDA encoded protein possesses a C-terminal casepase recruitment domain (CARD), an N-terminal kinase domain and a bridging intermediate domain (Curr. Biol. 8 (1998) 885-888).

RIP2 plays an important role in the immune system and is regulated by the intracellular peptidoglycan sensors NOD1 and NOD2 (J. Immunol. 178 (2007) 2380-2386), eliciting innate immune responses against bacteria and infections. Initial studies suggested that the kinase activity of RIP2 is unnecessary for the activation of the NF-kB pathway and the production of cytokines. However, transgenic mice lacking RIP2 protein are defective in their response to NOD1 or NOD2 agonists, highlighting the important role of RIP2 kinase places in NOD1 and NOD2 (J. Immunol. 2007, 178 (4), 2380-2386). Once RIP2 is activated, serine 176 and tyrosine 474 will be autophosphorylated. The phosphorylation of serine 176 is necessary for RIP2 activation. However, the phosphorylation of tyrosine 474 increases RIP2 activity but is not required for signaling (Genes Dev. 24 (2010), 2666-2677).

Dysregulation of NOD/RIP2-dependent signaling pathways has been implicated in numerous human diseases, including asthma, early-onset inflammatory bowel disease, sarcoidosis, Crohn's disease, multiple sclerosis, and Blau syndrome (an ultra-high autoinflammatory disease) etc. RIP2 is upregulated in pathological conditions such as sepsis and Alzheimer's disease. Furthermore, RIP2 can act a prognostic marker in different cancer types, such as, for example, inflammatory breast cancer (a rare and aggressive form of breast cancer that is associated with high mortality). RIP2 is overexpressed in patients with inflammatory breast cancer. See EMBO Mol. Med. 5 (2013) 1278-1295; Arthritis Rheum. 43 (2013) 125-130; Pediatr. Rheumatol. Online J. 12 (2014) 33; Scientific World Journal 2016 (2016) 2597376; J. Leukoc. Biol. 94 (2013) 927-932; Biochem. Biophys. Res. Commun. 281 (2001) 84-93; Cancers (Basel) 10 (2018).

Since the inhibition of RIP2 kinase activity may abrogate NOD1/2 downstream signaling, the development of small molecule inhibitors that inhibit RIP2 kinase activity is expected to delay the progression of the disease state or pathological conditions caused by the activation of NF-κB or MAPK pathways, thereby resulting in preventive and/or therapeutic effects and promising clinical application.

SUMMARY OF THE INVENTION

The present disclosure provides quinoline derivatives as inhibitors of NOD/RIP2 pathway, and compositions and applications thereof. These disclosed quinoline derivatives, and compositions and applications thereof, may effectively prevent or treat diseases and disorders responsive to RIP receptor inhibition, including, for example, tumors, autoimmune diseases, neurodegenerative diseases, metabolic diseases, and genetic diseases.

The goal of the present disclosure is to provide RIP2 inhibitors, and compositions and applications thereof An aspect of the present disclosure provides a compound of Formula (I):

(I)

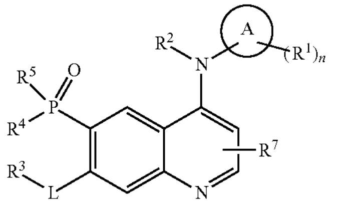

or a pharmaceutically acceptable salt, ester, solvate, prodrug, isotope-labeled derivative, stereoisomer or tautomer thereof, wherein:

n is 0, 1, 2 or 3;

L is a bond, —O—, —N($R^6$)—, or

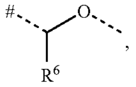

wherein # denotes a connection to $R^3$;

ring A is $C_{6-10}$ aryl and 5-10 membered heteroaryl;

$R^1$ is independently H, deuterium, halide, —OH, amino, —CN, $C_{1-6}$ alkyl, $C_{3-6}$ cycloalkyl, —O($C_{1-6}$ alkyl), —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{2-6}$ alkenyl and $C_{2-6}$ alkynyl are unsubstituted or substituted with 1 to 3 groups independently selected from $R^a$;

$R^2$ is independently H, deuterium, $C_{1-3}$ alkyl or $C_{3-6}$ cycloalkyl, wherein $C_{1-3}$ alkyl and $C_{3-6}$ cycloalkyl are unsubstituted or substituted with 1 to 3 groups independently selected from $R^b$;

$R^3$ is independently H, halide, —OH, amino, $C_{1-6}$ alkyl, $C_{3-6}$ cycloalkyl, —O($C_{1-6}$ alkyl), 3-6 membered cycloheteroalkyl, $C_{6-10}$ aryl or 5-10 membered heteroaryl, wherein $C_{1-6}$ alkyl, $C_{3-6}$ cycloalkyl, 3-6 membered cycloheteroalkyl, $C_{6-10}$ aryl and 5-10 membered heteroaryl are unsubstituted or substituted with 1 to 3 groups independently selected from $R^c$;

$R^4$ is $C_{1-3}$ alkyl, wherein $C_{1-3}$ alkyl is unsubstituted or substituted with 1 to 3 groups independently selected from $R^d$;

$R^5$ is $C_{1-3}$ alkyl, wherein $C_{1-3}$ alkyl is unsubstituted or substituted with 1 to 3 groups independently selected from $R^e$;

or $R^4$ and $R^5$ together with the phosphorus atom attached thereto form 5-6 membered cycloheteroalkyl or 5-8 members cycloheteroalkenyl, wherein 5-6 membered cycloheteroalkyl and 5-8 members cycloheteroalkenyl are unsubstituted or substituted with 1 to 3 groups independently selected from $R^d$;

$R^6$ is H, $C_{1-3}$ alkyl, or $C_{3-6}$ cycloalkyl, wherein $C_{1-3}$ alkyl and $C_{3-6}$ cycloalkyl are unsubstituted or substituted with 1 to 3 groups independently selected from $R^f$;

$R^7$ is independently H, deuterium, F, Cl, Br, —OH, amino, —CN, $C_{1-6}$ alkyl, $C_{3-6}$ cycloalkyl, —O($C_{1-6}$ alkyl), —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{2-6}$ alkenyl and $C_{2-6}$ alkynyl are unsubstituted or substituted with 1 to 3 groups independently selected from $R^a$;

$R^a$, $R^b$, $R^d$, $R^e$ and $R^f$ are independently F, Cl, Br, I, —OH, amino, methyl or methoxy; and $R^c$ is independently deuterium, F, Cl, Br, I, —OH, amino, methyl, methoxy or

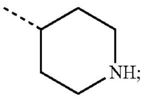

wherein each of 3-6 membered cycloheteroalkyl 5-6 membered cycloheteroalkyl, 5-8 members cycloheteroalkenyl, and 5-10 member heteroaryl comprises 1 to 3 heteroatoms or heteroatom groups independently selected from N, NH, O, S and P(═O).

In some embodiments of aspects provided herein, $R^2$ is H.

In some embodiments, L is a bond, O, or

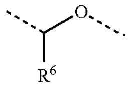

In some embodiments,

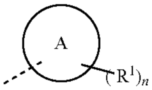

is selected from the group consisting of:

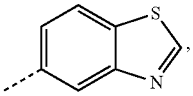,
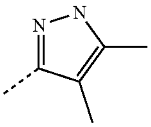,
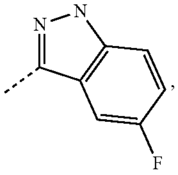,
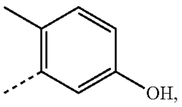
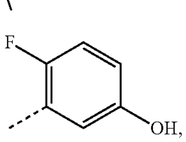
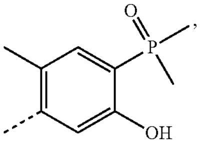, and
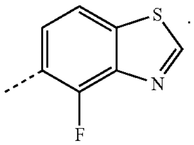.

In some embodiments,

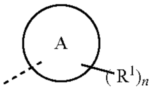

is selected from the group consisting of:

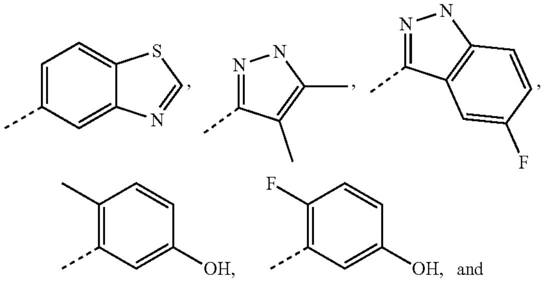

and

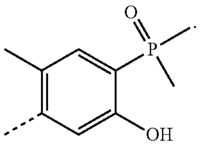

In some embodiments,

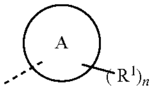

is selected from the group consisting of:

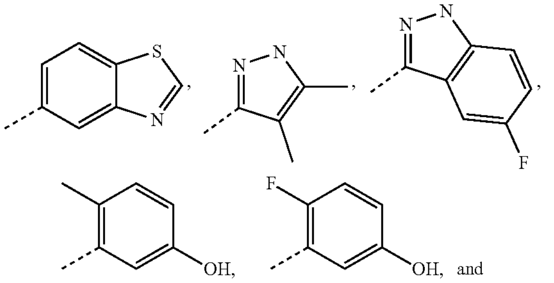

and

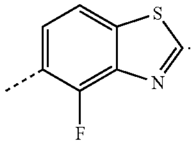

In some embodiments,

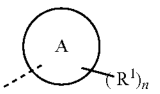

is

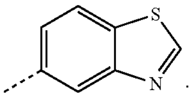

.

In some embodiments, $R^3$ is independently H, halide, —OH, amino, $C_{1-6}$ alkyl, $C_{3-6}$ cycloalkyl, —O($C_{1-6}$ alkyl), 3-6 membered cycloheteroalkyl, and 5-10 membered heteroaryl, wherein $C_{1-6}$ alkyl, $C_{3-6}$ cycloalkyl, 3-6 membered cycloheteroalkyl, or 5-10 membered heteroaryl are unsubstituted or substituted with 1 to 3 groups independently selected from $R^c$.

In some embodiments, $R^3$ is independently H, F, methyl, ethyl, n-propyl, i-propyl, methoxy, —$OCD_3$, —$OCF_3$, —$OCHF_2$, —$OCH_2CH_2OH$, —$OCH_2CH_2OCH_3$,

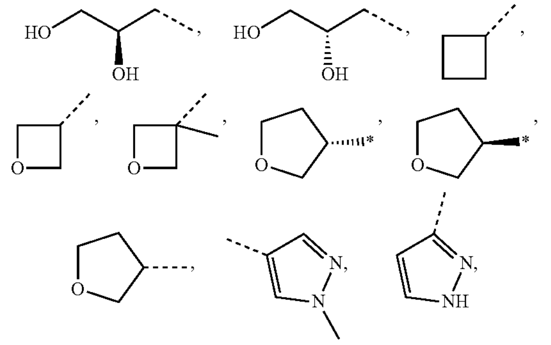

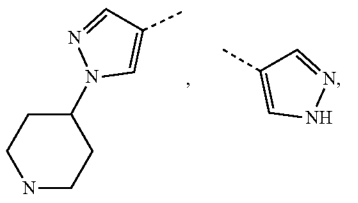

or

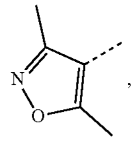

, wherein * denotes a connection to L.

In some embodiments, $R^3$ is independently H, methyl, ethyl, n-propyl, i-propyl, methoxy, —$OCH_2CH_2OH$, —$OCH_2CH_2OCH_3$,

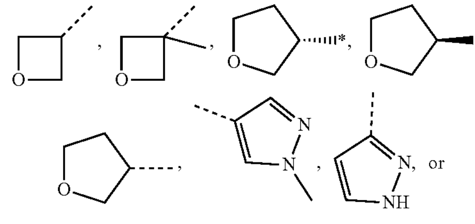

or

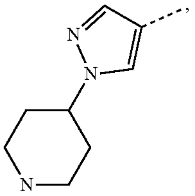

wherein * denotes a connection to L.

In some embodiments, $R^3$ is independently H, F, methyl, methoxy, —$OCD_3$, —$OCF_3$, —$OCHF_2$, —$OCH_2CH_2OH$, —$OCH_2CH_2OCH_3$,

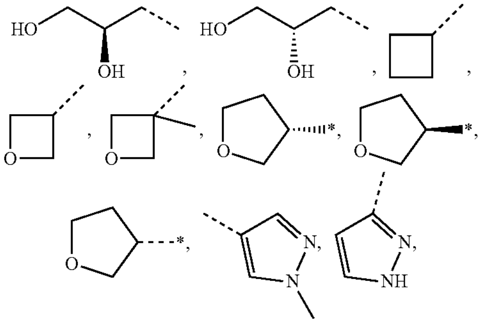

-continued

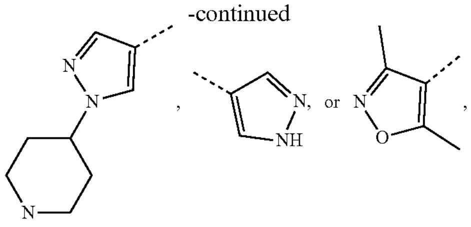

wherein * denotes a connection to L.

In some embodiments, $R^3$ is independently F, methoxy, $—OCD_3$, $—OCF_3$, $—OCHF_2$, $—OCH_2CH_2OH$, $—OCH_2CH_2OCH_3$,

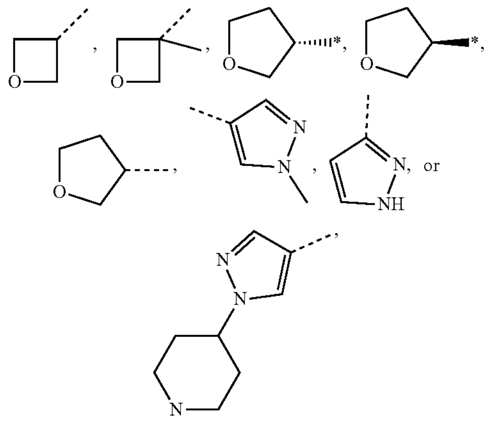

wherein * denotes a connection to L.

In some embodiments, $R^3$ is independently methoxy, $—OCD_3$, $—OCF_3$, and $—OCHF_2$, wherein * denotes a connection to L.

In some embodiments, $R^3$-L is independently H, F, methyl, ethyl, n-propyl, i-propyl, methoxy, $—OCD_3$, $—OCF_3$, $—OCHF_2$, $—OCH_2CH_2OH$, $—OCH_2CH_2OCH_3$,

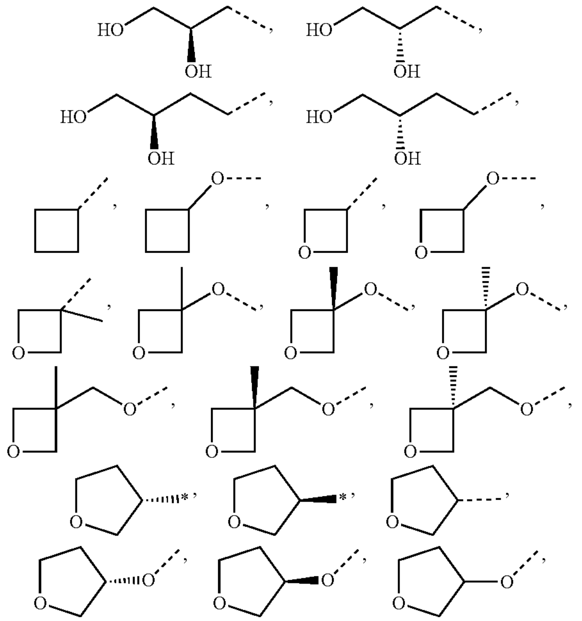

-continued

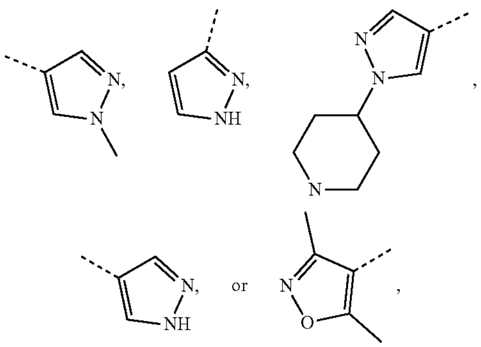

wherein * denotes a connection to quinoline.

In some embodiments, $R^4$ is methyl; $R^5$ is methyl; and $R^6$ is H or $C_{1-3}$ alkyl. In some embodiments, $R^4$ is methyl; $R^5$ is methyl; and $R^6$ is H. In some embodiments, $R^7$ is H, deuterium, F, Cl or Br. In some embodiments, $R^7$ is H or F.

In some embodiments, the compound of Formula (I) is selected from the group consisting of:

A1

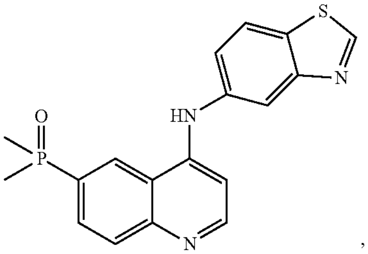

,

A2

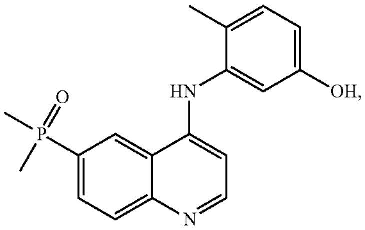

A3

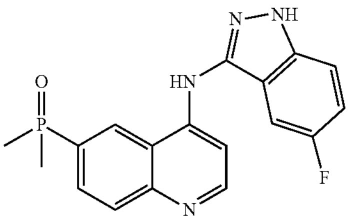

,

A4

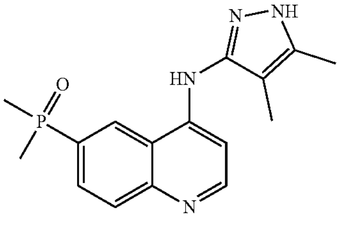

,

-continued
A5
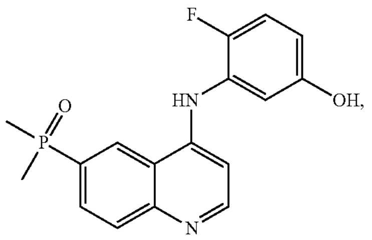
A6
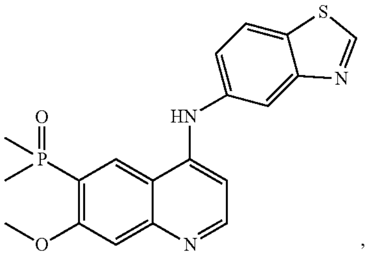
,
A7
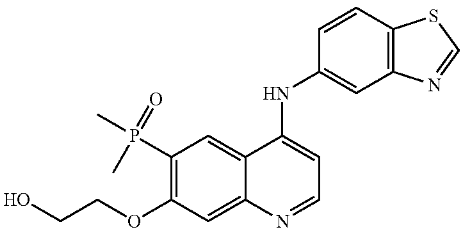
,
A8
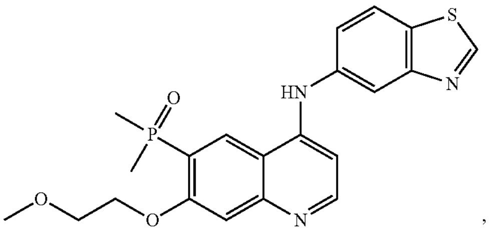
,
A9
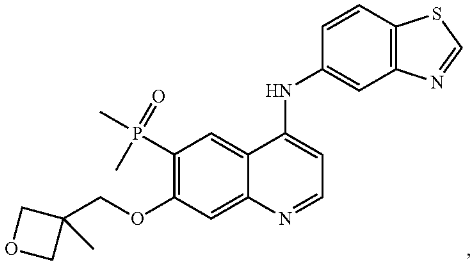
,
A10
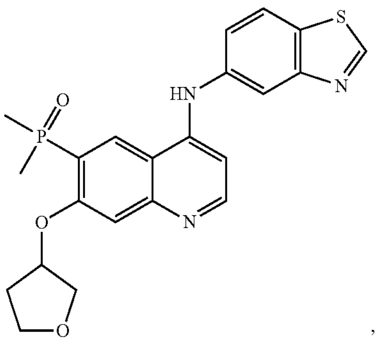
,
-continued
A11
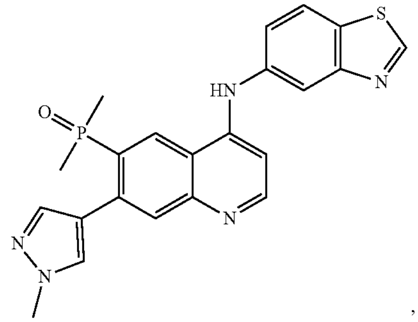
,
A12
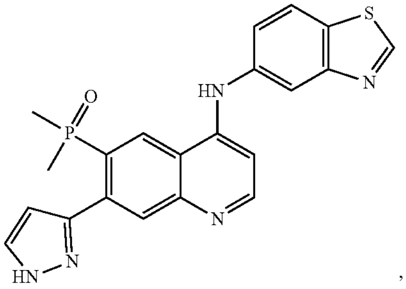
,
A13
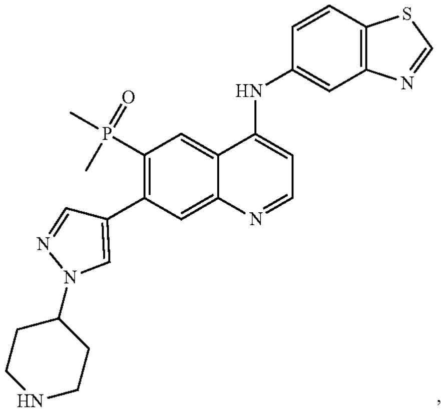
,
A14
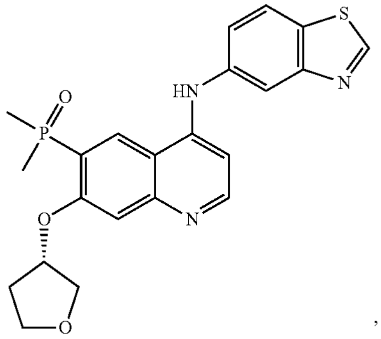
, -continued
A15
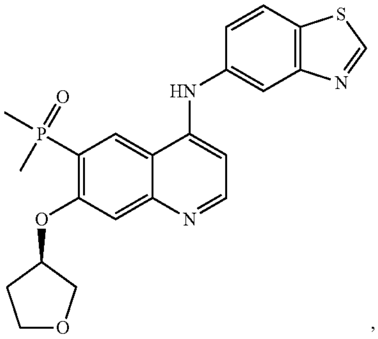
,
A16
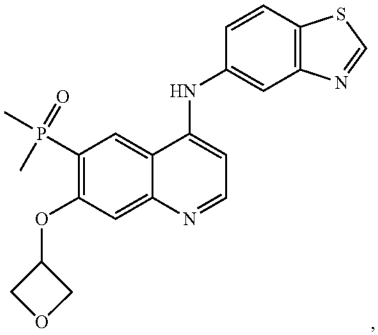
,
A17
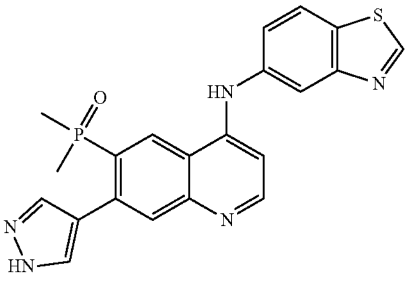
,
A18
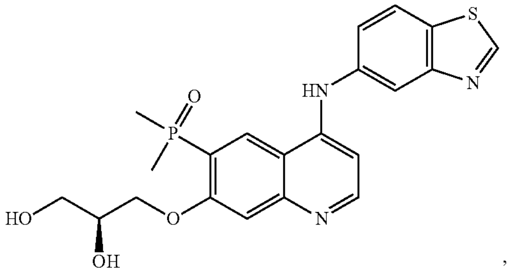
,
A19
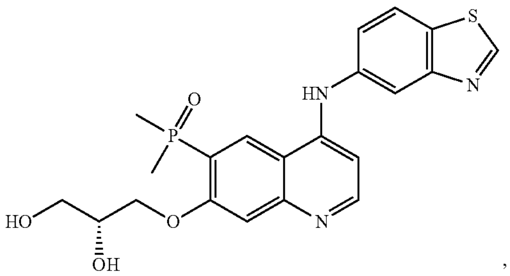
,
-continued
A20
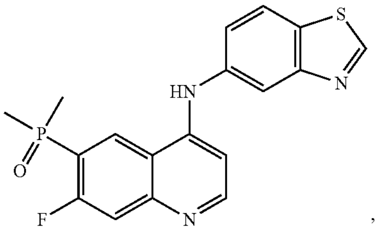
,
A21
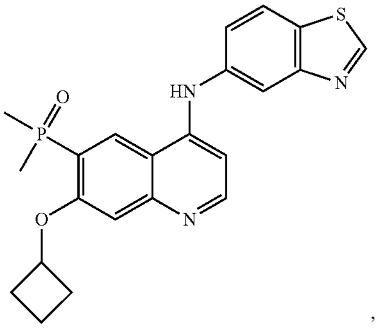
,
A22
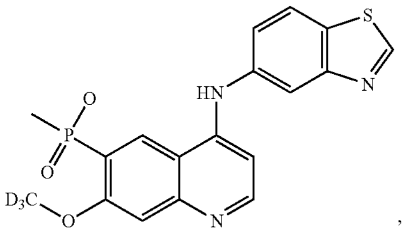
,
A23
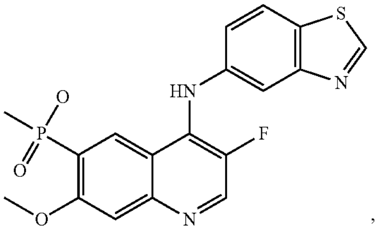
,
A24
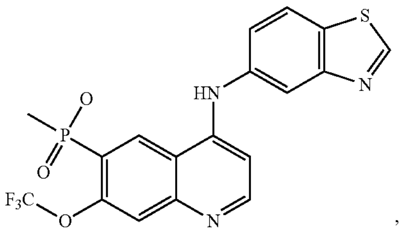
,
A25
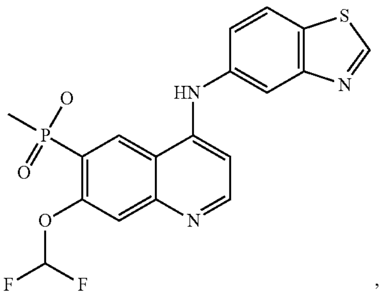
, -continued

A26

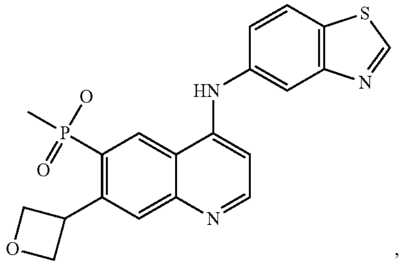

,

A27

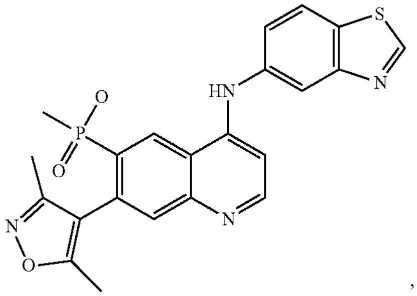

,

A28

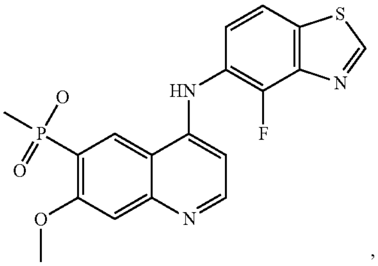

, and

A29

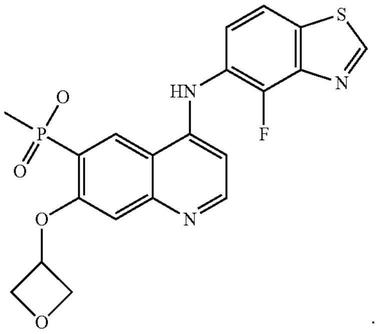

.

In some embodiments, the present disclosure provides a pharmaceutical composition comprising a therapeutically effective amount of a compound disclosed herein or a pharmaceutically acceptable salt, ester, solvate, prodrug, isotope-labeled derivative, stereoisomer or tautomer thereof, and a pharmaceutically acceptable carrier.

In some embodiments, the present disclosure provides a pharmaceutical formulation comprising a compound disclosed herein or a pharmaceutically acceptable salt, ester, solvate, prodrug, isotope-labeled derivative, stereoisomer or tautomer thereof or the pharmaceutical composition disclosed herein, wherein the pharmaceutical formulation is tablet, capsule, injection, granule, powder, suppository, pill, gel, dispersion, oral solution, inhalant, suspension, or solid suspension.

In some embodiments, the present disclosure provides a composition comprising:

(i) a compound disclosed herein or a pharmaceutically acceptable salt, ester, solvate, prodrug, isotope-labeled derivative, stereoisomer or tautomer thereof or the pharmaceutical composition disclosed herein; and (ii) at least one additional therapeutic agent selected from the group consisting of anti-tumor agent, agent treating autoimmune disease, anti-neurodegenerative agent, agent treating metabolic disease, and agent treating genetic disease.

In some embodiments, the present disclosure provides a method for treating a disease or disorder associated with RIP2 receptor in a mammal suffering therefrom, comprising administering to the mammal a therapeutically effective amount of a compound disclosed herein or a pharmaceutically acceptable salt, ester, solvate, prodrug, isotope-labeled derivative, stereoisomer or tautomer thereof, or a pharmaceutical composition disclosed herein, or a composition disclosed herein, wherein the disease or disorder associated with RIP2 receptor is systematic inflammatory response, autoimmune diseases, tumor, cancer, metabolic diseases or neurodegenerative diseases.

In some embodiments, the present disclosure provides a method for treating a disease or disorder associated with RIP2 receptor in a mammal suffering therefrom, comprising administering to the mammal a therapeutically effective amount of a compound disclosed herein or a pharmaceutically acceptable salt, ester, solvate, prodrug, isotope-labeled derivative, stereoisomer or tautomer thereof, or a pharmaceutical composition disclosed herein, or a composition disclosed herein, wherein the disease or disorder associated with RIP2 receptor is uveitis, dermatitis, acute lung injury, type 2 diabetes mellitus, arthritis, ulcerative colitis, Crohn's disease, early-onset inflammatory bowel disease, extraintestinal inflammatory bowel disease, prevention of ischemia reperfusion injury in solid organ transplant, non-alcohol steatohepatitis, autoimmune hepatitis, asthma, systemic lupus erythematosus, sarcoidosis, Wegener's granulomatosis, interstitial lung disease, pulmonary fibrosis, renal fibrosis, liver fibrosis, myocardial infarction, hypersensitivity pneumonitis, ankylosing spondylitis, multiple sclerosis, systemic sclerosis, polymyositis, rheumatoid arthritis, myasthenia gravis, type 1 diabetes, glomerulonephritis, autoimmune thyroiditis, graft rejection, Crohn's disease, Blau syndrome, scleroderma, psoriasis, stomatitis, retinitis pigmentosa, proliferative vitreoretinopathy, Best vitelliform macular dystrophy, eczema, urticaria, vasculitis, eosinophilic fasciitis, wet age-related macular degeneration, dry age-related macular degeneration, diabetic retinopathy, retinopathy of prematurity (ROP), diabetic macular edema, uveitis, retinal vein occlusion, cystoid macular edema, glaucoma, Parkinson's disease, Alzheimer's disease, Huntington's disease, breast cancer, lung cancer, bladder cancer, pancreatic cancer, liver cancer, head and neck squamous cellcarcinoma, thyroid cancer, sarcoma, osteosarcoma, desmoid tumor, melanoma, prostate cancer, colorectal cancer, ovarian cancer, cervical cancer, esophageal cancer, gastric cancer, myeloma, lymphoma, mantle cell lymphoma, cutaneous T-cell lymphoma, chronic and non-progressive anemia, primary or essential thrombocythemia, leukemia, acute leukemia, chronic leukemia, lymphocytic leukemia, myeloid leukemia, myelodysplastic syndrome, myeloproliferative disorder, brain tumor, astrocytoma, medulloblastoma, Schwannomor, primitive neuroectodermal tumor, or pituitary tumor.

In some embodiments, the compound disclosed herein or a pharmaceutically acceptable salt, ester, solvate, prodrug, isotope-labeled derivative, stereoisomer or tautomer thereof, or a pharmaceutical composition disclosed herein, or a composition disclosed herein for is for use in a method of treating the human or animal body by therapy. In some embodiments, the compound disclosed herein or a pharmaceutically acceptable salt, ester, solvate, prodrug, isotope-labeled derivative, stereoisomer or tautomer thereof, or a pharmaceutical composition disclosed herein, or a composition disclosed herein is for use as a medicament. In some embodiments, the compound disclosed herein or a pharmaceutically acceptable salt, ester, solvate, prodrug, isotope-labeled derivative, stereoisomer or tautomer thereof, or a pharmaceutical composition disclosed herein, or a composition disclosed herein is for use in the treatment of a disease or disorder associated with RIP2 receptor. The disease or disorder associated with RIP2 receptor is systematic inflammatory response, autoimmune diseases, tumor, cancer, metabolic diseases or neurodegenerative diseases. In some embodiments, the disease or disorder associated with RIP2 receptor is uveitis, dermatitis, acute lung injury, type 2 diabetes mellitus, arthritis, ulcerative colitis, Crohn's disease, early-onset inflammatory bowel disease, extraintestinal inflammatory bowel disease, prevention of ischemia reperfusion injury in solid organ transplant, non-alcohol steatohepatitis, autoimmune hepatitis, asthma, systemic lupus erythematosus, sarcoidosis, Wegener's granulomatosis, interstitial lung disease, pulmonary fibrosis, renal fibrosis, liver fibrosis, myocardial infarction, hypersensitivity pneumonitis, ankylosing spondylitis, multiple sclerosis, systemic sclerosis, polymyositis, rheumatoid arthritis, myasthenia gravis, type 1 diabetes, glomerulonephritis, autoimmune thyroiditis, graft rejection, Crohn's disease, Blau syndrome, scleroderma, psoriasis, stomatitis, retinitis pigmentosa, proliferative vitreoretinopathy, Best vitelliform macular dystrophy, eczema, urticaria, vasculitis, eosinophilic fasciitis, wet age-related macular degeneration, dry age-related macular degeneration, diabetic retinopathy, retinopathy of prematurity (ROP), diabetic macular edema, uveitis, retinal vein occlusion, cystoid macular edema, glaucoma, Parkinson's disease, Alzheimer's disease, Huntington's disease, breast cancer, lung cancer, bladder cancer, pancreatic cancer, liver cancer, head and neck squamous cellcarcinoma, thyroid cancer, sarcoma, osteosarcoma, desmoid tumor, melanoma, prostate cancer, colorectal cancer, ovarian cancer, cervical cancer, esophageal cancer, gastric cancer, myeloma, lymphoma, mantle cell lymphoma, cutaneous T-cell lymphoma, chronic and non-progressive anemia, primary or essential thrombocythemia, leukemia, acute leukemia, chronic leukemia, lymphocytic leukemia, myeloid leukemia, myelodysplastic syndrome, myeloproliferative disorder, brain tumor, astrocytoma, medulloblastoma, Schwannomor, primitive neuroectodermal tumor, or pituitary tumor.

In some embodiments,

In some embodiments, the compound has Formula (II):

(II)

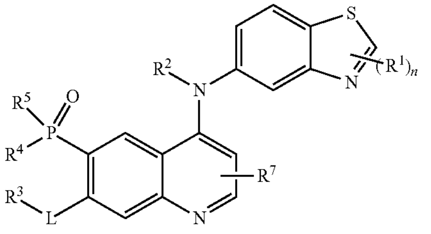

or a pharmaceutically acceptable salt, ester, solvate, prodrug, isotope-labeled derivative, stereoisomer or tautomer thereof, wherein:

n is 0, 1, 2 or 3;

L is a bond, —O—, —N($R^6$)—, or

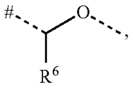

wherein # denotes a connection to $R^3$;

$R^1$ is independently H, deuterium, halide, —OH, amino, —CN, $C_{1-6}$ alkyl, $C_{3-6}$ cycloalkyl, —O($C_{1-6}$ alkyl), —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{2-6}$ alkenyl and $C_{2-6}$ alkynyl are unsubstituted or substituted with 1 to 3 groups independently selected from $R^a$;

$R^2$ is independently H, deuterium, $C_{1-3}$ alkyl or $C_{3-6}$ cycloalkyl, wherein $C_{1-3}$ alkyl and $C_{3-6}$ cycloalkyl are unsubstituted or substituted with 1 to 3 groups independently selected from $R^b$;

$R^3$ is independently H, halide, —OH, amino, $C_{1-6}$ alkyl, $C_{3-6}$ cycloalkyl, —O($C_{1-6}$ alkyl), 3-6 membered cycloheteroalkyl, $C_{6-10}$ aryl or 5-10 membered heteroaryl, wherein $C_{1-6}$ alkyl, $C_{3-6}$ cycloalkyl, 3-6 membered cycloheteroalkyl, $C_{6-10}$ aryl and 5-10 membered heteroaryl are unsubstituted or substituted with 1 to 3 groups independently selected from $R^c$;

$R^4$ is $C_{1-3}$ alkyl, wherein $C_{1-3}$ alkyl is unsubstituted or substituted with 1 to 3 groups independently selected from $R^d$;

$R^5$ is $C_{1-3}$ alkyl, wherein $C_{1-3}$ alkyl is unsubstituted or substituted with 1 to 3 groups independently selected from $R^e$;

or $R^4$ and $R^5$ together with the phosphorus atom attached thereto form 5-6 membered cycloheteroalkyl or 5-8 members cycloheteroalkenyl, wherein 5-6 membered cycloheteroalkyl and 5-8 members cycloheteroalkenyl are unsubstituted or substituted with 1 to 3 groups independently selected from $R^d$;

$R^6$ is H, $C_{1-3}$ alkyl, or $C_{3-6}$ cycloalkyl, wherein $C_{1-3}$ alkyl and $C_{3-6}$ cycloalkyl are unsubstituted or substituted with 1 to 3 groups independently selected from $R^f$;

$R^7$ is independently H, deuterium, F, Cl, Br, —OH, amino, —CN, $C_{1-6}$ alkyl, $C_{3-6}$ cycloalkyl, —O($C_{1-6}$ alkyl), —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{2-6}$ alkenyl and $C_{2-6}$ alkynyl are unsubstituted or substituted with 1 to 3 groups independently selected from $R^a$;

$R^a$, $R^b$, $R^d$, $R^e$ and $R^f$ are independently F, Cl, Br, I, —OH, amino, methyl or methoxy; and $R^c$ is independently deuterium, F, Cl, Br, I, —OH, amino, methyl, methoxy or

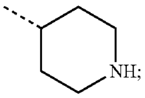

wherein each of 3-6 membered cycloheteroalkyl 5-6 membered cycloheteroalkyl, 5-8 members cycloheteroalkenyl, and 5-10 member heteroaryl comprises 1 to 3 heteroatoms or heteroatom groups independently selected from N, NH, O, S and P(=O).

In some embodiments, the compound has Formula (III):

(III)

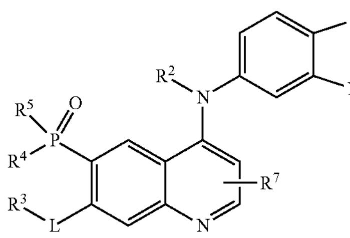

or a pharmaceutically acceptable salt, ester, solvate, prodrug, isotope-labeled derivative, stereoisomer or tautomer thereof, wherein:

L is a bond, —O—, —N($R^6$)—, or

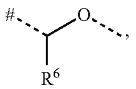

wherein # denotes a connection to $R^3$;

$R^2$ is independently H, deuterium, $C_{1-3}$ alkyl or $C_{3-6}$ cycloalkyl, wherein $C_{1-3}$ alkyl and $C_{3-6}$ cycloalkyl are unsubstituted or substituted with 1 to 3 groups independently selected from $R^b$;

$R^3$ is independently H, halide, —OH, amino, $C_{1-6}$ alkyl, $C_{3-6}$ cycloalkyl, —O($C_{1-6}$ alkyl), 3-6 membered cycloheteroalkyl, $C_{6-10}$ aryl or 5-10 membered heteroaryl, wherein $C_{1-6}$ alkyl, $C_{3-6}$ cycloalkyl, 3-6 membered cycloheteroalkyl, $C_{6-10}$ aryl and 5-10 membered heteroaryl are unsubstituted or substituted with 1 to 3 groups independently selected from $R^e$;

$R^4$ is $C_{1-3}$ alkyl, wherein $C_{1-3}$ alkyl is unsubstituted or substituted with 1 to 3 groups independently selected from $R^d$;

$R^5$ is $C_{1-3}$ alkyl, wherein $C_{1-3}$ alkyl is unsubstituted or substituted with 1 to 3 groups independently selected from $R^e$;

or $R^4$ and $R^5$ together with the phosphorus atom attached thereto form 5-6 membered cycloheteroalkyl or 5-8 members cycloheteroalkenyl, wherein 5-6 membered cycloheteroalkyl and 5-8 members cycloheteroalkenyl are unsubstituted or substituted with 1 to 3 groups independently selected from $R^d$;

$R^6$ is H, $C_{1-3}$ alkyl, or $C_{3-6}$ cycloalkyl, wherein $C_{1-3}$ alkyl and $C_{3-6}$ cycloalkyl are unsubstituted or substituted with 1 to 3 groups independently selected from $R^f$;

$R^7$ is independently H, deuterium, F, Cl, Br, —OH, amino, —CN, $C_{1-6}$ alkyl, $C_{3-6}$ cycloalkyl, —O($C_{1-6}$ alkyl), —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{2-6}$ alkenyl and $C_{2-6}$ alkynyl are unsubstituted or substituted with 1 to 3 groups independently selected from $R^a$;

$R^b$, $R^d$, $R^e$ and $R^f$ are independently F, Cl, Br, I, —OH, amino, methyl or methoxy; and $R^c$ is independently deuterium, F, Cl, Br, I, —OH, amino, methyl, methoxy or

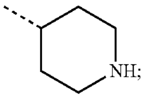

wherein each of 3-6 membered cycloheteroalkyl 5-6 membered cycloheteroalkyl, 5-8 members cycloheteroalkenyl, and 5-10 member heteroaryl comprises 1 to 3 heteroatoms or heteroatom groups independently selected from N, NH, O, S and P(=O).

The present disclosure also provides a formulation of the compound disclosed herein, the pharmaceutical composition disclosed herein, or the composition disclosed herein, wherein the formulation is tablet, capsule, injection agent, granule, powder, suppository, pill, gel, powder, oral solution, inhalation agent, suspension, or dry suspension.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

FIG. 4 depicts parameters of the system for Cytochrome P450 (CYP) inhibition in Example 14.

FIG. 5 depicts parameters to prepare the donor solutions in Example 15.

Figure 1:
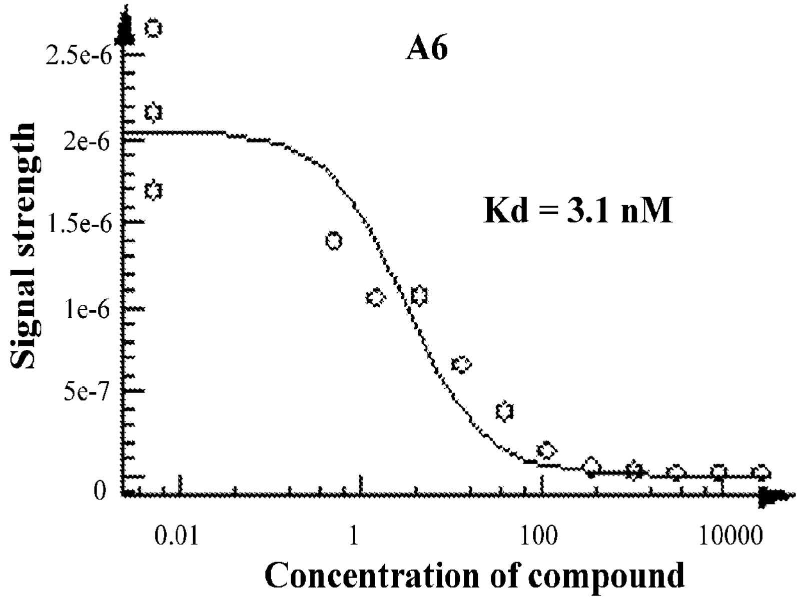
FIG. 1 depicts the experimental results of the binding affinity assay of compound A6 in Example 11.

Before proceeding with the detailed description, it is to be appreciated that the following detailed description is merely exemplary in nature and is not intended to limit the invention or the application and uses thereof. Hence, although the present disclosure is, for convenience of explanation, depicted and described as shown in certain illustrative embodiments, it will be appreciated that it can be implemented in various other types of embodiments and equivalents, and in various other systems and environments. Furthermore, there is no intention to be bound by any theory presented in the preceding background or the following detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Definitions

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms.

As used herein, the singular forms "a," "an" and "the" include plural referents unless the context clearly dictates otherwise. Thus, for example, reference to "a molecule" includes a plurality of such molecules, and the like.

The term "about" or "nearly" as used herein generally refers to within +/−15%, 10%, 9%, 8%, 7%, 6%, 5%, 4%, 3%, 2%, or 1% of the designated amount.

The term "halogen" or "halide" as used herein generally refers to fluorine, chlorine, bromine, and iodine. The term "haloalkyl" as used herein generally refers to an alkyl group that is substituted with one or more independently chosen halogens (e.g., "$C_1$-$C_6$ haloalkyl" groups have from 1 to 6 carbon atoms and at least one halogen). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl.

The term "alkyl" as used herein generally refers to a straight or branched chain saturated aliphatic hydrocarbon. Alkyl groups include groups having from 1 to 8 carbon atoms ($C_{1-8}$ alkyl), from 1 to 6 carbon atoms ($C_{1-6}$ alkyl) and from 1 to 4 carbon atoms ($C_1$-$C_4$ alkyl), including, for example, methyl, ethyl, propyl, isopropyl, n-butyl, sec-butyl, isobutyl, tert-butyl, pentyl, 2-pentyl, 3-pentyl, 2-methyl-2-butyl, 3-methyl-2-butyl, 3-methyl-1-butyl, 2-methyl-1-butyl, n-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl. Similarly, $C_{1-3}$ alkyl refers to an alkyl group having from 1 to 3 carbon atoms in a straight or branched chain, including, for example, methyl, ethyl, propyl, and isopropyl. In some instances, a substituent of an alkyl group is specifically indicated. For example, "cyanoalkyl" refers to an alkyl group substituted with at least one cyano substituent. In some embodiments, $C_{1-6}$ alkyl is, preferably, methyl, ethyl, n-propyl, isopropyl or tert-butyl.

The term "alkenyl" as used herein generally refers to straight or branched chain alkene groups, which comprise at least one unsaturated carbon-carbon double bond. Alkenyl groups include $C_{2-8}$ alkenyl, $C_{2-6}$ alkenyl and $C_{2-4}$ alkenyl groups, which have from 2 to 8, 2 to 6 or 2 to 4 carbon atoms, respectively, including, for example, ethenyl, allyl or isopropenyl. The term "alkynyl" as used herein generally refers to straight or branched chain alkyne groups, which have one or more unsaturated carbon-carbon bonds, at least one of which is a triple bond. Alkynyl groups include $C_{2-8}$ alkynyl, $C_{2-6}$ alkynyl and $C_{2-4}$ alkynyl groups, which have from 2 to 8, 2 to 6 or 2 to 4 carbon atoms, respectively.

The term "alkoxy" as used herein generally refers to an alkyl group as described above attached via an oxygen bridge to another chemical moiety. Alkoxy groups include different length of the alkyl groups, such as, for example, $C_{1-6}$ alkoxy and $C_{1-4}$ alkoxy groups, which have from 1 to 6 or from 1 to 4 carbon atoms, respectively. The term "$OC_{1-6}$ alkyl" as used herein generally refers to alkoxy groups include an alkyl group (with 1 to 6 carbon atoms) attached to an oxygen atom. Methoxy, ethoxy, n-propoxy, isopropoxy, n-butoxy, sec-butoxy, isobutoxy, tert-butoxy, n-pentoxy, 2-pentoxy, 3-pentoxy, isopentoxy, neopentoxy, hexoxy, 2-hexoxy, 3-hexoxy, and 3-methylpentoxy are representative alkoxy groups.

The term "cycloalkyl" as used herein generally refers to a group that comprises one or more saturated rings in which all ring members are carbon. For example, certain cycloalkyl groups are $C_{3-8}$ cycloalkyl, in which the cycloalkyl group contains one or more rings having from 3 to 8 ring members, all of which are carbon, including, for example, cyclopropyl, cyclobutyl, cyclopentyl, cyclohexyl, cycloheptyl, and cyclooctyl. Other example of cycloalkyl group includes adamantyl. Cycloalkyl groups do not comprise an aromatic ring or a heterocyclic ring. The term "cycloalkenyl" as used herein generally refers to a group that comprises one or more unsaturated rings in which all ring members are carbon.

The terms "heterocyclic" or "heterocycle" or "heterocycyl" or "cycloheteroalkyl" as used herein generally refer to a ring structure (monocycle or polycycle) containing 3-12 ring atoms (3-12 membered heterocycle), 3-8 ring atoms (3-8 membered heterocycle or 3-8 membered cycloheteroalkyl), 3-6 ring atoms (3-6 membered heterocycle or 3-6 membered cycloheteroalkyl), or 5-6 ring atoms (5-6 membered heterocycle or 5-6 membered cycloheteroalkyl), in which at least one ring atom is carbon, and at least one ring atom is heteroatom selected from N, O, and S or a heteroatom group is selected from C(═O), S(═O), and $S(═O)_2$. A heterocyclic group may be aromatic or non-aromatic. Piperidine and oxetane are non-limiting examples of non-aromatic heterocycles. Thiazole and pyridine are non-limiting examples of aromatic heterocycles. Other examples of heterocycle include: aziridinyl, azetidinyl, oxetanyl, pyrrolidinyl, tetrahydrofuranyl, tetrahydrothienyl, piperidinyl, morpholinyl, piperazinyl, thiomorpholinyl, tetrahydropyranyl, 1,1-dioxothiomorpholinyl, butyrolactam, valerolactam, caprolactam, butyrolactone, valerolactone and caprolactone. Similarly, the term "cycloheteroalkenyl" refers to a monocycle or polycycle ring structure comprising carbon atom(s) and heteroatom(s)/heteroatom group(s), wherein the cycloheteroalkenyl comprises at least one C═C double bond, at least one ring atom that is carbon and at least one ring atom that is heteroatom selected from N, O, and S or a heteroatom group selected from C(═O), S(═O), and $S(═O)_2$.

"Aryl" refers to an all-carbon monocyclic or fused-ring polycyclic groups of 6 to 12 ($C_{6-12}$ aryl) or 6 to 10 carbon atoms ($C_{6-10}$ aryl) having a completely conjugated pi-electron system. Examples, without limitation, of aryl groups are phenyl, naphthalenyl, tetrahydronaphthyl, indanyl, biphenyl, and anthracenyl. The aryl group may be substituted or unsubstituted. Typical substituents include halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and $—NR^XR^Y$, wherein $R^X$ and $R^Y$ are independently selected from the group consisting of hydrogen, alkyl, cycloalkyl, aryl, carbonyl, acetyl, sulfonyl, trifluoromethanesulfonyl and, combined, a five- or six-membered heteroalicyclic ring. Illustrative substituted alkyl group include, but are not limited to, fluoromethyl, difluoromethyl, trifluoromethyl, aminomethyl, aminoethyl, hydoxymethyl, methoxymethyl, 2-fluoroethyl, and 2-methoxyethyl, etc.

The term “heteroaryl” as used herein generally refers to an aromatic group in which at least one aromatic ring comprises at least one heteroatom selected from N, O and S. Heteroaryls include, for example, 5-12 membered heteroaryls, 5-10 membered heteroaryls, 5-7 membered monocyclic structures or 7-12 membered bicyclic structures. The number of heteroatoms in a heteroaryl can be 1, 2, 3, 4, or more. Examples included but are not limited to thienyl, pyridyl, pyrimidinyl, pyrazinyl, pyrazolyl, pyridazinyl, pyridine-2(1H)-keto, pyridine-4(1H)-keto, pyrrolyl, pyrazolyl, thiazolyl, 1,2,3-triazolyl, 1,2,4-triazolyl, 1,2,5-oxadiazolyl, imidazolyl, furanyl, tetrazolyl, isothiazolyl, oxazolyl, isoxazolyl, thiadiazolyl, oxadiazolyl, naphthyl, benzothienyl, indolyl, benzimidazolyl, benzothiazolyl, benzofuranyl, quinolinyl, isoquinolinyl, and quinazolinyl. The heteroaryl group may be substituted or unsubstituted. Typical substituents include halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and —$NR^XR^Y$, with $R^X$ and $R^Y$ as defined above.

The term “amino” as used herein generally refers to primary amino group (—$NH_2$), secondary amino group (—NH—), and tertiary amino group ().

The term “alkylamino” as used herein generally refers to a secondary or tertiary amine that has the general structure —NH—$R^1$ or —N($R^1$)($R^2$), respectively, wherein $R^1$ and $R^2$ are selected independently from alkyl, cycloalkyl and (cycloalkyl)alkyl groups. Such groups include, but are not limited to, for example, mono- and di-($C_{1-6}$ alkyl)amino groups, in which each $C_{1-6}$ alkyl may be the same or different. It will be apparent that the definition of “alkyl” as used in the term “alkylamino” differs from the definition of “alkyl” used for all other alkyl-containing groups, in the inclusion of cycloalkyl and (cycloalkyl)alkyl groups.

The term “alkylthio” as used herein generally refers to an alkyl-substituted thio group, wherein the term alkyl is as defined above.

The terms “substituent” and “substituted,” as used herein, generally denote that a molecular moiety is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. A straight chain substituent may be a moiety such as a halogen, alkyl group, haloalkyl group or other group that is covalently bonded to an atom (preferably a carbon or nitrogen atom) that is a member of a straight chain.

The term “bicycloheteroalkyl” as used herein generally refers to a double ring structure which shares one or two atoms and which comprise at least one heteroatom independently selected from the group consisting of N, O, and S in the ring. The term “bicycloheteroalkylene” as used herein generally refers to a di-radical of bicycloheteroalkyl group, which may bind to two other groups.

The term “cycloalkylamine” as used herein generally refers to either a ring structure with an amino group attached to a carbon atom in the ring or a ring structure with a nitrogen atom as member of the ring.

The term “cycloalkylamide” as used herein generally refers to either a ring structure with an amid group attached to a carbon atom in the ring via the amide carbon or a ring structure with both the amide nitrogen and amide carbon atoms becoming members of the ring.

The term “cyclourea” as used herein generally refers to a ring structure with the urea carbon and both urea nitrogen atoms becoming members of the ring. One example of cyclourea is oxoimidazolidine.

The term “pharmaceutically acceptable” as used herein generally refers to a form of the compound that is safe for administration to a subject. For example, a free base, a salt form, a solvate, a hydrate, a prodrug or derivative form of a compound described herein, which has been approved for mammalian use, via oral ingestion or any other route of administration, by a governing authority or regulatory agency, such as the Food and Drug Administration (FDA) of the United States, is pharmaceutically acceptable.

Included in the compounds of Formulas (I), (II) or (III) are the pharmaceutically acceptable salt forms of the free-base compounds. The term “pharmaceutically-acceptable salts” as used herein generally refers to salts, commonly used to form alkali metal salts and to form addition salts of free acids or free bases, which have been approved by a regulatory agency. Salts are formed from ionic associations, charge-charge interactions, covalent bonding, complexation, coordination, etc. The nature of the salt is not critical, provided that it is pharmaceutically acceptable.

As used herein, the term “pharmaceutically acceptable salt” refers to those salts which are, within the scope of sound medical judgment, suitable for use in contact with the tissues of subjects without undue toxicity, irritation, allergic response and the like, and are commensurate with a reasonable benefit/risk ratio. For example, Berge et al. describes pharmaceutically acceptable salts in detail in Pharmaceutical Sciences (1977) 66: 1-19. Pharmaceutically acceptable salts of the compounds provided herein include those derived from suitable inorganic and organic acids and bases. Inorganic acids from which salts can be derived include, but are not limited to, hydrochloric acid, hydrobromic acid, sulfuric acid, nitric acid, phosphoric acid, and the like. Organic acids from which salts can be derived include, but are not limited to, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and other amine salt. Inorganic bases from which salts can be derived include, but are not limited to, sodium, potassium, lithium, ammonium, calcium, magnesium, iron, zinc, copper, manganese, aluminum, and the like. Organic bases from which salts can be derived include, but are not limited to, primary, secondary, and tertiary amines, substituted amines, including naturally occurring substituted amines, cyclic amines, basic ion exchange resins, and the like, examples include, but are not limited to, isopropylamine, trimethylamine, diethylamine, triethylamine, tripropylamine, and ethanolamine. In some embodiments, the pharmaceutically acceptable base addition salt is ammonium, potassium, sodium, calcium, or magnesium salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. Bis salts (i.e., two counterions) and higher salts (e.g., three or more counterions) are encompassed within the meaning of pharmaceutically acceptable salts.

As used herein, the term "ester" refers to organic compounds comprising an ester bond, including monoester, diester, trimester, and polyester.

As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Other solvates include, but are not limited to, methanol, ethanol, isopropanol, ethyl acetate, tetrahydrofuran, dimethyl sulfoxide, and N,N-dimethylformamide Pharmaceutically acceptable solvates and hydrates are complexes that, for example, can include 1 to about 100, or 1 to about 10, or one to about 2, 3 or 4, solvent or water molecules.

As used herein, and unless otherwise specified, "prodrug" refers to a compound that can be converted under physiological conditions or by solvolysis to a biologically active compound described herein. Thus, the term "prodrug" refers to a precursor of a biologically active compound that is pharmaceutically acceptable. A prodrug can be inactive when administered to a subject, but is converted in vivo to an active compound, for example, by hydrolysis. A discussion of prodrugs is provided in Higuchi, T., et al, "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active Formulas (I), (II) or (III) in vivo when such prodrug is administered to a mammalian subject. Prodrugs of an active compound, as described herein, can be prepared by modifying functional groups present in the active Formulas (I), (II) or (III) in such a way that the modifications are cleaved, either in routine manipulation or in vivo, to the parent active compound. Prodrugs include compounds wherein a hydroxy, amino or mercapto group is bonded to any group that, when the prodrug of the active Formulas (I), (II) or (III) is administered to a mammalian subject, cleaves to form a free hydroxy, free amino or free mercapto group, respectively.

The terms "isotope-labelled", "isotope label", "isotope-labelled derivative" and "isotopically labelled" refer to unnatural proportions of atomic isotopes at one or more of atoms that constitute such compounds. For example, the compounds can be radiolabeled with radioactive isotopes, such as, for example, tritium ($^3H$), iodine-125 ($^{125}I$), carbon-14 ($^{14}C$). The compounds can also be isotope-labeled with $^2H$, $^{11}C$, $^{13}C$, $^{15}N$, $^{17}O$, $^{18}O$, $^{18}F$, $^{32}P$, $^{35}S$, and $^{36}Cl$. Certain isotope-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes can allow for ease of preparation and detectability. Further, substitution with heavier isotopes such as deuterium (i.e., H) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of compounds of the present disclosure, whether radioactive or not, are encompassed within the scope of the present disclosure.

The term "isomers" as used herein generally refers to different compounds that have the same molecular formula, including any and all geometric isomers and stereoisomers. "Stereoisomers" are isomers that differ only in the way the atoms are arranged in space. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure, unless specified otherwise. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa).

In some embodiments, the compound(s) of Formulas (I), (II) or (III) is used to treat a subject by administering the compound(s) as a pharmaceutical composition. To this end, the compound(s), in one embodiment, is combined with one or more pharmaceutically acceptable excipients, including carriers, diluents or adjuvants, to form a suitable composition, which is described in more detail herein.

The term "excipient" as used herein generally refers to any pharmaceutically acceptable additive, carrier, adjuvant, or other suitable ingredient, other than the active pharmaceutical ingredient (API), which is typically included for formulation and/or administration purposes.

The term "diluent" as used herein generally refers to an agent used as filler in order to achieve the desired composition volume or weight. The diluent may be present in the pharmaceutical composition within granules in the form of a single compound or in the form of a mixture of compounds. Non-limiting examples of diluent include lactose, starch, pregelatinized starch, microcrystalline cellulose, silicified microcrystalline cellulose, cellulose acetate, dextrose, mannitol, sodium phosphate, potassium phosphate, calcium phosphate, fructose, maltose, sorbitol, or sucrose.

The term "adjuvant," as used herein generally refers to any substance or mixture of substances that increases the efficacy or potency of a compound disclosed herein on a target where the adjuvant is used together with the compound disclosed herein. However, when the adjuvant is used alone, no pharmacological effect is observed on the same target.

The terms "treat", "treating," "treatment," and "therapy" as used herein generally refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals. Treatment includes the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The phrase "effective amount" as used herein generally refers to quantifying the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

Regardless of the route of administration selected, the compounds of the present invention, which may be used in a suitable hydrated form, and/or the pharmaceutical compositions of the present invention, are formulated into pharmaceutically acceptable dosage forms or by other conventional methods known to those of skill in the art.

Actual dosage levels of the active ingredients in the pharmaceutical compositions of the present invention may be varied so as to obtain an effective amount of the active ingredient to achieve the desired therapeutic response for a particular patient, composition, and mode of administration, without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular hedgehog inhibitor employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. The mode of administration can have a large effect on dosage. Higher doses may be used for localized routes of delivery.

If desired, the effective daily dose of the active compound may be administered as two, three, four, five, six or more sub-doses administered separately at appropriate intervals throughout the day, optionally, in unit dosage forms. Those of skill in the art will readily appreciate that dose levels can vary as a function of the specific compound, the severity of the symptoms and the susceptibility of the subject to side effects. Dosages for a given compound disclosed herein are readily determinable by those of skill in the art by a variety of means.

PHARMACEUTICAL COMPOSITIONS/FORMULATIONS

One embodiment provides a pharmaceutical composition comprising a compound of Formulas (I), (II) or (III), or a stereoisomer, tautomer, hydrate, solvate or pharmaceutically acceptable salt thereof, and at least one pharmaceutically acceptable excipient.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: *The Science and Practice of Pharmacy*, Nineteenth Ed., Easton, Pa.: Mack Publishing Company (1995);

Hoover, John E., *Remington's Pharmaceutical Sciences*, Mack Publishing Co., Easton, Pennsylvania (1975); Liberman, H. A. and Lachman, L., Eds., *Pharmaceutical Dosage Forms*, Marcel Decker, New York, N.Y. (1980); and *Pharmaceutical Dosage Forms and Drug Delivery Systems*, Seventh Ed., Lippincott Williams & Wilkins (1999), herein incorporated by reference for such disclosure.

A pharmaceutical composition, as used herein, refers to a mixture of a compound of Formulas (I), (II) or (III) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

All formulations for oral administration are in dosages suitable for such administration. Examples of such dosage units are tablets or capsules. In some embodiments, these contain an amount of active ingredient from about 1 to 2000 mg, advantageously from about 1 to 500 mg, and typically from about 5 to 150 mg. A suitable daily dose for a human or other mammal vary widely depending on the condition of the patient and other factors, but, once again, can be determined using routine methods and practices.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Synthetic Methods

Methods of the present invention may include the use of at least one compound of Formulas (I), (II) or (III), which inhibits programmed necrosis in the regulation of repair and/or functional performance of a wide range of cells, tissues and organs, and have therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Accordingly, the methods and compositions of the present invention include the use of the subject inhibitors for all such uses as inhibitors of programmed necrosis may be implicated. Moreover, the subject methods can be performed on cells which are provided in culture (in vitro), or on cells in a whole animal (in vivo).

The examples and preparations provided below illustrated and exemplify the compounds described herein and methods of preparing such compounds. In general, the compounds described herein may be prepared by processes known in the general chemical arts.

The compounds of the present invention can be prepared using various synthetic routes, including those described below, starting from commercially available materials. Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Functional groups may be removed according to known procedures in the art.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981).

All synthetic procedures described herein can be carried out under known reaction conditions, advantageously under those described herein, either in the absence or in the presence (usually) of solvents or diluents.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described above.

All reagents and solvents were obtained commercially unless stated otherwise. All commercial reagents and solvent were used without purification unless stated otherwise. When required, some reagents and solvents were purified by standard techniques. For example, tetrahydrofuran may be purified by distillation from sodium. All thin-layer chromatography (TLC, GF254) analyses and column purification (100-200 mesh) were performed on silica gel (Qingdao Haiyang Chemical Co. Ltd. or Yantai Chemical Co. Ltd.), using petroleum ether (b.p. 60-90° C.)/ethyl acetate (v/v) as eluent; and spots revealed by UV visualization at 254 nm and $I_2$ vapor or phosphomolybdic acid. All organic layers after extraction were dried over anhydrous $Na_2SO_4$ unless stated otherwise. All nuclear magnetic resonance spectra ($^1H$ NMR) were recorded using a Varian-400 spectrometer at 400 MHz using TMS as an internal standard. LC-MS was run using an Agilent 1100 system with LC-MSDTrap recorder, diode array detector (DAD) with detecting wavelength at 214 nm and 254 nm, and ESI source. The HPCL column is an AgelaDurashell C18 3.5 μm 4.6×50 mm column Gradients were run using $0.1NH_4HCO_3$ aqueous solution and acetonitrile with gradient 5/95 to 95/5 in the run time indicated (for example, 5 min), flow rate at 1.8 mL/min.

The size and scale of the synthetic methods will vary depending on the desired amount of end product. It is understood that while specific reactants and amounts are provided in the Examples, one of skill in the art knows other alternative and equally feasible sets of reactants that will also yield the same compounds. Thus, where general oxidizers, reducers, solvents of various nature (aprotic, apolar, polar, etc.) are utilized, equivalents will be known in the art and are herein contemplated for use in the present methods.

Many of the steps below indicate various work-ups following termination of the reaction. A work-up involves generally quenching of a reaction to terminate any remaining catalytic activity and starting reagents. This is generally followed by addition of an organic solvent and separation of the aqueous layer from the organic layer. The product is typically obtained from the organic layer and unused reactants and other spurious side products and unwanted chemicals are generally trapped in the aqueous layer and discarded. The work-up in standard organic synthetic procedures found throughout the literature is generally followed by drying the product by exposure to a drying agent, such as anhydrous $Na_2SO_4$, to remove any excess water or aqueous byproducts remaining partially dissolved in the organic layer and concentration of the remaining organic layer. Concentration of product dissolved in solvent may be achieved by any known means, such as evaporation under pressure, evaporation under increased temperature and pressure, and the like. Such concentrating may be achieved by use of standard laboratory equipment such as rotary-evaporator distillation, and the like. This is optionally followed by one or more purification steps which may include, but is not limited to, flash column chromatography, filtration through various media and/or other preparative methods known in the art and/or crystallization/recrystallization. (See, for instance, Addison Ault, "Techniques and Experiments for Organic Chemistry," 6th Ed., University Science Books, Sausalito, Calif., 1998, Ann B. McGuire, Ed., pp. 45-59).

ABBREVIATIONS

DCM means dichloromethane.
DCE means 1,2-dichloroethane.
DMF means N,N-dimethylformamide
EtOAc or EA means ethyl acetate.
MeOH means methyl alcohol.
EtOH means ethyl alcohol.
$Ph_2O$ means diphenylether.
Dioxane is 1,4-dioxane.
Xantphos is (9,9-Dimethyl-9H-xanthene-4,5-diyl)bis(diphenylphosphane).
$Pd_2(dba)_3$ is tris(dibenzylideneacetone)dipalladium(0).
DEAD is diethyl azodicarboxylate.
NBS is N-bromosuccinimide
CDI is 1,1'-carbonyldiimidazole.
THF is tetrahydrofuran.
$PMBNH_2$ is 4-methoxybenzylamine
$Et_3N$ is triethylamine
Con. HCl or conc. HCl means concentrated hydrochloric acid.
Sol. HCl means diluted hydrochloric acid.
TLC means thin layer chromatography.
HATU means 1-[bis(dimethylamino)methylene]-1H-1,2,3-triazolo[4,5-b]pyridinium 3-oxid hexafluorophosphate.
DIPEA means diisopropylethylamine.
HPLC means high-performance liquid chromatography.
LC-MS means liquid chromatography—mass spectrometry.
NMR means nuclear magnetic resonance.

General Synthetic Routes

The following Methods A-J are embodiments for some general synthetic routes leading to compounds of Formulas (I), (II) or (III). Detailed reaction conditions for each Method can be found in the examples shown vide infra.

Method A:

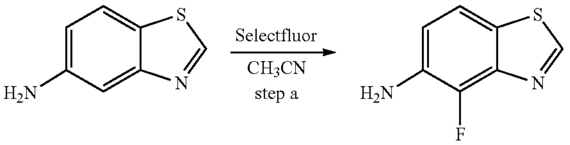 [SMILES: Nc1ccc2scnc2c1 ; Nc1ccc2scnc2c1F]

Fluorination of benzo[d]thiazol-5-amine with selectfluor yielded the corresponding product (step a).

Method B

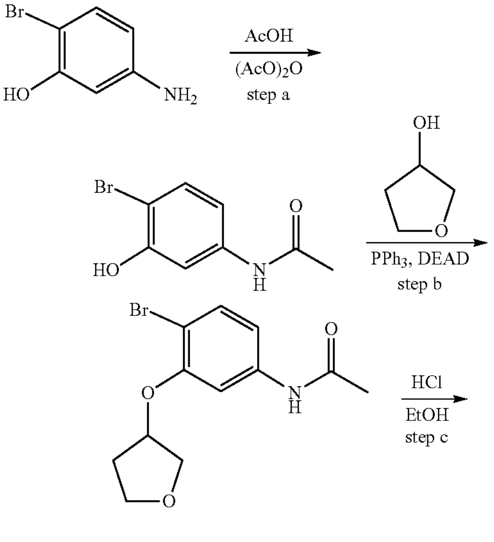

-continued

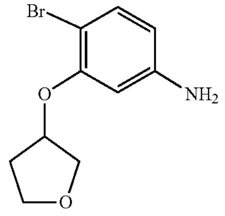

Acetylation of 5-amino-2-bromophenol with acetic anhydride followed by Mitsunobu reaction yielded N-(4-bromo-3-((tetrahydrofuran-3-yl)oxy)phenyl)acetamide (step a, b). Deacetylation with conc. HCl afforded the corresponding compound (step c).

Method C

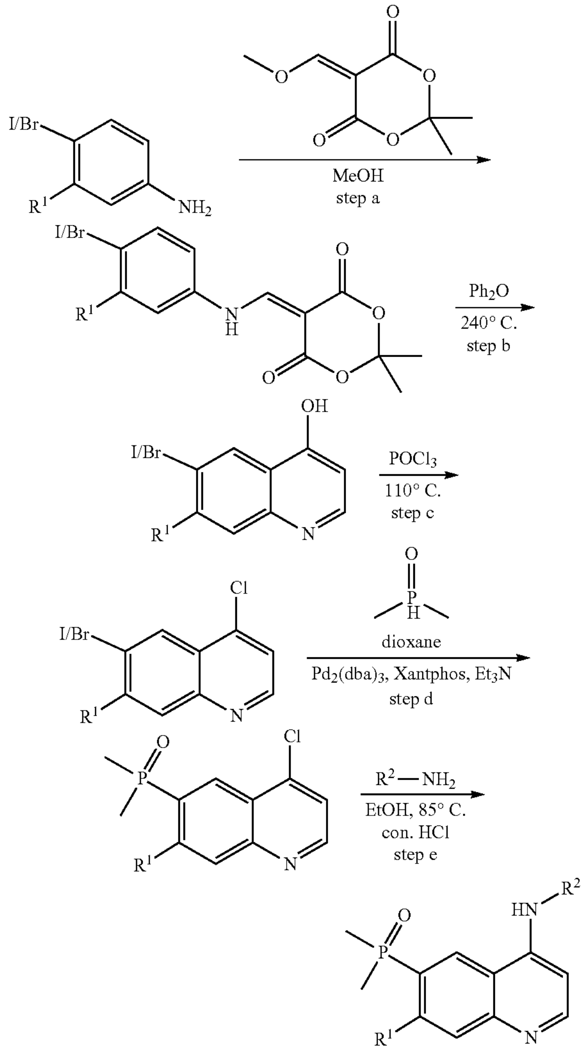

Commercially available anilines were reacted with 5-(methoxymethylene)-2,2-dimethyl-1,3-dioxane-4,6-dione followed by cyclization in inert solvent at high temperature to form quinoline derivatives (step a, b). Chlorination with $POCl_3$ followed by coupling with dimethylphosphine oxide was to give the corresponding intermediates (step c, d). Final compounds were achieved through $S_NAr$ reaction with respective aromatic amines (step e).

Method D

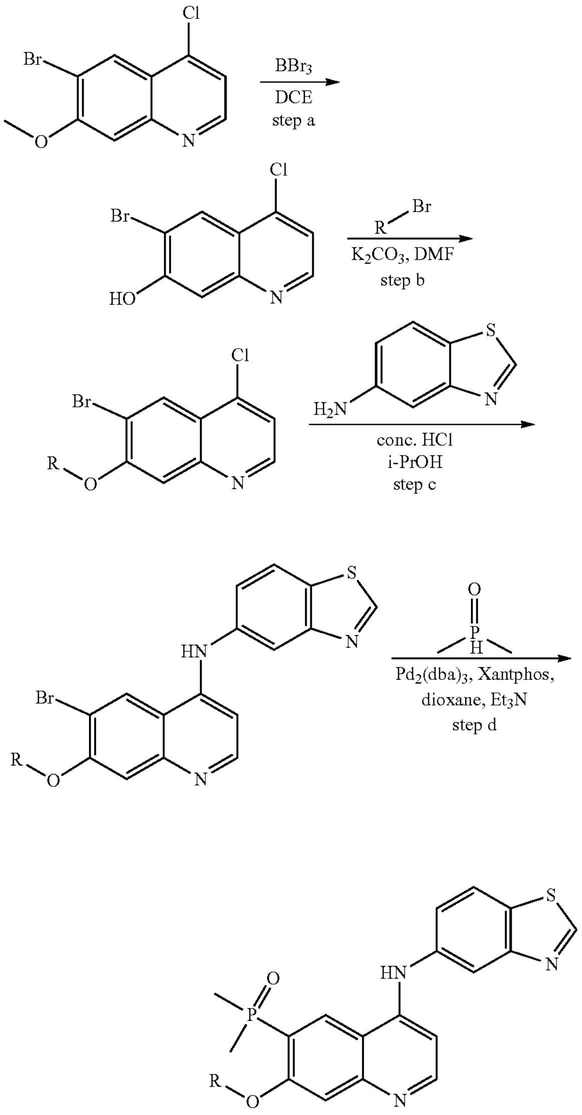

Demethylation of the 7-methoxy group of 6-bromo-4-chloro-7-methoxyquinoline using $BBr_3$ was followed by alkylation of the newly exposed hydroxyl group with alkyl bromide to give the corresponding intermediates (step a, b). $S_NAr$ reaction was carried out in the presence of conc. HCl (step c). The resulting compounds were coupled with dimethylphosphine oxide to give the final products (step d).

Method E

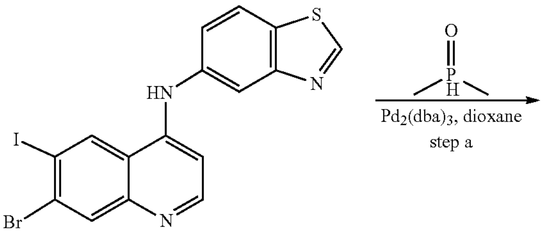

-continued

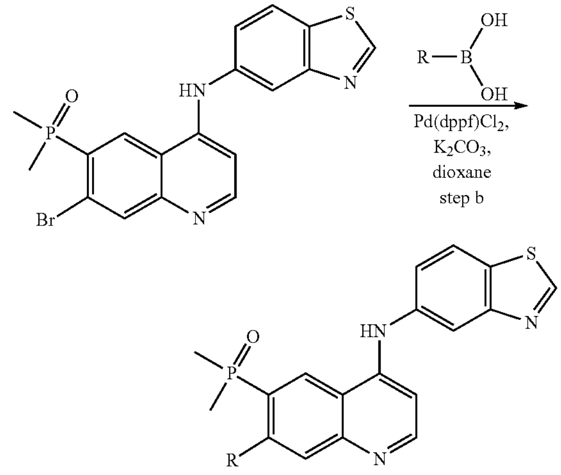

Palladium-catalyzed coupling with dimethylphosphine oxide followed by Suzuki coupling reaction with respective arylboronic acids afforded the corresponding final compounds (step a, b).

Method F

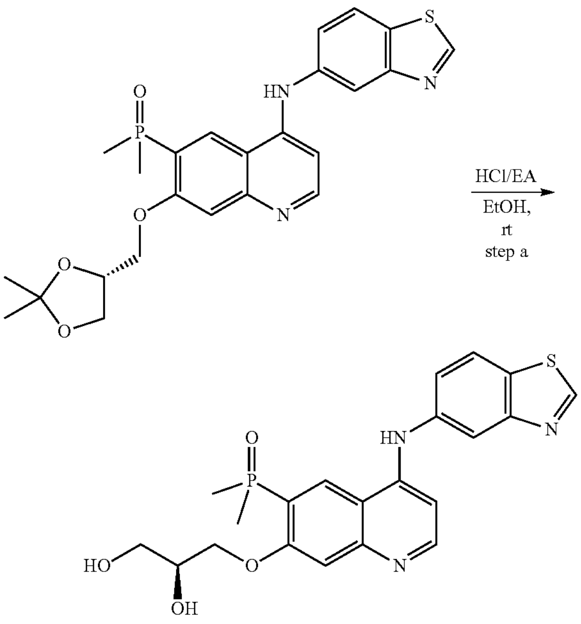

Deprotection of 1,3-dioxolane containing intermediate with HCl·EA gave the final compound (step a).

Method G

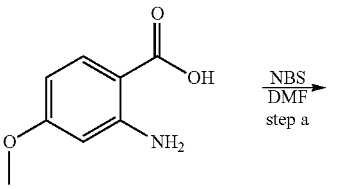

-continued

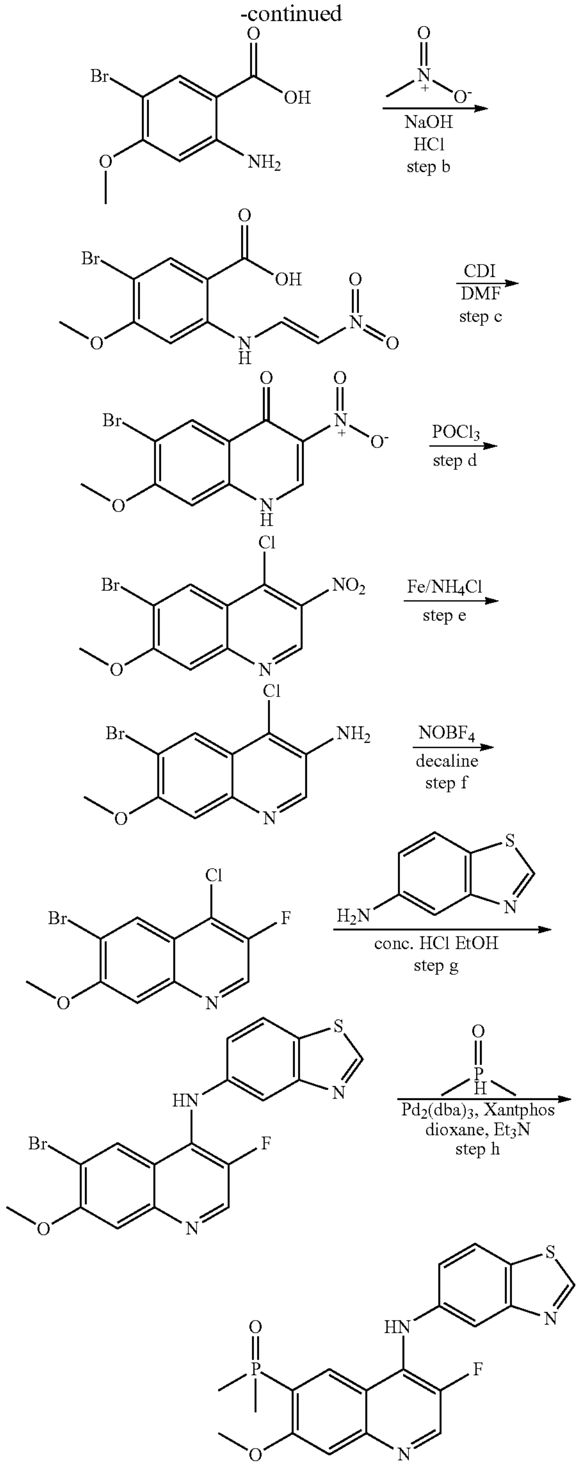

Bromination of commercially available 2-amino-4-methoxybenzoic acid with NBS yielded brominated derivative (step a). Which was reacted with nitromethane under basic condition to form the corresponding intermediate (step b). Quinoline was generated through an intramolecular ring closure reaction using CDI (step c). Nitro group was reduced by iron powder to form amine which was converted to fluorine through a Sandmeyer reaction (step e, f). Condensation with benzo[d]thiazol-5-amine followed by a coupling reaction afforded the final compound (step g, h).

Method H

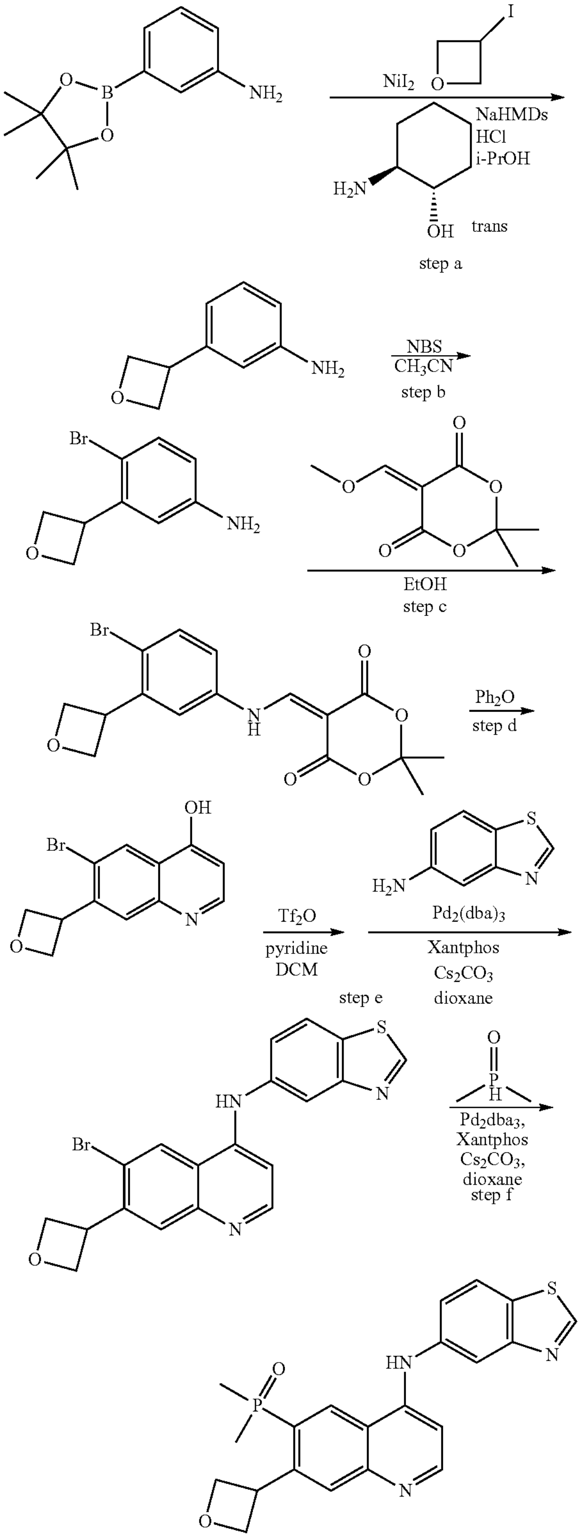

Nickel-catalyzed coupling between 3-(4,4,5,5-tetramethyl-1,3,2-dioxaborolan-2-yl)aniline and 3-iodooxetane yielded oxetane containing intermediate (step a). Treatment with NBS gave 4-bromo-3-(oxetan-3-yl)aniline which was reacted with 5-(methoxymethylene)-2,2-dimethyl-1,3-dioxane-4,6-dione (step b, c). Quinoline was generated through an intramolecular ring closure reaction (step d). Activation of hydroxyl with $Tf_2O$ followed by Buchwald-Hartwig coupling with benzo[d]thiazol-5-amine afforded the corresponding intermediate (step e). The final compound was got by coupling reaction with dimethylphosphine oxide (step f).

Method I

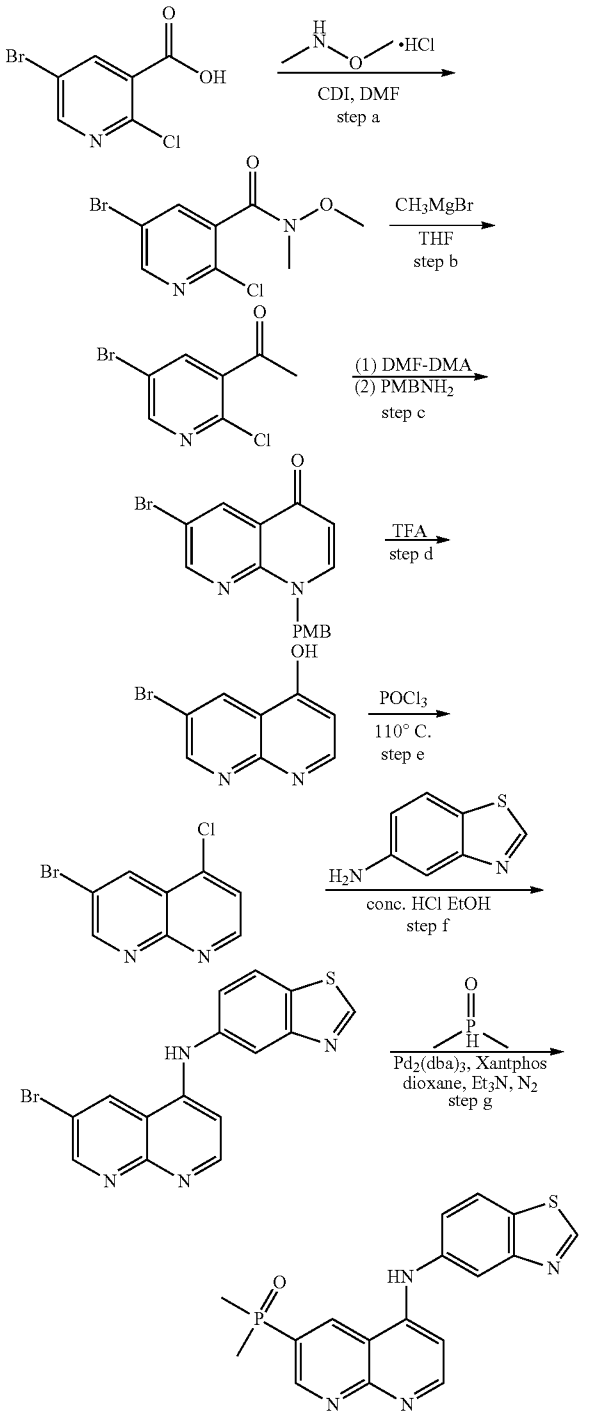

Condensation of 5-bromo-2-chloronicotinic acid with N,O-dimethylhydroxylamine followed by Grignard reaction with methylmagnesium bromide yielded 1-(5-bromo-2- chloropyridin-3-yl)ethan-1-one. Treatment with DMF-DMA followed by PMB-$NH_2$ gave 6-bromo-1-(4-methoxybenzyl)-1,8-naphthyridin-4(1H)-one. Deprotection of PMB group afforded 6-bromo-1,8-naphthyridin-4-ol. whose hydroxyl group was converted to chlorine with $POCl_3$. $S_NAr$ reaction was carried out with benzo[d]thiazol-5-amine under acidic condition followed by coupling reaction to give the final compound.

Method J

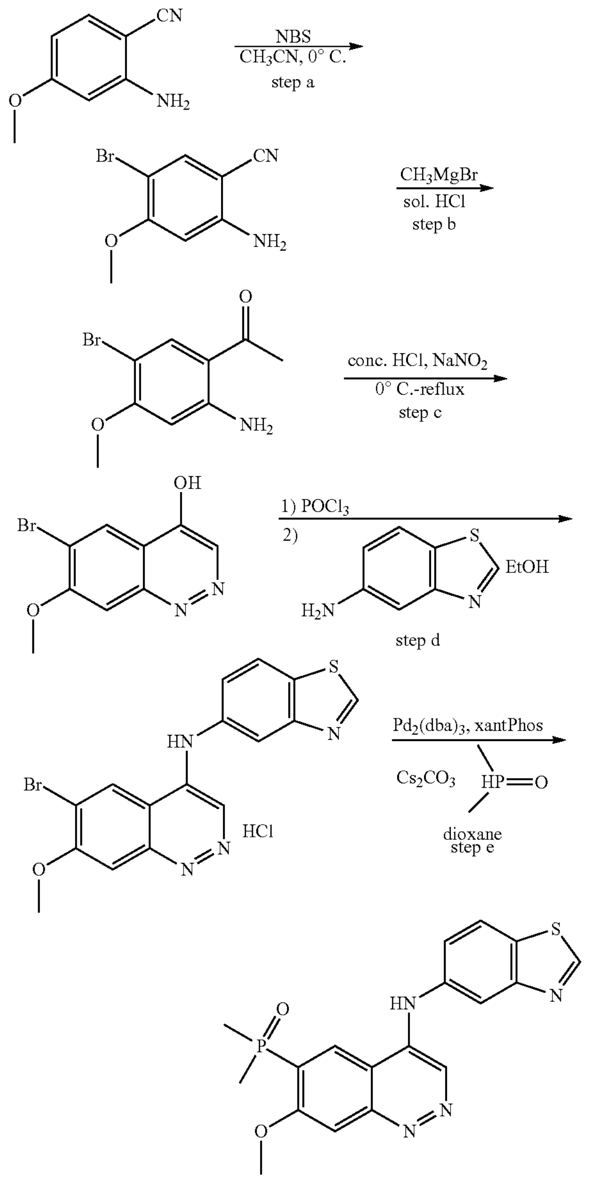

Bromination of 2-amino-4-methoxybenzonitrile with NBS followed by Grignard reaction with methylmegasium bromide yielded 1-(2-amino-5-bromo-4-methoxyphenyl) ethan-1-one. Treatment with $NaNO_2$ gave cinnoline derivative. Whose hydroxyl group was converted to chlorine with $POCl_3$ followed by $S_NAr$ reaction with benzo[d]thiazol-5-amine to give the corresponding intermediate. Palladium-catalyzed coupling with methylphosphine oxide afforded the desired product.

EXAMPLE 1, METHOD A

Preparation of 4-fluorobenzo[d]thiazol-5-amine

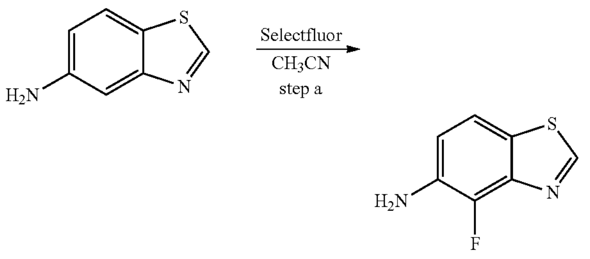

Step a. 4-fluorobenzo[d]thiazol-5-amine: To a solution of benzo[d]thiazol-5-amine (3.0 g, 20 mmol) in acetonitrile (80 mL) was added selectfluor (7.0 g, 20 mmol) in acetonitrile (20 mL). The mixture was stirred at room temperature for 1 hour. Water (200 mL) was added to the reaction and the organic layer was extracted by dichloromethane (100 mL×3). The combined organic layers were dried over $Na_2SO_4$ and concentrated under vacuum. The residue was purified by silica gel column chromatography (petroleum ether/ethyl acetate (v/v)=4/1) to give the desired product (310 mg, 9.2%) as a yellow solid. $^1H$ NMR (300 MHz, $CDCl_3$) δ 8.92 (s, 1H), 7.48 (d, J=8.4 Hz, 1H), 6.97 (t, J=8.1 Hz, 1H), 3.87 (s, 2H). LC-MS (m/z): 169.0 $[M+H]^+$.

EXAMPLE 2, METHOD B

Preparation of 4-bromo-3-((tetrahydrofuran-3-yl)oxy)aniline

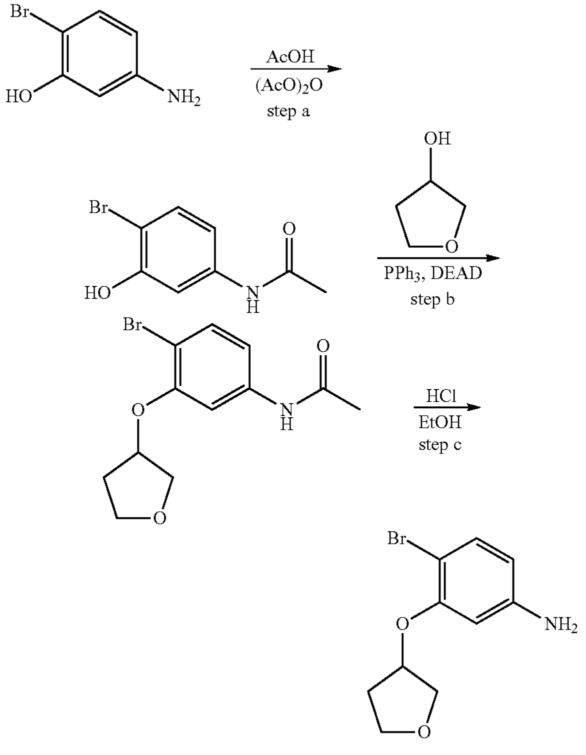

Step a. N-(4-bromo-3-hydroxyphenyl)acetamide: 5-amino-2-bromophenol (660 mg, 3.5 mmol) was dissolved in acetic acid (5 mL) and acetic anhydride (396 mg, 3.9 mmol) was added. The mixture was stirred for 10 minutes at room temperature. Water (200 mL) was added and the resulting solid was filtered, dried under vacuum to give the desired product (600 mg, 74%) as a white solid. $^1$H NMR (400 MHz, DMSO-$d_6$) δ 10.21 (s, 1H), 9.93 (s, 1H), 7.47 (s, 1H), 7.33 (d, J=8.8 Hz, 1H), 6.86 (d, J=8.4 Hz, 1H), 2.01 (s, 3H). LC-MS (m/z): 229.8 $[M+H]^+$.

Step b. N-(4-bromo-3-((tetrahydrofuran-3-yl)oxy)phenyl) acetamide: To a solution of N-(4-bromo-3-hydroxyphenyl)acetamide (600 mg, 2.61 mmol) in dry tetrahydrofuran (5 mL) was added $PPh_3$ (1.37 g, 5.22 mmol) and diethyl azodicarboxylate (909 mg, 5.22 mmol). The mixture was stirred at room temperature for 30 minutes under nitrogen. Tetrahydrofuran-3-ol (275 mg, 3.13 mmol) was added and the mixture was stirred for 2 hours. The solvent was removed in vacuum and the residue was purified by silica gel column chromatography (petroleum ether/ethyl acetate (v/v)=5/1) to give the crude product (960 mg) as a white solid. LC-MS (m/z): 299.7 $[M+H]^+$.

Step c. 4-bromo-3-((tetrahydrofuran-3-yl)oxy)aniline: To a solution of crude intermediate N-(4-bromo-3-((tetrahydrofuran-3-yl)oxy)phenyl)acetamide (960 mg) in ethanol (15 mL) was added conc. HCl (4 mL). The mixture was stirred at 85° C. for 3 hours. The solvent was concentrated to give the corresponding crude product (620 mg). LC-MS (m/z): 257.8 $[M+H]^+$.

EXAMPLE 3, METHOD C

Prepare of (4-(benzo[d]thiazol-5-ylamino)quinolin-6-yl)dimethylphosphine oxide hydrochloride (A1)

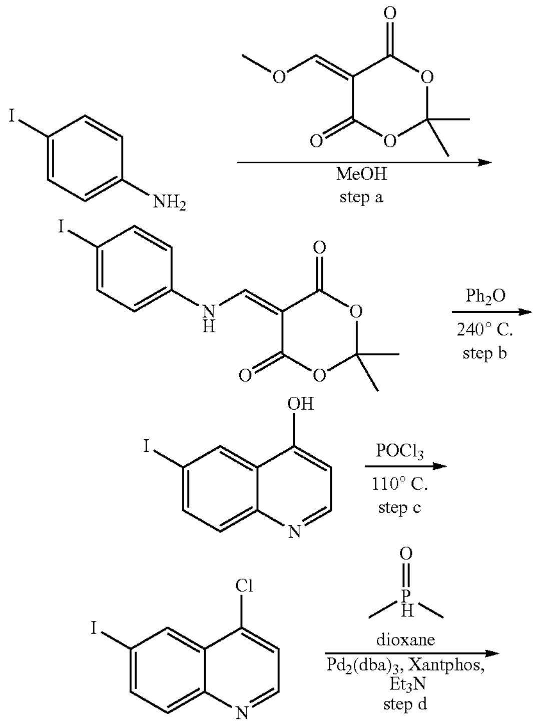

-continued

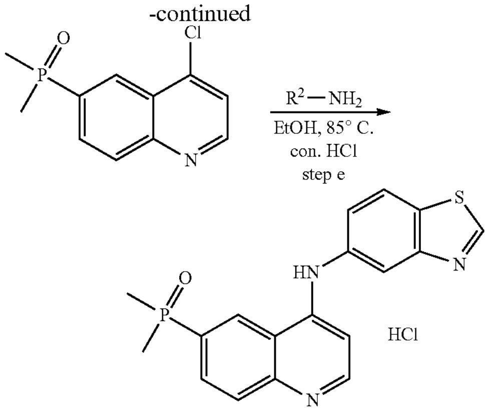

Step a. 5-(((4-iodophenyl)amino)methylene)-2,2-dimethyl-1,3-dioxane-4,6-dione: To a solution of 4-iodoaniline (1.0 g, 4.57 mmol) in methanol (15 mL) was added 5-(methoxymethylene)-2,2-dimethyl-1,3-dioxane-4,6-dione (1.3 g, 6.85 mmol). The mixture was stirred at room temperature for 30 minutes. The resulting solid was collected via filtration, washed with ethanol (3 mL) and dried under vacuum to give the desired product (1.2 g, 70%) as a light yellow solid. $^1$H NMR (400 MHz, DMSO-$d_6$) δ 11.21 (d, J=14.4 Hz, 1H), 8.54 (d, J=14.4 Hz, 1H), 7.76 (d, J=8.0 Hz, 2H), 7.40 (d, J=8.0 Hz, 2H), 1.67 (s, 6H).

Step b. 6-iodoquinolin-4-ol: The diphenyl ether (140 mL) was added to a round-bottomed flask and the solvent was heated to 240° C. for 20 minutes. Intermediate 5-(((4-iodophenyl)amino)methylene)-2,2-dimethyl-1,3-dioxane-4,6-dione (1.2 g, 3.2 mmol) was added slowly to the solution. The mixture was stirred for 3 minutes. After cooling to room temperature, Petroleum ether (80 mL) was added to the reaction and the resulting solid was collected via filtration, rinsed with ethyl acetate (20 mL) and dried under vacuum to give the desired product (850 mg, 98%) as a white solid. $^1$H NMR (400 MHz, DMSO-$d_6$) δ 11.87 (s, 1H), 8.36 (s, 1H), 7.97-7.87 (m, 2H), 7.37 (d, J=8.4 Hz, 1H), 6.07 (d, J=7.2 Hz, 1H). LC-MS (m/z): 271.7 $[M+H]^+$.

Step c. 4-chloro-6-iodoquinoline: 6-iodoquinolin-4-ol (200 mg, 0.74 mmol) was added to $POCl_3$ (5 mL) and the mixture was allowed to stir at reflux for 15 minutes to afford a light brown solution. After cooling to room temperature, the excess $POCl_3$ was removed in vacuum. The residue was dissolved in ethyl acetate (10 mL). Saturated $NaHCO_3$ solution was used to adjust pH to 7. The organic layer was extracted with ethyl acetate (60 mL×2). The combined organic layers were dried by $Na_2SO_4$ and concentrated. The residue was purified by silica gel column chromatography (petroleum ether/ethyl acetate (v/v)=5/1) to give the desired product (200 mg, 94%). $^1$H NMR (400 MHz, DMSO-$d_6$) δ 8.87 (d, J=4.0 Hz, 1H), 8.54 (s, 1H), 8.15 (d, J=8.8 Hz, 1H), 7.88 (d, J=8.8 Hz, 1H), 7.81 (d, J=4.0 Hz, 1H).

Step d. (4-chloroquinolin-6-yl)dimethylphosphine oxide: To a solution of 4-chloro-6-iodoquinoline (200 mg, 0.69 mmol) in 1,4-dioxane (5 mL) was added dimethylphosphine oxide (81 mg, 1.04 mmol), $Et_3N$ (118 mg, 1.17 mmol), $Pd_2dba_3$ (32 mg, 0.03 mmol) and Xantphos (40 mg, 0.07 mmol). The mixture was stirred at room temperature under $N_2$ atmosphere overnight. The solvent was removed in vacuum and the residue was purified by silica gel column chromatography (dichloromethane/methanol (v/v)=50/1) to give the desired product (100 mg, 60%). $^1$H NMR (400 MHz, DMSO-$d_6$) δ 8.96 (d, J=4.4 Hz, 1H), 8.64 (d, J=12.4 Hz, 1H), 8.27-8.13 (m, 2H), 7.89 (d, J=4.4 Hz, 1H), 1.79 (s, 3H), 1.76 (s, 3H).

Step e. (4-(benzo[d]thiazol-5-ylamino)quinolin-6-yl)dimethylphosphine oxide hydrochloride: (4-chloroquinolin-6-yl)dimethylphosphine oxide (100 mg, 0.42 mmol) was dissolved in ethanol (3 mL) and benzo[d]thiazol-5-amine (67 mg, 0.46 mmol) was added subsequently. The mixture was stirred at reflux for an hour. After cooling to room temperature. The resulting solid was collected via filtration, washed with ethanol and dried in vacuum to give the desired product (50 mg, 34%) as a hydrochloride salt.

EXAMPLE 4, METHOD D

Prepare of (4-(benzo[d]thiazol-5-ylamino)-7-(2-hydroxyethoxy)quinolin-6-yl)dimethylphosphine oxide (A7)

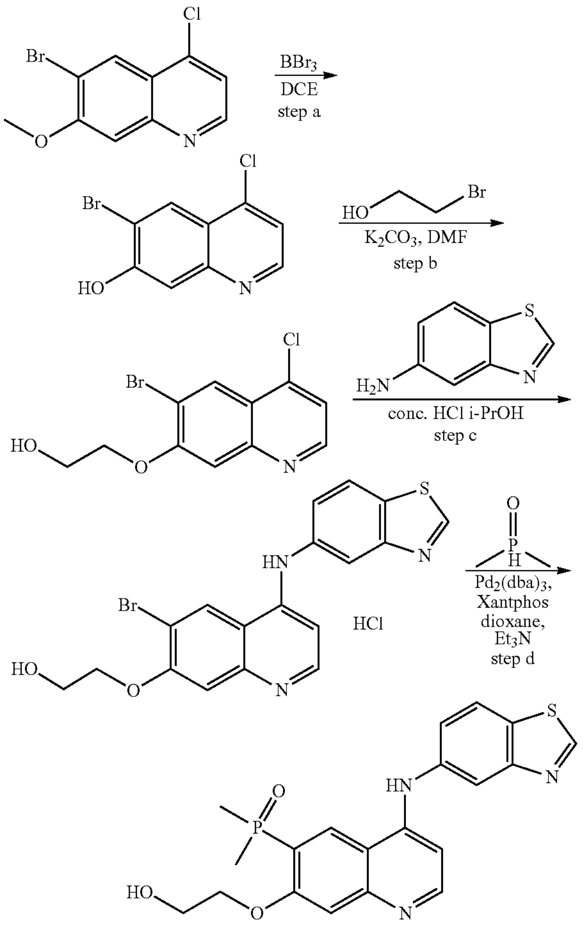

Step a. 6-bromo-4-chloroquinolin-7-ol: To a solution of 6-bromo-4-chloro-7-methoxyquinoline (2.8 g, 10.3 mmol) in 1,2-dichloroethyl (10 mL) was added $BBr_3$ (10.3 mL, 31.0 mmol) at room temperature. The mixture was stirred at 110° C. under microwave irradiation for 1 hour. The reaction was quenched by saturated $Na_2SO_3$ solution and extracted with dichloromethane (50 mL×2). The organic layer was combined, dried over $Na_2SO_4$ and concentrated. The residue was purified by silica gel column chromatography (dichloromethane/methanol (v/v)=50/1) to give the desired product (1.7 g, 64%). $^1$H NMR (400 MHz, DMSO-$d_6$) δ 11.86 (s, 1H), 8.87 (d, J=5.2 Hz, 1H), 8.42 (s, 1H), 7.75 (d, J=5.2 Hz, 1H), 7.55 (s, 1H). LC-MS (m/z): 257.7 $[M+H]^+$.

Step b. 2-((6-bromo-4-chloroquinolin-7-yl)oxy)ethan-1-ol: To a solution of 6-bromo-4-chloroquinolin-7-ol (200 mg, 0.77 mmol) in N,N-dimethylformamide (3 mL) was added $K_2CO_3$ (215 mg, 1.55 mmol). The mixture was stirred at 80° C. for 30 minutes. 2-Bromoethanol (193 mg, 1.55 mmol) was added subsequently and the mixture was stirred at 80° C. overnight. The solvent was removed in vacuum and the residue was purified by silica gel column chromatography (dichloromethane/methanol (v/v)=50/1) to give the desired product (150 mg, 64%). LC-MS (m/z): 301.7 $[M+H]^+$.

Step c. 2-((4-(benzo[d]thiazol-5-ylamino)-6-bromoquinolin-7-yl)oxy)ethan-1-ol hydrochloride: To a solution of 2-((6-bromo-4-chloroquinolin-7-yl)oxy)ethan-1-ol (150 mg, 0.5 mmol) was added benzo[d]thiazol-5-amine (93 mg, 0.62 mmol). The mixture was stirred at reflux for 30 minutes. After cooling to room temperature. The resulting solid was collected via filtration, washed with ethanol and dried in vacuum to give the desired product (120 mg, 58%) as a hydrochloride salt. $^1$H NMR (400 MHz, DMSO-$d_6$) δ 14.27 (s, 1H), 11.03 (s, 1H), 9.53 (s, 1H), 9.17 (s, 1H), 8.45 (d, J=6.4 Hz, 1H), 8.37 (d, J=8.4 Hz, 1H), 8.20 (s, 1H), 7.60 (d, J=8.4 Hz, 1H), 7.56 (s, 1H), 6.81 (d, J=6.8 Hz, 1H), 4.28 (s, 2H), 3.88 (s, 2H). LC-MS (m/z): 415.6 $[M+H]^+$.

Step d. (4-(benzo[d]thiazol-5-ylamino)-7-(2-hydroxyethoxy)quinolin-6-yl)dimethylphosphine oxide: To a solution 24(4-(benzo[d]thiazol-5-ylamino)-6-bromoquinolin-7-yl)oxy)ethan-1-ol hydrochloride (120 mg, 0.29 mmol) in 1,4-dioxane (3 mL) was added dimethylphosphine oxide (34 mg, 0.43 mmol), $Et_3N$ (50 mg, 0.49 mmol), $Pd_2dba_3$ (26 mg, 0.03 mmol) and Xantphos (18 mg, 0.03 mmol). The mixture was stirred at 125° C. under microwave irritation for 1 hour. The solvent was removed in vacuum and the residue was purified by silica gel column chromatography (dichloromethane/methanol (v/v)=20/1) to give the desired product (30 mg, 25%).

EXAMPLE 5, METHOD E

Preparation of (4-(benzo[d]thiazol-5-ylamino)-7-(1-methyl-1H-pyrazol-4-yl)quinolin-6-yl)dimethylphosphine oxide (A11)

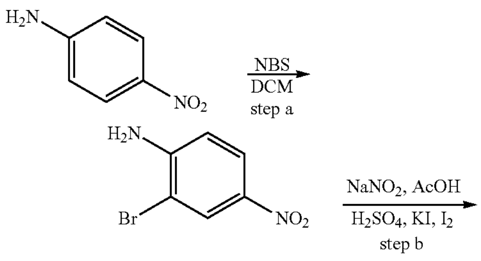

-continued

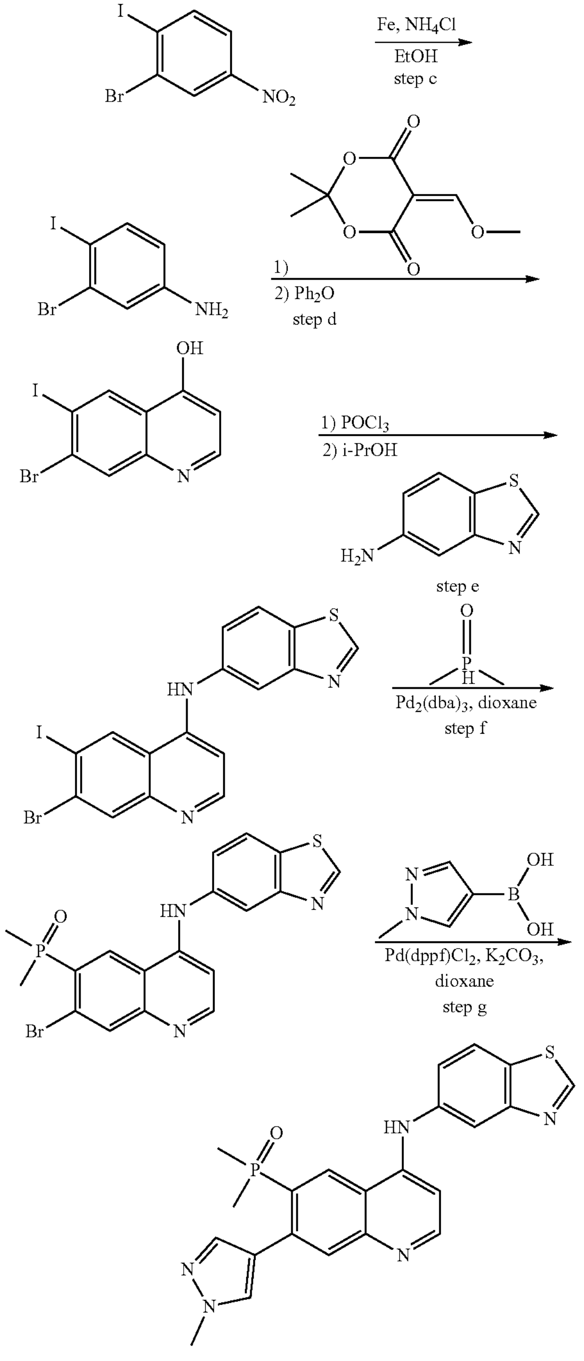

Step a. 2-bromo-4-nitroaniline: To a solution of 4-nitroaniline (10 g, 72.5 mmol) in dichloromethane (60 mL) was added NBS (13 g, 72.5 mmol). The mixture was stirred at room temperature overnight. Saturated $NaHCO_3$ solution was added to quench the reaction. The organic layer was separated, dried over $Na_2SO_4$ and concentrated to give the crude product (15 g, 96%) as a yellow solid. LC-MS (m/z): 216.7 $[M+H]^+$.

Step b. 2-bromo-1-iodo-4-nitrobenzene: To a solution of 2-bromo-4-nitroaniline (7.0 g, 32.3 mmol) in acetic acid (80 mL) was added $NaNO_2$ (2.4 g, 34.8 mmol) in conc·$H_2SO_4$ (16 mL) at 0° C. The reaction was stirred for 4 hours. A mixture of KI (16 g, 96.9 mmol) and I 2 (3.5 g, 32.3 mmol) dissolved in water (60 mL) was added and the reaction was stirred at room temperature overnight. 15% NaOH solution was added to quench the reaction. The organic layer was extracted by ethyl acetate (300 mL), dried over $Na_2SO_4$ and concentrated to give the desired product (10.0 g, 95%).

Step c. 3-bromo-4-iodoaniline: To a solution of 2-bromo-1-iodo-4-nitrobenzene (10.0 g, 30.7 mmol) in ethanol (60 mL) was added $NH_4Cl$ (8.2 g, 153 mmol) and iron powder (8.5 g, 153 mmol). The mixture was stirred at 85° C. for 2 hours. The reaction was filtered through diatomaceous earth and the cake was washed with ethanol. The resulting filtrate was concentrated and the residue was purified by silica gel column chromatography to give the desired product (6.0 g, 65%) as a yellow solid. $^1H$ NMR (400 MHz, $CDCl_3$) δ 8.45 (s, 1H), 8.08 (d, J=8.8 Hz, 1H), 7.85 (d, J=8.4 Hz, 1H), LC-MS (m/z): 297.6 $[M+H]^+$.

Step d. 7-bromo-6-iodoquinolin-4-ol: To a solution of 3-bromo-4-iodoaniline (6.0 g, 20 mmol) in ethanol (30 mL) was added 5-(methoxymethylene)-2,2-dimethyl-1,3-dioxane-4,6-dione (7.4 g, 40 mmol). The mixture was stirred at room temperature for 2 hours. The resulting solid was collected via filtration, dried in vacuum to give a crude product. $Ph_2O$ (30 mL) was added to a round-bottomed flask and the crude product was added subsequently. The reaction was stirred at 220° C. for 3 minutes. After cooling to room temperature. The resulting solid was filtered, washed with ethyl ether and dried in vacuum to give the desired product (4.0 g). LC-MS (m/z): 349.5 $[M+H]^+$.

Step e. N-(7-bromo-6-iodoquinolin-4-yl)benzo[d]thiazol-5-amine 7-bromo-6-iodoquinolin-4-ol (2.0 g, 5.75 mmol) was added to $POCl_3$ (20 mL). The mixture was stirred at 110° C. for 2 hours. The solvent was removed in vacuum. The residue was dissolved in ethyl acetate (20 mL×2) and concentrated subsequently. The resulting solid was dissolved in i-PrOH (15 mL) and benzo [d]thiazol-5-amine (950 mg, 6.33 mol) was added. The mixture was stirred at 95° C. overnight. The solvent was removed in vacuum and saturated $NaHCO_3$ solution was used to adjust pH to 8. The organic layer was extracted by ethyl acetate (100 mL) and concentrated. The residue was purified by silica gel column chromatography (dichloromethane/methane (v/v)=20/1) to give the desired product (950 mg, 35%) as a yellow solid. $^1H$ NMR (400 MHz, DMSO-$d_6$) δ 9.44 (s, 1H), 9.09 (s, 1H), 8.48 (d, J=5.6 Hz, 1H), 8.24-8.21 (m, 2H), 8.04 (d, J=2.0 Hz, 1H), 7.53 (dd, J=4.2, 2.0 Hz, 1H), 7.01 (d, J=5.6 Hz, 1H). LC-MS (m/z): 481.4 $[M+H]^+$.

Step f. (4-(benzo[d]thiazol-5-ylamino)-7-bromoquinolin-6-yl)dimethylphosphine oxide: To a solution of N-(7-bromo-6-iodoquinolin-4-yl)benzo[d]thiazol-5-amine (800 mg, 1.60 mmol) in 1,4-dioxane (10 mL) was added $Pd_2dba_3$ (73 mg, 0.08 mmol), Xantphos (93 mg, 0.16 mmol), dimethylphosphine oxide (187 mg, 2.40 mmol) and $Et_3N$ (323 mg, 3.20 mmol). The mixture was stirred at 70° C. overnight under $N_2$ atmosphere. The solvent was removed in vacuum and the resulting residue was purified by silica gel column chromatography (dichloromethane/methanol (v/v)=50/1) to yield the corresponding product (240 mg, 33%) as a yellow solid. $^1H$ NMR (400 MHz, DMSO-$d_6$) δ 11.52 (s, 1H), 9.53 (s, 1H), 9.18 (d, J=12.8 Hz, 1H), 8.55 (d, J=6.8 Hz, 1H), 8.42-8.31 (m, 2H), 8.19 (s, 1H), 7.59 (d, J=8.4 Hz, 1H), 6.92 (d, J=6.4 Hz, 1H), 2.00 (s, 3H), 1.96 (s, 3H). LC-MS (m/z): 432.0 $[M+H]^+$.

Step g. (4-(benzo[d]thiazol-5-ylamino)-7-(1-methyl-1H-pyrazol-4-yl)quinolin-6-yl)dimethylphosphine oxide: To a solution of (4-(benzo[d]thiazol-5-ylamino)-7-bromoquinolin-6-yl)dimethylphosphine oxide in 1,4-dioxane/$H_2O$ (10.0 mL/0.5 mL) was added Pd(dppf)$Cl_2$ (10 mg, 0.014 mmol), (1-methyl-1H-pyrazol-4-yl)boronic acid (35 mg, 0.28 mmol) and $K_2CO_3$ (40 mg, 0.28 mmol). The mixture was stirred at 100° C. overnight under $N_2$ atmosphere. The solvent was removed in vacuum and the resulting residue was purified by silica gel column chromatography (dichloromethane/methanol (v/v)=10/1) to give the desired product (10 mg, 17%) as a green solid.

EXAMPLE 6, METHOD F

Preparation of (S)-(4-(benzo[d]thiazol-5-ylamino)-7-(2,3-dihydroxypropoxy)quinolin-6-yl)dimethylphosphine oxide (A18)

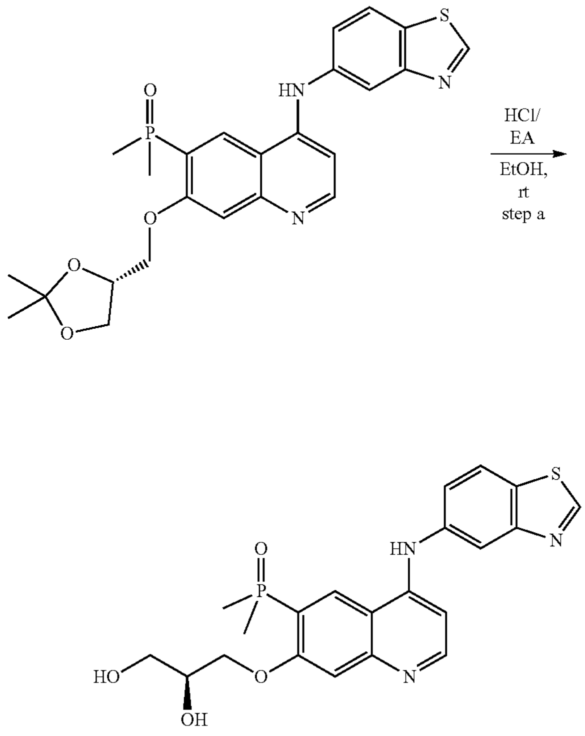 [SMILES: CC1(C)OC[C@@H](COc2cc3nccc(Nc4ccc5scnc5c4)c3cc2P(C)(C)=O)O1 ; CP(C)(=O)c1cc2c(Nc3ccc4scnc4c3)ccnc2cc1OC[C@@H](O)CO]

Step a. (S)-(4-(benzo[d]thiazol-5-ylamino)-7-(2,3-dihydroxypropoxy)quinolin-6-yl)dimethylphosphine oxide: To a solution of (R)-(4-(benzo[d]thiazol-5-ylamino)-7-((2,2-dimethyl-1,3-dioxolan-4-yl)methoxy)quinolin-6-yl)dimethylphosphine oxide (120 mg, 0.25 mmol) in ethanol (5 mL) was added 3N HCl in ethyl acetate (2 mL). The mixture was stirred at room temperature for 2 hours. The solvent was removed and the residue was dissolved in dichloromethane/methanol (20 mL/10 mL). Saturated $NaHCO_3$ was added to adjust pH to ~7. The solvent was concentrated and residue was purified by $^{18}$C column chromatography (water/methanol (v/v)= 60/40) to give the desired product (90 mg, 82%) a yellow solid.

EXAMPLE 7, METHOD G

Preparation of (4-(benzo[d]thiazol-5-ylamino)-3-fluoro-7-methoxyquinolin-6-yl)dimethylphosphine oxide (A23)

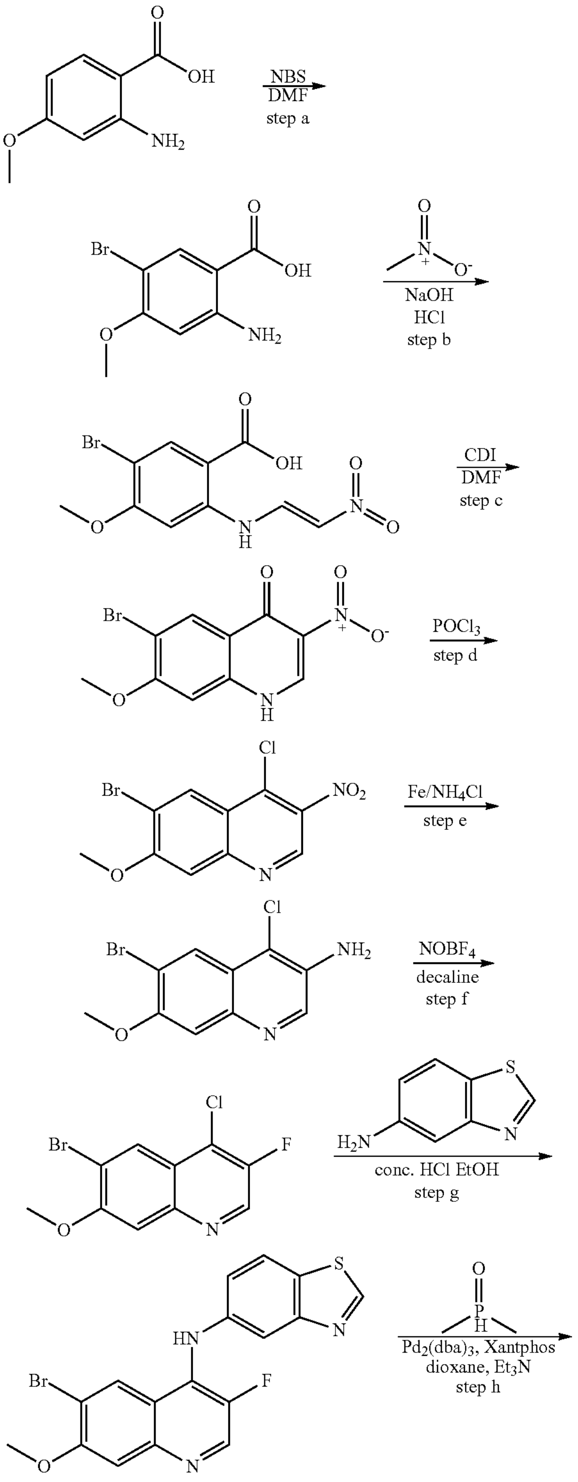

-continued

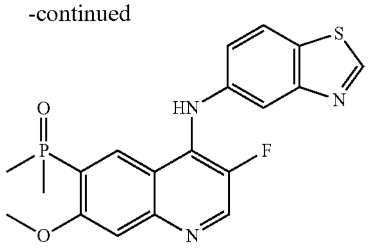

Step a. 2-amino-5-bromo-4-methoxybenzoic acid: To a solution of 2-amino-4-methoxybenzoic acid (15.0 g, 89.7 mmol) in N,N-dimethylformamide (50 mL) was added NBS (16.0 g, 89.7 mmol) slowly at 0° C. The mixture was stirred at room temperature for an hour. The solvent was concentrated and the resulting solid was rinsed by ethyl acetate/petroleum ether (200 mL/400 mL) to give the desired product as a grey solid (18.0 g, 82%). $^1$H NMR (400 MHz, DMSO-$d_6$) δ 7.76 (s, 1H), 6.41 (s, 1H), 3.79 (s, 3H). LC-MS (m/z): 246.0 $[M+H]^+$.

Step b. 5-bromo-4-methoxy-2-((2-nitrovinyl)amino)benzoic acid: To a solution of NaOH (53.9 g, 1347.5 mmol) in water (50 mL) was added nitromethane (21.9 g, 359.2 mmol). The mixture was stirred at 45° C. for 5 minutes. Additional nitromethane (21.9 g, 359.2 mmol) was added at room temperature. The mixture was stirred for 10 minutes at room temperature and 5 minutes at 50° C. The solvent was poured into ice (500 g) and adjusted pH to ~2 with concentrated HCl. This solvent was added to water (300 mL) including 2-amino-5-bromo-4-methoxybenzoic acid (22.0 g, 89.8 mmol). Conc. HCl (161.5 mL) was added to the solution and the mixture was stirred overnight. The resulting solid was collected by filtration, dried in vacuum to give the desired product (24.0 g, 85%) as a yellow solid. $^1$H NMR (300 MHz, DMSO-$d_6$) δ 13.07 (d, J=13.5 Hz, 1H), 8.19 (dd, J=13.2, 6.3 Hz, 1H), 8.09 (s, 1H), 7.35 (s, 1H), 6.82 (d, J=6.3 Hz, 1H), 3.99 (s, 3H). LC-MS (m/z): 314.9 $[M-H]^-$.

Step c. 6-bromo-7-methoxy-3-nitroquinolin-4(1H)-one: To solution of 5-bromo-4-methoxy-2-((2-nitrovinyl)amino)benzoic acid (2.0 g, 6.3 mmol) in N,N-dimethylformamide (300 mL) was added CDI (1.5 g, 9.45 mmol). The mixture was stirred at 60° C. overnight. The solvent was removed in vacuum and the resulting solid was rinsed with acetonitrile (300 mL) to give the desired product (1.4 g, 72%) as a brown solid. $^1$H NMR (300 MHz, DMSO-$d_6$) δ 8.58 (s, 1H), 7.76 (s, 1H), 6.67 (s, 1H), 6.64 (s, 1H), 3.42 (s, 3H). LC-MS (m/z): 299.0 $[M+H]^+$.

Step d. 6-bromo-4-chloro-7-methoxy-3-nitroquinoline: To a solution of 6-bromo-7-methoxy-3-nitroquinolin-4(1H)-one (14.0 g, 46.9 mmol) in $POCl_3$ (100 mL) was added N,N-dimethylformamide (2 mL). The mixture was stirred at 110° C. overnight. $POCl_3$ was removed in vacuum. The residue was dissolved in dichloromethane/water (100 mL/100 mL) and stirred for 30 minutes. The organic layer was separated and the aqueous phase was extracted with dichloromethane (200 mL×2). The organic layer was combined, dried over $Na_2SO_4$ and purified by silica gel column chromatography (dichloromethane) to give the desired product (3.36 g, 23%) as a white solid. $^1$H NMR (300 MHz, $CDCl_3$) δ 9.25 (s, 1H), 8.64 (s, 1H), 7.51 (s, 1H), 4.11 (s, 3H).

Step e. 6-bromo-4-chloro-7-methoxyquinolin-3-amine: To a solution of 6-bromo-4-chloro-7-methoxy-3-nitroquinoline (3.4 g, 10.6 mmol) in i-PrOH/$H_2O$ (100 mL/25 mL) was added iron powder (3.0 g, 53.2 mmol) and $NH_4Cl$ (2.8 g, 53.2 mmol). The mixture was stirred at 75° C. for 2 hours. The solvent was filtered through diatomaceous earth. The filtrate was extracted by dichloromethane (100 mL×3). The organic layer was combined, dried over $Na_2SO_4$ and concentrated. The residue was purified by silica gel column chromatography (petroleum ether/ethyl acetate (v/v)=2/1) to give the desired product as a brown solid (2.5 g, 86%). $^1$H NMR (300 MHz, DMSO-$d_6$) δ 8.54 (s, 1H), 8.04 (s, 1H), 7.41 (s, 1H), 5.96 (s, 2H), 3.94 (s, 3H). LC-MS (m/z): 287.0 $[M+H]^+$.

Step f. 6-bromo-4-chloro-3-fluoro-7-methoxyquinoline: To a solution of 6-bromo-4-chloro-7-methoxyquinolin-3-amine (2.5 g, 8.74 mmol) in dry tetrahydrofuran (20 mL) was added Nitrosonium tetrafluoroborate (1.1 g, 9.42 mmol) at −10° C. The mixture was stirred at 0° C. for 50 minutes. The resulting solid was filtered and dissolved in decahydronaphthalene. The mixture was stirred at 170° C. for 5 minutes. The solvent was removed and the residue was purified by silica gel column chromatography (petroleum ether/ethyl acetate (v/v)=4/1) to give the desired product (435 mg, 17%) as a white solid. $^1$H NMR (300 MHz, $CDCl_3$) δ 8.76 (s, 1H), 8.39 (s, 1H), 7.46 (s, 1H), 4.05 (s, 3H). LC-MS (m/z): 289.9 $[M+H]^+$.

Step g. N-(6-bromo-3-fluoro-7-methoxyquinolin-4-yl)benzo[d]thiazol-5-amine: To a solution of 6-bromo-4-chloro-3-fluoro-7-methoxyquinoline (435 mg, 1.5 mmol) in ethanol (30 mL) was added benzo[d]thiazol-5-amine (225 mg, 1.5 mmol) and conc. HCl (one drop). The mixture was stirred at 85° C. for 2 hours. The solvent was removed in vacuum and the residue was purified by silica gel column chromatography (petroleum ether/ethyl acetate (v/v)=2/1) to give the desired product (85 mg, 14%) as a white solid. $^1$H NMR (300 MHz, DMSO-$d_6$) δ 9.35 (s, 1H), 9.24 (s, 1H), 8.77 (d, J=3.3 Hz, 1H), 8.63 (s, 1H), 8.04 (d, J=8.7 Hz, 1H), 7.59 (s, 1H), 7.50 (s, 1H), 7.23 (d, J=7.5 Hz, 1H), 4.01 (s, 3H). LC-MS (m/z): 403.9 $[M+H]^+$.

Step h. (4-(benzo[d]thiazol-5-ylamino)-3-fluoro-7-methoxyquinolin-6-yl)dimethylphosphine oxide: To a solution of N-(6-bromo-3-fluoro-7-methoxyquinolin-4-yl)benzo[d]thiazol-5-amine (90 mg, 0.22 mmol) in 1,4-dioxane (3 mL) was added dimethylphosphine oxide (19 mg, 0.24 mmol), $Pd_2(dba)_3$ (20 mg, 0.02 mmol), Xantphos (13 mg, 0.02 mmol) and $Et_3N$ (45 mg, 0.12 mmol). The mixture was stirred at 125° C. through microwave irritation under $N_2$ atmosphere for 2 hours. The reaction was concentrated and the resulting solid was purified by silica gel column chromatography (dichloromethane/methanol (v/v)=20/1) to give a crude product. The solid was rinsed by ethyl acetate/ether (1 mL/4 mL) to give the desired product (14 mg, 16%) as a yellow solid.

EXAMPLE 8, METHOD H

Preparation of (4-(benzo[d]thiazol-5-ylamino)-7-(oxetan-3-yl)quinolin-6-yl)dimethylphosphine oxide (A26)

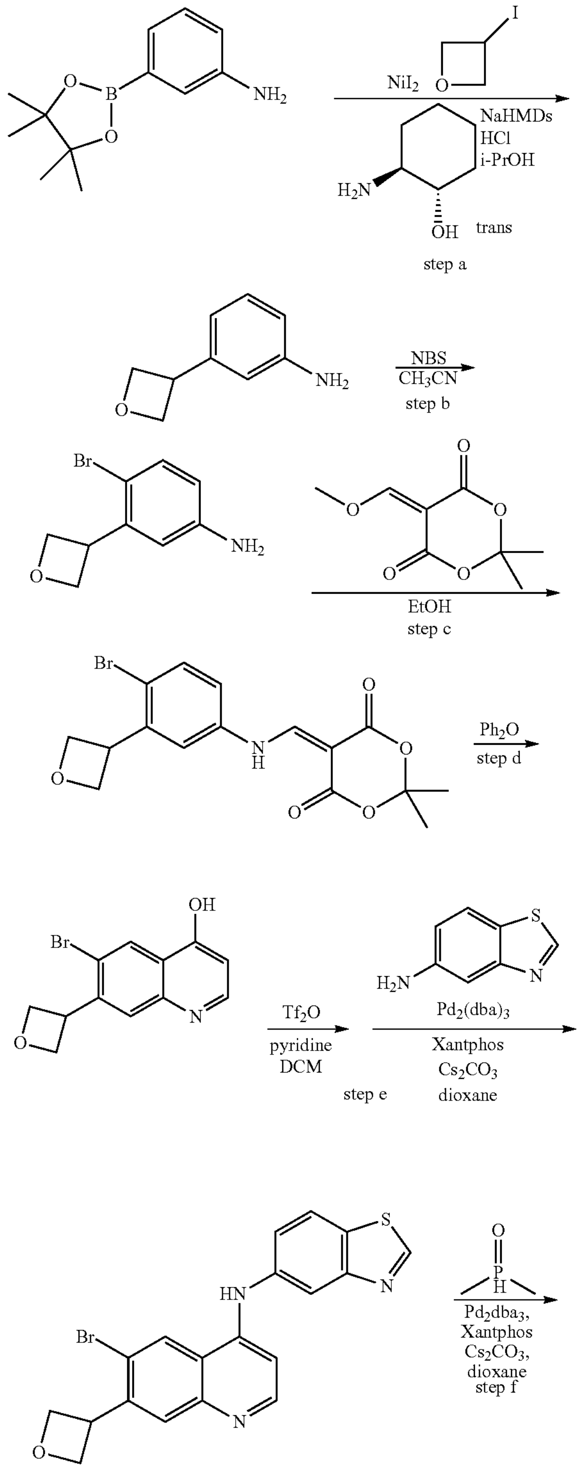

-continued

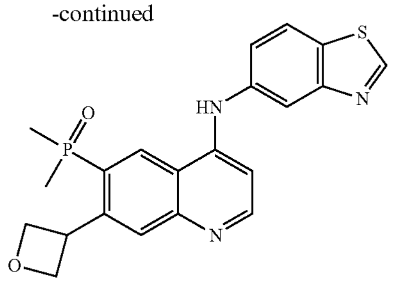

Step a. 3-(oxetan-3-yl)aniline 3-(4,4,5,5-tetramethyl-1,3,2-dioxaborolan-2-yl)aniline (4.0 g, 18.3 mmol), $NiI_2$ (562 mg, 1.8 mmol) and trans-2-Aminocyclohexanol hydrochloride (274 mg, 1.8 mmol) were added to a microwave tube followed by addition of NaHMDs (9.15 mL, 18.3 mmol) and dry i-PrOH (20 mL). The mixture was stirred at room temperature under $N_2$ atmosphere for 10 minutes. 3-iodooxetane (3.4 g, 18.3 mmol) was added and the reaction was stirred at 120° C. under microwave irritation under $N_2$ atmosphere for 2 hours. The reaction was quenched by water and organic layer was extracted by dichloromethane (50 mL×2). The organic layer was combined, dried over $Na_2SO_4$ and concentrated. The residue was purified by silica gel column chromatography (petroleum ether/ethyl acetate (v/v)=4/1) to give the desired product (1.01 g, 37%) as a yellow oil. $^1$H NMR (300 MHz, $CDCl_3$) δ 7.21-7.09 (m, 1H), 6.81-6.71 (m, 2H), 6.60 (d, J=8.7 Hz, 1H), 5.04 (dd, J=8.4, 6.0 Hz, 2H), 4.76 (t, J=6.3 Hz, 2H), 4.21-4.06 (m, 1H), 3.70 (s, 2H). LC-MS (m/z): 150.1 $[M+H]^+$.

Step b. 4-bromo-3-(oxetan-3-yl)aniline: To a solution of 3-(oxetan-3-yl)aniline (1.01 g, 6.7 mmol) in acetonitrile (15 mL) was added NBS (961 mg, 5.4 mmol) in acetonitrile (5 mL) at 0° C. The mixture was stirred for 30 minutes at this temperature. The solvent was concentrated and the residue was purified by silica gel column chromatography (petroleum ether/ethyl acetate (v/v)=4/1) to give the desired product (913 mg, 60%) as a white solid. $^1$H NMR (300 MHz, $CDCl_3$) δ 7.31-7.24 (m, 1H), 6.78 (d, J=2.4 Hz, 1H), 6.47 (dd, J=8.7, 2.7 Hz, 1H), 5.05 (dd, J=7.8, 6.0 Hz, 2H), 4.77 (t, J=6.6 Hz, 2H), 4.59-4.45 (m, 1H), 3.77 (s, 2H). LC-MS (m/z): 228.0 $[M+H]^+$.

Step c. 5-4(4-bromo-3-(oxetan-3-yl)phenyl)amino)methylene)-2,2-dimethyl-1,3-dioxane-4,6-dione: To a solution of 4-bromo-3-(oxetan-3-yl)aniline (913 mg, 4.0 mmol) in ethanol (8 mL) was added 5-(methoxymethylene)-2,2-dimethyl-1,3-dioxane-4,6-dione (893 mg, 4.8 mmol). The mixture was stirred at room temperature for 30 minutes. The resulting solid was filtered, washed with ethanol and dried in vacuum to give the desired product (1.18 g, 77%) as a yellow solid. $^1$H NMR (300 MHz, $CDCl_3$) δ 11.28 (d, J=14.4 Hz, 1H), 8.63 (d, J=14.0 Hz, 1H), 7.61 (d, J=8.3 Hz, 1H), 7.31-7.27 (m, 1H), 7.12-7.02 (m, 1H), 5.17-5.07 (m, 2H), 4.84-4.74 (m, 2H), 4.67-4.52 (m, 1H), 1.60 (s, 6H).

Step d. 6-bromo-7-(oxetan-3-yl)quinolin-4-ol: The diphenyl ether (30 mL) was added to a round-bottomed flask and the solvent was heated to 240° C. for 20 minutes. Intermediate 5-(((4-bromo-3-(oxetan-3-yl)phenyl)amino)methylene)-2,2-dimethyl-1,3-dioxane-4,6-dione (1.18 g, 3.1 mmol) was added slowly to the solution. The mixture was stirred for 2 minutes. After cooling to room temperature, The resulting solid was filtered, washed with ether and dried in vacuum to give the desired product (490 mg, 56%) as a yellow solid. $^1H$ NMR (300 MHz, DMSO-$d_6$) δ 11.80 (s, 1H), 8.19 (s, 1H), 7.96 (d, J=6.9 Hz, 1H), 7.64 (s, 1H), 6.07 (d, J=7.5 Hz, 1H), 5.11-4.93 (m, 2H), 4.68 (t, J=6.3 Hz, 2H), 4.63-4.47 (m, 1H). LC-MS (m/z): 280.0 $[M+H]^+$.

Step e: N-(6-bromo-7-(oxetan-3-yl)quinolin-4-yl)benzo[d]thiazol-5-amine: To a solution 6-bromo-7-(oxetan-3-yl)quinolin-4-ol (250 mg, 0.89 mmol) in dichloromethane (4 mL) was added pyridine (703 mg, 8.9 mmol) and $(CF_3SO_2)_2O$ (1.25 g, 4.45 mmol) dropwise at 0° C. The mixture was stirred at room temperature for 30 minutes. The solvent was concentrated and the residue was dissolved in dry 1,4-dioxane (4 mL). benzo[d]thiazol-5-amine (161 mg, 1.07 mmol), $Pd_2dba_3$ (82 mg, 0.09 mmol), Xantphos (52 mg, 0.09 mmol) and $Cs_2CO_3$ (870 mg, 2.67 mmol) were added to the solution. The mixture was stirred at 100° C. for 10 minutes. The solvent was concentrated and the residue was purified by silica gel column chromatography (dichloromethane/methanol (v/v)=20/1) to give the desired product as a grey solid (130 mg, 35%). $^1H$ NMR (300 MHz, DMSO-$d_6$) δ 9.43 (s, 1H), 9.30 (s, 1H), 8.77 (s, 1H), 8.51 (s, 1H), 8.20 (d, J=8.1 Hz, 1H), 8.02 (s, 1H), 7.94 (s, 1H), 7.53 (d, J=7.5 Hz, 1H), 7.02 (s, 1H), 5.11-4.96 (m, 2H), 4.90-4.73 (m, 2H), 4.71-4.53 (m, 1H). LC-MS (m/z): 412.0 $[M+H]^+$ Step f. (4-(benzo[d]thiazol-5-ylamino)-7-(oxetan-3-yl)quinolin-6-yl)dimethylphosphine oxide: To a solution N-(6-bromo-7-(oxetan-3-yl)quinolin-4-yl)benzo[d]thiazol-5-amine (120 mg, 0.29 mmol) in 1,4-dioxane (4 mL) was added dimethylphosphine oxide (45 mg, 0.58 mmol), $Cs_2CO_3$ (284 mg, 0.87 mmol), $Pd_2dba_3$ (27 mg, 0.03 mmol), Xantphos (17 mg, 0.03 mmol). The mixture was stirred at 130° C. under microwave irritation for 2.5 hours. The solvent was removed in vacuum and the residue was purified by silica gel column chromatography (dichloromethane/methanol (v/v)=100/9) to give the desired product (200 mg, 17%) as a yellow solid.

EXAMPLE 9, METHOD I

Preparation of (5-(benzo[d]thiazol-5-ylamino)-1,8-naphthyridin-3-yl)dimethylphosphine oxide (B1)

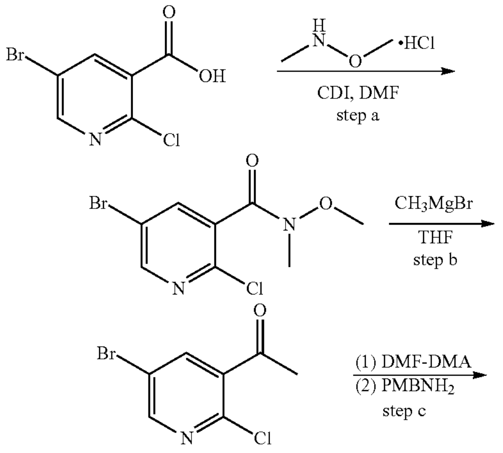

-continued

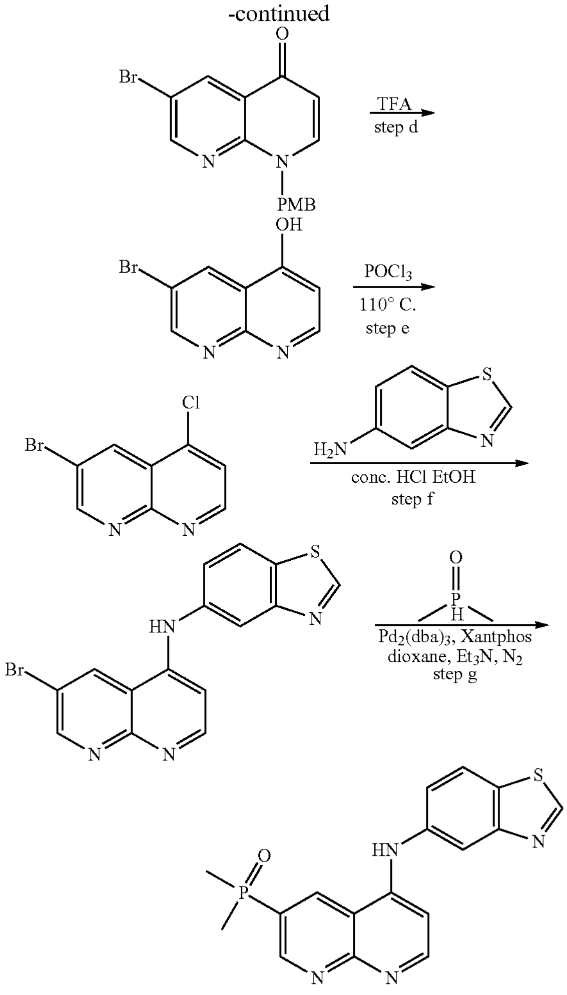

Step a. 5-bromo-2-chloro-N-methoxy-N-methylnicotinamide: To a solution of 5-bromo-2-chloronicotinic acid (3.0 g, 12.7 mmol) in N,N-dimethylformamide (30 mL) was added CDI (3.1 g, 19.1 mmol). The mixture was stirred at room temperature for 1 hour. N,O-dimethylhydroxylamine hydrochloride (1.5 g, 15.3 mmol) and $Et_3N$ (1.9 g, 19.1 mmol) were added and the mixture was stirred for another 5 hours. Ethyl acetate (100 mL) was added and the organic layer was washed with saturated $NaHCO_3$ solution (400 mL×3). The organic layer was separated, dried over $Na_2SO_4$ and concentrated. The residue was purified by silica gel column chromatography (petroleum ether/ethyl acetate (v/v)=2/1) to give the desired product (3.0 g, 85%) as a yellow solid. $^1H$ NMR (400 MHz, $CDCl_3$): δ 8.50 (s, 1H), 7.80 (s, 1H), 3.52 (s, 3H), 3.39 (s, 3H). LC-MS (m/z): 279.0 $[M+H]^+$.

Step b. 1-(5-bromo-2-chloropyridin-3-yl)ethan-1-one: To a solution of 5-bromo-2-chloro-N-methoxy-N-methylnicotinamide (2.6 g, 9.3 mmol) in tetrahydrofuran (30 mL) was added methylmeganesium bromide (3.4 mL, 10.2 mmol) dropwise at 0° C. The mixture was stirred at room temperature for 2 hours. Saturated $NH_4Cl$ was used to quench the reaction and water (200 mL) was added. The organic layer was extracted by ethyl acetate (200 mL), dried over $Na_2SO_4$ and concentrated. The residue was purified by silica gel column chromatography (petroleum ether/ethyl acetate (v/v)=15/1) to give the desired product (2.0 g, 92%) as a colorless oil. $^1$H NMR (400 MHz, $CDCl_3$) δ 8.55 (s, 1H), 8.02 (s, 1H), 2.70 (s, 3H). LC-MS (m/z): 234.0 $[M+H]^+$.

Step c. 6-bromo-1-(4-methoxybenzyl)-1,8-naphthyridin-4(1H)-one: 1-(5-bromo-2-chloropyridin-3-yl)ethan-1-one (2.00 g, 8.55 mmol) was added to DMF-DMA (10 mL) and the mixture was stirred at 110° C. for 3 hours. The solvent was removed in vacuum and the residue was dissolved in N,N-dimethylformamide (10 mL). PMB-NH 2 (1.76 g, 12.82 mmol) and $Cs_2CO_3$ (5.57 g, 17.09 mmol) were added and the mixture was stirred at 110° C. overnight. Ethyl acetate (100 mL) was added and organic layer was washed with saturated NaCl solution (400 mL×3). The organic layer was separated, dried over $Na_2SO_4$ and concentrated. The residue was purified by silica gel column chromatography (dichloromethane/methanol (v/v)=120/1) to give the desired product (700 mg, 24%) as a yellow solid. $^1$H NMR (400 MHz, $CDCl_3$) δ 8.81 (d, J=2.4 Hz, 1H), 8.75 (d, J=2.4 Hz, 1H), 7.72 (d, J=8.0 Hz, 1H), 7.23-7.20 (m, 2H), 6.87-6.85 (m, 2H), 6.33 (d, J=7.6 Hz, 1H), 5.48 (s, 2H), 3.78 (s, 3H). LC-MS (m/z): 345.1 $[M+H]^+$.

Step d. 6-bromo-1,8-naphthyridin-4-ol: 6-bromo-1-(4-methoxybenzyl)-1,8-naphthyridin-4(1H)-one (700 mg, 0.03 mmol) was added to TFA (2 mL). The mixture was stirred at 110° C. through microwave irritation for 2 hours. The solvent was removed and saturated $NaHCO_3$ was used to adjust pH to 7. Water (100 mL) was added. Organic layer was extracted by dichloromethane/methanol (50 mL/10 mL), dried over $Na_2SO_4$ and concentrated. The residue was purified by silica gel column chromatography (dichloromethane/methane (v/v)=50/1) to give the desired product (320 mg, 70%) as a yellow solid. $^1$H NMR (400 MHz, DMSO-$d_6$) δ 12.37 (s, 1H), 8.85 (s, 1H), 8.53 (s, 1H), 8.02-7.96 (m, 1H), 6.15 (d, J=6.8 Hz, 1H). LC-MS (m/z): 224.9 $[M+H]^+$.

Step e. 3-bromo-5-chloro-1,8-naphthyridine: 6-bromo-1,8-naphthyridin-4-ol (300 mg, 1.33 mmol) was added to $POCl_3$ (4 mL). The mixture was stirred at 110° C. for 1 hour. The solvent was removed in vacuum to give the desired crude product (350 mg) as a brown solid.

Step f. N-(6-bromo-1,8-naphthyridin-4-yl)benzo[d]thiazol-5-amine: To a solution of 3-bromo-5-chloro-1,8-naphthyridine (350 mg, 1.44 mmol) in ethanol (3 mL) was added benzo[d]thiazol-5-amine (237 mg, 1.58 mmol) and conc. HCl (one drop). The mixture was stirred at 80° C. for 3 hours. Water (30 mL) was added and saturated $NaHCO_3$ was used to adjust pH to ~7. The organic layer was extracted by dichloromethane/methane (30 mL/10 mL×2), combined, dried over $Na_2SO_4$ and concentrated. The residue was purified by silica gel column chromatography (dichloromethane/methane (v/v)=30/1) to give the desired product (105 mg, 20%) as a yellow solid. $^1$H NMR (400 MHz, DMSO-$d_6$) δ 11.78 (s, 1H), 9.81 (s, 1H), 9.55 (s, 1H), 9.28 (s, 1H), 8.55 (d, J=5.6 Hz, 1H), 8.40 (d, J=8.0 Hz, 1H), 8.22 (s, 1H), 7.62 (d, J=8.4 Hz, 1H), 6.96 (d, J=6.4 Hz, 1H). LC-MS (m/z): 357.0 $[M+H]^+$.

Step g. (5-(benzo[d]thiazol-5-ylamino)-1,8-naphthyridin-3-yl)dimethylphosphine oxide: To a solution of N-(6-bromo-1,8-naphthyridin-4-yl)benzo[d]thiazol-5-amine (105 mg, 0.29 mmol) in 1,4-dioxane (4 mL) was added dimethylphosphine oxide (34 mg, 0.44 mmol), $Et_3N$ (45 mg, 0.44 mmol), Pd 2 dba 3 (27 mg, 0.03 mmol) and Xantphos (17 mg, 0.03 mmol). The mixture was stirred at 125° C. under microwave irritation for 2 hours. Saturated $NaHCO_3$ solution was added to the solution and the solvent was stirred for another 30 minutes. The solvent was removed in vacuum and the residue was purified by silica gel column chromatography (dichloromethane/methanol (v/v)=20/1) to give the desired product (10 mg, 10%).

EXAMPLE 10, METHOD J

Preparation of (4-(benzo[d]thiazol-5-ylamino)-7-methoxycinnolin-6-yl)dimethylphosphine oxide (B2)

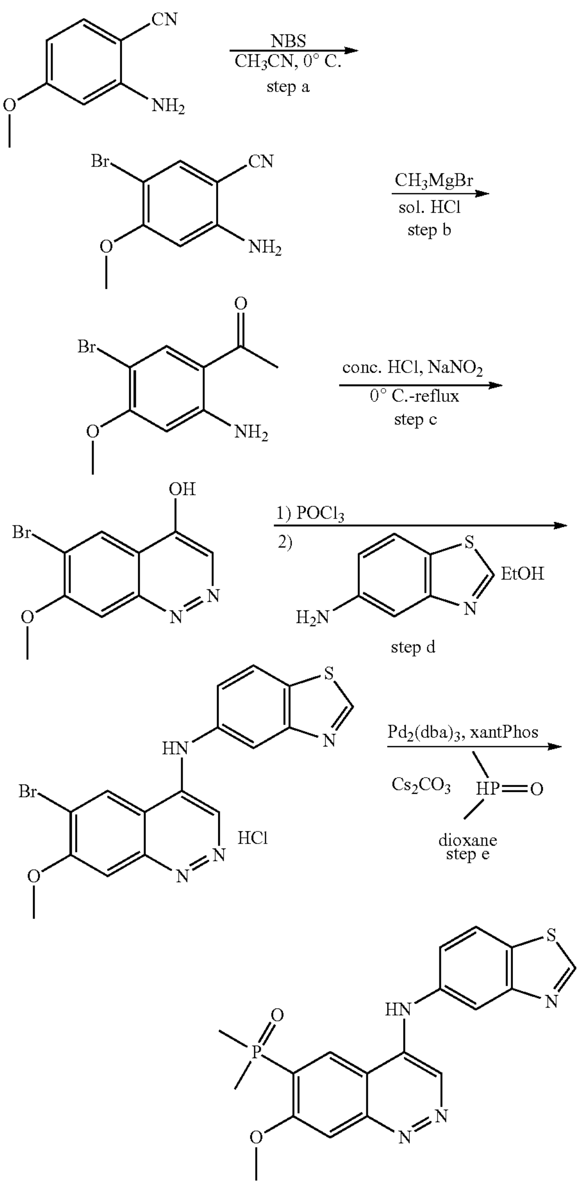

Step a. 2-amino-5-bromo-4-methoxybenzonitrile: To a solution of 2-amino-4-methoxybenzonitrile (2.0 g, 13.5 mmol) in acetonitrile (30 mL) was added NBS (2.7 g, 14.9 mmol) in acetonitrile (10 mL) at 0° C. The mixture was stirred at room temperature for 30 minutes. The solvent was concentrated and the residue was purified by silica gel column chromatography (petroleum ether/ethyl acetate (v/v)=10/1) to give the desired product (2.5 g, 82%) as a yellow solid. $^1$H NMR (400 MHz, $CDCl_3$) δ 7.52 (s, 1H), 6.23 (s, 1H), 4.48 (s, 2H), 3.89 (s, 3H). LC-MS (m/z): 228.0 $[M+H]^+$.

Step b. 1-(2-amino-5-bromo-4-methoxyphenyl)ethan-1-one: Methylmagnesium bromide (20.5, 61.5 mmol) was added to a two-necked bottle. 2-amino-5-bromo-4-methoxybenzonitrile in tetrahydropyran (10 mL) was added dropwise to the solution at 0° C. The mixture was stirred at room temperature for 5 minutes under $N_2$ atmosphere and 55° C. for another 16 hours. 6N HCl solution was added to the reaction and stirred at room temperature for 50 minutes. Saturated $NaHCO_3$ solution was used to neutralize HCl. The organic layer was extracted by dichloromethane (50 mL×3), combined, dried over $Na_2SO_4$ and concentrated. The residue was purified by silica gel column chromatography (petroleum ether/ethyl acetate (v/v)=5/1) to give the desired product (700 mg, 33%) as a grey solid. $^1$H NMR (400 MHz, $CDCl_3$) δ 7.83 (s, 1H), 6.45 (s, 2H), 6.08 (s, 1H), 3.87 (s, 3H), 2.51 (s, 3H). LC-MS (m/z): 244.0 $[M+H]^+$.

Step c. 6-bromo-7-methoxycinnolin-4-ol: 1-(2-amino-5-bromo-4-methoxyphenyl)ethan-1-one (700 mg, 2.9 mmol) was added to conc. HCl (10 mL) at 0° C. and stirred at this temperature for 15 minutes. $NaNO_2$ (221 mg, 3.2 mmol) in water (1 mL) was added to the solution and the mixture was stirred at 0° C. for 1.5 hours, room temperature overnight and reflux for 6 hours. Saturated $NaHCO_3$ solution was used to neutralize HCl. The organic layer was extracted by dichloromethane/methane (35 mL/7 mL×5), dried over $Na_2SO_4$ and concentrated. The residue was purified by silica gel column chromatography (dichloromethane/methane (v/v)=50/1) to give the desired product (350 mg, 69%) as a white solid. $^1$H NMR (400 MHz, DMSO-$d_6$) δ 13.43 (s, 1H), 8.15 (s, 1H), 7.73 (s, 1H), 7.01 (s, 1H), 3.98 (s, 3H). LC-MS (m/z): 255.0 $[M+H]^+$.

Step d. N-(6-bromo-7-methoxycinnolin-4-yl)benzo[d]thiazol-5-amine hydrochloride: 6-bromo-7-methoxycinnolin-4-ol (350 mg, 1.4 mmol) was added to $POCl_3$ (4 mL). The mixture was stirred at 110° C. for 2 hours. The solvent was concentrated and dissolved in ethanol (5 mL). Benzo[d]thiazol-5-amine (225 mg, 1.5 mmol) was added to the reaction and the mixture was stirred at 80° C. for 2 hours. The resulting solid was collected by filtration, washed with ethanol and dried in vacuum to give the desired product (290 mg, 54%) as a yellow solid hydrochloride.

$^1$H NMR (400 MHz, DMSO-$d_6$) δ 15.79 (s, 1H), 12.18 (s, 1H), 9.54 (s, 1H), 9.37 (d, J=10.4 Hz, 1H), 8.54 (s, 1H), 8.39 (d, J=8.0 Hz, 1H), 8.30 (s, 1H), 7.68 (d, J=8.4 Hz, 1H), 7.54 (d, J=6.4 Hz, 1H), 4.11 (s, 3H). LC-MS (m/z): 386.9 $[M+H]^+$.

Step e. (4-(benzo[d]thiazol-5-ylamino)-7-methoxycinnolin-6-yl)dimethylphosphine oxide: To a solution of N-(6-bromo-7-methoxycinnolin-4-yl)benzo[d]thiazol-5-amine hydrochloride (130 mg, 0.34 mmol) in 1,4-dioxane (4 mL) was added dimethylphosphine oxide (52 mg, 0.68 mmol), $Et_3N$ (103 mg, 1.02 mmol), $Pd_2dba_3$ (31 mg, 0.03 mmol) and Xantphos (17 mg, 0.03 mmol). The mixture was stirred at 120° C. under microwave irritation for 4 hours. Saturated $NaHCO_3$ solution was added to the solution and the solvent was stirred for another 30 minutes. The solvent was removed in vacuum and the residue was purified by silica gel column chromatography (dichloromethane/methanol (v/v)=20/1) to yield a crude product. Which was rinsed by ethanol/ether (1 mL/5 mL) to give the desired product (25 mg, 19%) as a yellow solid.

Table 1 shows a selection of the compounds prepared according to the methods discussed above in details and indicated in the third column of the table.

TABLE 1

Selected compounds (A1-A29, B1-B2) of the present invention.

| NO. | Structure | Method | $^1$HNMR&LC-MS |
|---|---|---|---|
| A1 | 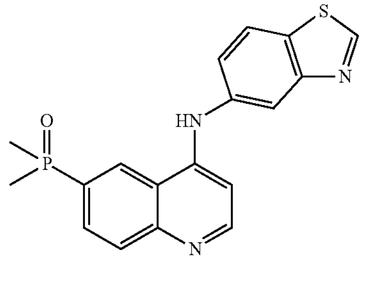 [SMILES: CP(C)(=O)c1ccc2nccc(Nc3ccc4scnc4c3)c2c1] | C | $^1$H NMR (400 MHz, DMSO-$d_6$) δ 9.51 (s, 1H), 9.44 (s, 1H), 8.84 (d, J = 13.2 Hz, 1H), 8.53 (s, 1H), 8.22 (d, J = 8.0 Hz, 1H), 8.05 (s, 1H), 8.03-7.95 (m, 2H), 7.56 (d, J = 8.0 Hz, 1H), 7.02 (s, 1H), 1.79 (s, 3H), 1.76 (s, 3H). LC-MS m/z: 354.1 $[M + H]^+$. |
| A2 | 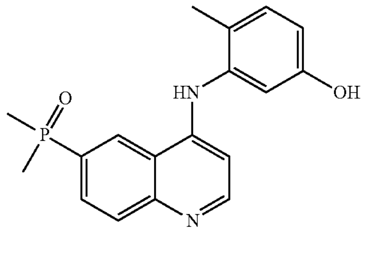 [SMILES: Cc1ccc(O)cc1Nc1ccnc2ccc(P(C)(C)=O)cc12] | C | $^1$H NMR (400 MHz, DMSO-$d_6$) δ 9.08 (s, 1H), 8.85 (d, J = J = 13.6 Hz,1H), 8.41 (d, J = 5.2 Hz, 1H), 8.01-7.91 (m, 2H), 7.16 (d, J = 8.8 Hz,1H), 6.71 (s,1H), 6.69 (s, 1H), 6.14 (d, J = 5.2 Hz, 1H), 2.04(s, 3H), 1.80 (s, 3H), 1.76 (s, 3H). LC-MS m/z: 326.9 $[M + H]^+$. |

TABLE 1-continued

Selected compounds (A1-A29, B1-B2) of the present invention.

| NO. | Structure | Method | $^1$HNMR&LC-MS |
|---|---|---|---|
| A3 | 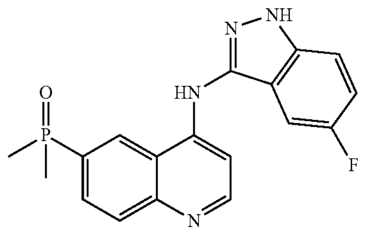 [SMILES: CP(C)(=O)c1ccc2nccc(Nc3n[nH]c4ccc(F)cc34)c2c1] | C | $^1$H NMR (400 MHz, DMSO-$d_6$): δ 13.46 (s, 1H), 11.34 (s, 1H), 9.24 (d, J = 13.6 Hz, 1H), 8.66 (d, J = 6.8 Hz, 1H), 8.35 (dd, J = 8.8 Hz, 1H), 8.13 (d, J = 8.4 Hz, 1H), 7.69 (d, J = 6 Hz, 1H), 7.60 (d, J = 8.8 Hz, 1H), 7.39 (dd, J = 8.8 Hz, 1H), 7.24 (d, J = 6.4 Hz, 1H)), 1.86 (s, 3H), 1.83 (s,3H). LC-MS m/z: 354.8 [M + H]$^+$. |
| A4 | 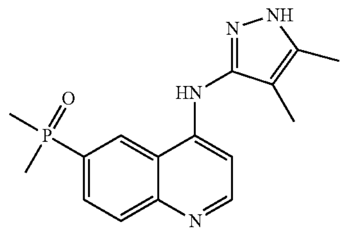 | C | $^1$H NMR (400 MHz, DMSO-$d_6$): δ 12.61 (s, 1H), 10.60 (s, 1H), 9.08 (d, J = 12.8 Hz, 1H), 8.54 (d, J = 6.4 Hz, 1H), 8.25-8.23 (m, 1H), 8.07 (d, J = 8 Hz, 1H), 6.72 (s, 1H), 2.23 (s, 3H), 1.84 (s, 3H), 1.82 (s, 3H), 1.79 (s, 3H). LC-MS m/z: 314.8 [M + H]$^+$. |
| A5 | 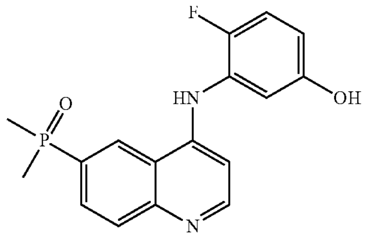 [SMILES: CP(C)(=O)c1ccc2nccc(Nc3cc(O)ccc3F)c2c1] | C | $^1$H NMR (400 MHz, DMSO-$d_6$): δ 9.25 (s, 1H), 8.85 (d, J = 12.8 Hz, 1H), 8.69 (d, J = 6 Hz, 1H), 8.47 (dd, J = 9.2 Hz, 1H), 7.94-7.95 (m, 2H), 7.12 (s, 1H), 6.83 (m, 1H), 6.67 (s, 1H), 6.42 (s, 1H), 1.76-1.77 (m, 6H). |
| A6 | 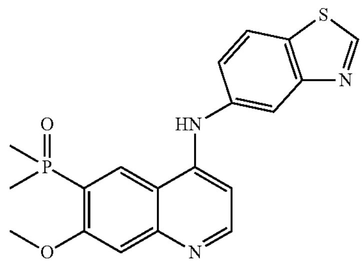 [SMILES: COc1cc2nccc(Nc3ccc4scnc4c3)c2cc1P(C)(C)=O] | C | $^1$H NMR (400 MHz, DMSO-$d_6$): δ 9.56 (s, 1H), 9.41 (s, 1H), 8.79 (d, J = 14.0 Hz, 1H), 8.46 (d, J = 4.8 Hz, 1H), 8.16 (d, J = 8.4 Hz, 1H), 8.01 (s, 1H), 7.52 (d, J = 8.4 Hz, 1H), 7.37 (d, J = 4.0 Hz, 1H), 6.94 (d, J = 4.8 Hz, 1H), 4.00 (s, 3H), 1.75 (s, 3H), 1.72 (s, 3H). LC-MS m/z: 384.1 [M + H]$^+$. |
| A7 | 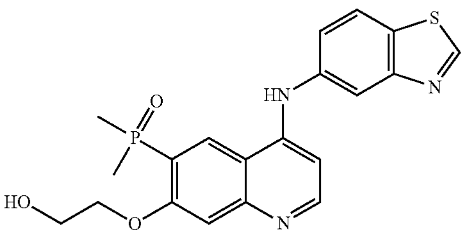 [SMILES: CP(C)(=O)c1cc2c(Nc3ccc4scnc4c3)ccnc2cc1OCCO] | D | $^1$H NMR (400 MHz, DMSO-$d_6$): δ 10.30 (s, 1H), 9.46 (s, 1H), 8.91 (d, J = 14.0 Hz, 1H), 8.45 (d, J = 5.6 Hz, 1H), 8.24 (d, J = 8.4 Hz, 1H), 8.08 (s, 1H), 7.55 (d, J = 8.4 Hz, 1H), 7.38 (s, 1H), 6.88 (d, J = 5.6 Hz, 1H), 5.07 (s, 1H), 4.25 (s, 2H), 3.86 (s, 2H), 1.82 (s, 3H), 1.78 (s, 3H). LC-MS m/z: 414.1 [M + H]$^+$. |
| A8 | 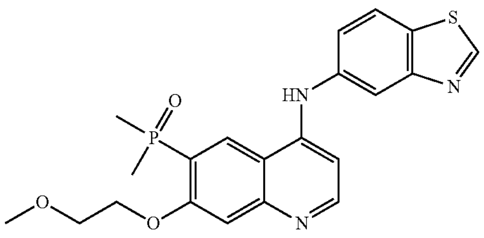 [SMILES: COCCOc1cc2nccc(Nc3ccc4scnc4c3)c2cc1P(C)(C)=O] | D | $^1$H NMR (400 MHz, DMSO-$d_6$): δ 9.72 (s, 1H), 9.42 (s, 1H), 8.83 (d, J = 14.0 Hz, 1H), 8.45 (d, J = 4.0 Hz, 1H), 8.18 (d, J = 8.4 Hz, 1H), 8.02 (s, 1H), 7.53 (d, J = 8.4 Hz, 1H), 7.36 (s, 1H), 6.92 (d, J = 4.4 Hz, 1H), 4.37-4.30 (m, 2H), 3.81-3.75 (m, 2H), 3.36 (s, 3H), 1.78 (s, 3H), 1.75 (s, 3H). LC-MS m/z: 428.1 [M + H]$^+$. |

TABLE 1-continued

| NO. | Structure | Method | $^1$HNMR&LC-MS |
|---|---|---|---|
| | Selected compounds (A1-A29, B1-B2) of the present invention. | | |
| A9 | 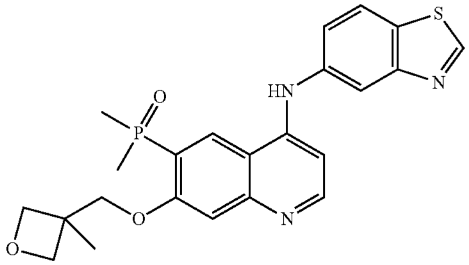 [SMILES: CC1(COc2cc3nccc(Nc4ccc5scnc5c4)c3cc2P(C)(C)=O)COC1] | D | $^1$H NMR (400 MHz, DMSO-$d_6$): δ 9.97 (s, 1H), 9.44 (s, 1H), 8.90 (d, J = 12.8 Hz, 1H), 8.46 (s, 1H), 8.20 (s, 1H), 8.05 (s, 1H), 7.53 (s, 1H), 7.45 (s, 1H), 6.91 (s, 1H), 4.63-4.52 (m, 2H), 4.45-4.36 (m, 2H), 4.34-4.27 (m, 2H), 1.79 (s, 3H), 1.76 (s, 3H), 1.45 (s, 3H). LC-MS m/z: 454.2 $[M + H]^+$. |
| A10 | 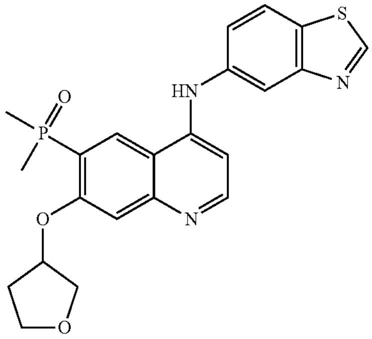 [SMILES: CP(C)(=O)c1cc2c(Nc3ccc4scnc4c3)ccnc2cc1OC1CCOC1] | B,C | $^1$H NMR (300 MHz, DMSO-$d_6$) δ 9.51 (s, 1H), 9.39 (s, 1H), 8.80 (d, J = 14.4 Hz, 1H), 8.44 (d, J = 5.4 Hz, 1H), 8.16 (d, J = 7.8 Hz, 1H), 7.99 (s, 1H), 7.51 (d, J = 8.7 Hz, 1H), 7.33 (d, J = 4.2 Hz, 1H), 6.93 (d, J = 5.7 Hz, 1H), 5.35 (s, 1H), 4.09-3.76 (m, 4H), 2.45-2.25 (m, 1H), 2.24-2.00 (m, 1H), 1.76 (d, J = 3.0 Hz, 3H), 1.72 (d, J = 3.0 Hz, 3H). LC-MS m/z: 440.1 $[M + H]^+$. |
| A11 | 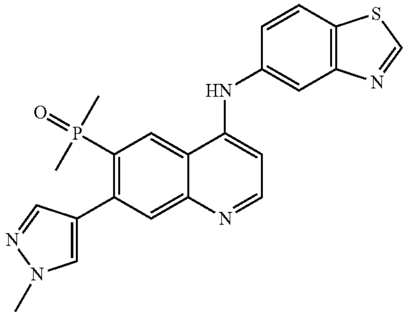 [SMILES: Cn1cc(-c2cc3nccc(Nc4ccc5scnc5c4)c3cc2P(C)(C)=O)cn1] | E | $^1$H NMR (400 MHz, DMSO-$d_6$): δ 10.09 (s, 1H), 9.48 (s, 1H), 8.80 (d, J = 14.8 Hz, 1H), 8.53 (d, J = 5.2 Hz, 1H), 8.23-8.25 (m, 2H), 8.10 (s, 1H), 7.93 (s, 1H), 7.88 (s, 1H), 7.57 (d, J = 8.4 Hz, 1H), 6.94 (d, J = 5.6 Hz, 1H), 3.95 (s, 3H), 1.66 (s, 3H), 1.63 (s, 3H). LC-MS m/z: 433.7 $[M + H]^+$. |
| A12 | 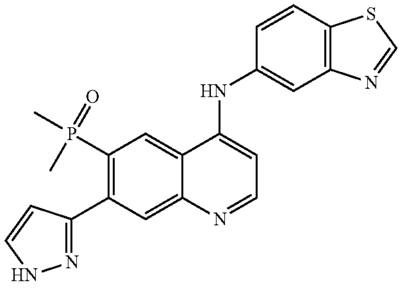 [SMILES: CP(C)(=O)c1cc2c(Nc3ccc4scnc4c3)ccnc2cc1-c1cc[nH]n1] | E | $^1$H NMR (400 MHz,DMSO-$d_6$): δ 13.30 (s,1H), 10.42 (s, 1H), 9.47 (s, 1H), 9.21 (d, J = 12.8 Hz, 1H), 8.56 (d, J = 5.2 Hz, 1H), 8.27 (d, J = 8.4 Hz, 1H), 8.12 (s, 1H), 8.03 (s, 1H), 7.96 (s, 1H), 7.59 (d, J = 8 Hz, 1H), 7.00 (d, J = 5.6 Hz, 1H), 6.75 (s, 1H), 1.63 (s, 3H), 1.62 (s, 3H). |

TABLE 1-continued

| Selected compounds (A1-A29, B1-B2) of the present invention. | | | |
|---|---|---|---|
| NO. | Structure | Method | $^1$HNMR&LC-MS |
| A13 | 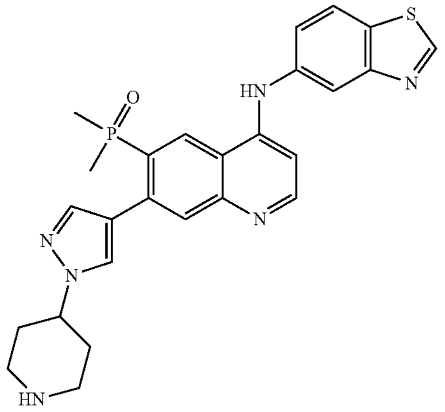 [SMILES: CP(C)(=O)c1cc2c(Nc3ccc4scnc4c3)ccnc2cc1-c1cnn(C2CCNCC2)c1] | E | $^1$H NMR (400 MHz, $CDCl_3$): δ 14.62 (s, 1H), 11.69 (s, 1H), 9.55 (s, 1H), 9.14-8.99 (m, 2H), 8.84 (s, 1H), 8.54 (s, 2H), 8.42 (d, J = 8.0 Hz, 1H), 8.25 (s, 1H), 8.07 (s, 1H), 7.99 (s, 1H), 7.64 (d, J = 8.0 Hz, 1H), 6.86 (d, J = 5.6 Hz, 1H), 4.65 (s, 1H), 3.11 (d, J = 10.1 Hz, 3H), 2.24 (s, 5H), 1.71 (s, 3H), 1.68 (s, 3H). LC-MS m/z: 502.7 $[M + H]^+$. |
| A14 | 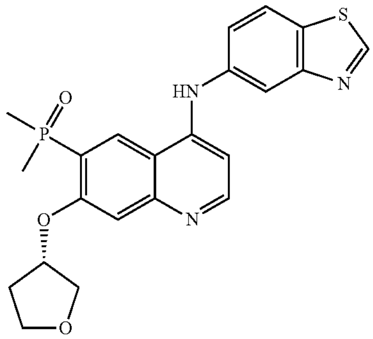 [SMILES: CP(C)(=O)c1cc2c(Nc3ccc4scnc4c3)ccnc2cc1O[C@H]1CCOC1] | B,C | $^1$H NMR (400 MHz, DMSO-$d_6$): δ 9.87 (s, 1H), 9.43 (s, 1H), 8.86 (d, J = 13.6 Hz, 1H), 8.46 (d, J = 4.8 Hz, 1H), 8.19 (d, J = 8.4 Hz, 1H), 8.03 (s, 1H), 7.53 (d, J = 8.4 Hz, 1H), 7.37 (d, J = 2.8 Hz, 1H), 6.92 (d, J = 4.8 Hz, 1H), 5.38 (s, 1H), 3.98-3.80 (m, 4H), 2.39-2.32 (m, 1H), 2.14-2.08 (m, 1H), 1.75 (d, J = 3.6 Hz, 3H), 1.72 (d, J = 3.6 Hz, 3H). LC-MS m/z: 440.1 $[M + H]^+$. |
| A15 | 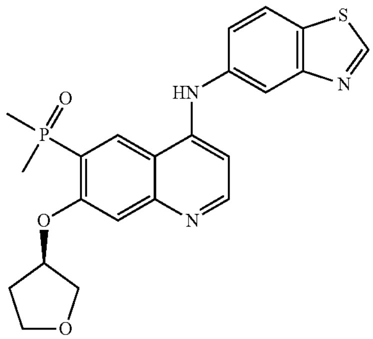 [SMILES: CP(C)(=O)c1cc2c(Nc3ccc4scnc4c3)ccnc2cc1O[C@@H]1CCOC1] | B,C | $^1$H NMR (400 MHz, DMSO-$d_6$): δ 9.78 (s, 1H), 9.42 (s, 1H), 8.86 (d, J = 14.0 Hz, 1H), 8.46 (d, J = 5.2 Hz, 1H), 8.19 (d, J = 8.4 Hz, 1H), 8.03 (s, 1H), 7.53 (d, J = 8.4 Hz, 1H), 7.36 (s, 1H), 6.92 (d, J = 5.2 Hz, 1H), 5.38 (s, 1H), 4.00-3.81 (m, 4H), 2.41-2.32 (m, 1H), 2.17-2.08 (m, 1H), 1.76 (d, J = 4.4 Hz, 3H), 1.72 (d, J = 4.4 Hz, 3H). LC-MS m/z: 440.1 $[M + H]^+$. |
| A16 | 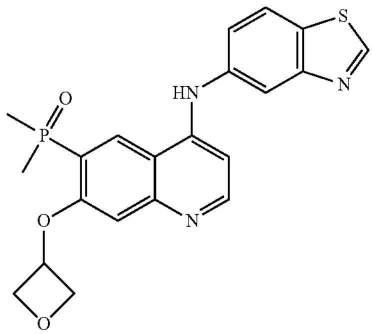 [SMILES: CP(C)(=O)c1cc2c(Nc3ccc4scnc4c3)ccnc2cc1OC1COC1] | D | $^1$H NMR (400 MHz, DMSO-$d_6$): δ 10.81 (s, 1H), 9.49 (s, 1H), 9.04 (d, J = 13.6 Hz, 1H), 8.46 (d, J = 5.6 Hz, 1H), 8.30 (d, J = 8.4 Hz, 1H), 8.12 (s, 1H), 7.55 (d, J = 7.6 Hz, 1H), 7.05 (s, 1H), 6.86 (d, J = 6.0 Hz, 1H), 5.63-5.56 (m, 1H), 5.08-5.01 (m, 2H), 4.74-4.65 (m, 2H), 1.86 (s, 3H), 1.82 (s, 3H). LC-MS m/z: 426.1 $[M + H]^+$. |

TABLE 1-continued

Selected compounds (A1-A29, B1-B2) of the present invention.

| NO. | Structure | Method | $^1$HNMR&LC-MS |
|---|---|---|---|
| A17 | 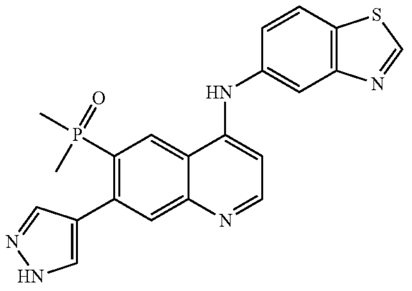 [SMILES: CP(C)(=O)c1cc2c(Nc3ccc4scnc4c3)ccnc2cc1-c1cn[nH]c1] | E | $^1$H NMR (400 MHz, DMSO-$d_6$) δ 13.27 (s, 1H), 11.04 (s, 1H), 9.50 (s, 1H), 8.98 (d, J = 14.8 Hz, 1H), 8.52 (d, J = 6.0 Hz, 1H), 8.33 (d, J = 8.4 Hz, 1H), 8.18 (s, 1H), 8.01 (s, 1H), 7.62 (d, J = 8.4 Hz, 1H), 6.90 (d, J = 6.0 Hz, 1H), 1.66 (d, J = 13.2 Hz, 6H). |
| A18 | 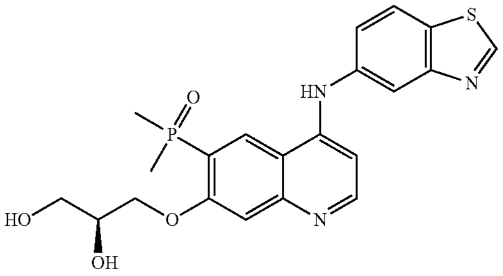 [SMILES: CP(C)(=O)c1cc2c(Nc3ccc4scnc4c3)ccnc2cc1OC[C@@H](O)CO] | D,F | $^1$H NMR (400 MHz, DMSO-$d_6$) δ 9.54 (s, 1H), 9.41 (s, 1H), 8.78 (d, J = 14.4 Hz, 1H), 8.46 (d, J = 5.6 Hz, 1H), 8.17 (d, J = 8.4 Hz, 1H), 8.01 (d, J = 2.0 Hz, 1H), 7.53 (dd, J = 8.8 Hz, J = 2.0 Hz, 1H), 7.34 (d, J = 4.8 Hz, 1H), 6.93 (d, J = 5.6 Hz, 1H), 5.32-5.07 (m, 1H), 4.96-4.77 (m, 1H), 4.30-4.23 (m, 1H), 4.16-4.10 (m, 1H), 3.96-3.89 (m, 1H), 3.55-3.48 (m, 2H), 1.79 (d, J = 14.0 Hz, 6H). LC-MS m/z: 444.1 $[M + H]^+$. |
| A19 | 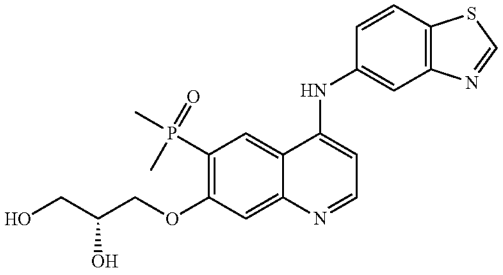 [SMILES: CP(C)(=O)c1cc2c(Nc3ccc4scnc4c3)ccnc2cc1OC[C@H](O)CO] | D,F | $^1$H NMR (400 MHz, DMSO-$d_6$) δ 9.57 (s, 1H), 9.41 (s, 1H), 8.79 (d, J = 14.4 Hz, 1H), 8.45 (d, J = 5.6 Hz, 1H), 8.16 (d, J = 8.8 Hz, 1H), 8.02 (d, J = 2.0 Hz, 1H), 7.54 (dd, J = 8.4 Hz, J = 2.0 Hz, 1H), 7.34 (d, J = 4.8 Hz, 1H), 6.93 (d, J = 5.6 Hz, 1H), 5.27-5.15 (m, 1H), 4.93-4.81 (m, 1H), 4.29-4.25 (m, 1H), 4.16-4.10 (m, 1H), 3.95-3.89 (m, 1H), 3.55-3.48 (m, 2H), 1.79 (d, J = 14.0 Hz, 6H). LC-MS m/z: 444.1 $[M + H]^+$. |
| A20 | 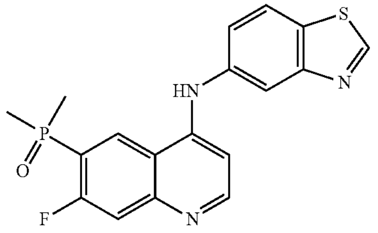 [SMILES: CP(C)(=O)c1cc2c(Nc3ccc4scnc4c3)ccnc2cc1F] | C | $^1$H NMR (300 MHz, DMSO-$d_6$) δ 9.91 (s, 1H), 9.44 (s, 1H), 8.95-8.86 (m, 1H), 8.52 (d, J = 5.1 Hz, 1H), 8.22 (d, J = 8.4 Hz, 1H), 8.05 (s, 1H), 7.71 (dd, J = 11.4, 4.2 Hz, 1H), 7.54 (d, J = 7.8 Hz, 1H), 6.98 (d, J = 5.4 Hz, 1H), 1.82 (d, J = 13.8 Hz, 6H). LC-MS m/z: 372.1 $[M + H]^+$. |
| A21 | 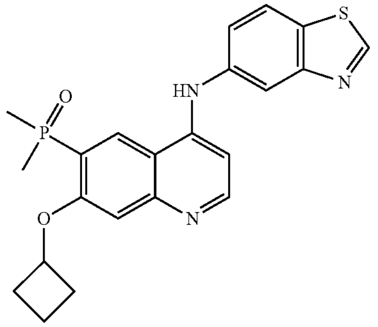 [SMILES: CP(C)(=O)c1cc2c(Nc3ccc4scnc4c3)ccnc2cc1OC1CCC1] | D | $^1$H NMR (300 MHz, DMSO-$d_6$) δ 10.42 (s, 1H), 9.46 (s, 1H), 8.94 (d, J = 13.8 Hz, 1H), 8.45 (d, J = 6.0 Hz, 1H), 8.25 (d, J = 8.4 Hz, 1H), 8.08 (s, 1H), 7.54 (d, J = 7.8 Hz, 1H), 7.27 (d, J = 4.5 Hz, 1H), 6.86 (d, J = 6.3 Hz, 1H), 5.04-4.92 (m, 1H), 2.61-2.53 (m, 2H), 2.24-2.11 (m, 2H), 1.95-1.85 (m, 1H), 1.85-1.71 (m, 7H). LC-MS m/z: 424.1 $[M + H]^+$. |

TABLE 1-continued

| Selected compounds (A1-A29, B1-B2) of the present invention. | | | |
|---|---|---|---|
| NO. | Structure | Method | $^1$HNMR&LC-MS |
| A22 | 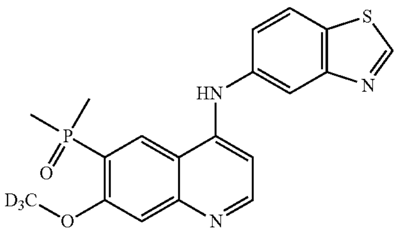 [SMILES: [2H]C([2H])([2H])Oc1cc2nccc(Nc3ccc4scnc4c3)c2cc1P(C)(C)=O] | D | $^1$H NMR (300 MHz, DMSO-$d_6$) δ 9.55 (s, 1H), 9.41 (s, 1H), 8.79 (d, J = 13.8 Hz, 1H), 8.46 (d, J = 5.4 Hz, 1H), 8.16 (d, J = 8.7 Hz, 1H), 8.01 (s, 1H), 7.53 (d, J = 8.1 Hz, 1H), 7.37 (d, J = 4.8 Hz, 1H), 6.94 (d, J = 5.4 Hz, 1H), 1.74 (d, J = 13.8 Hz, 6H). LC-MS m/z: 387.0 $[M + H]^+$. |
| A23 | 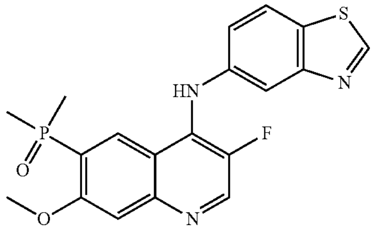 [SMILES: COc1cc2ncc(F)c(Nc3ccc4scnc4c3)c2cc1P(C)(C)=O] | G | $^1$H NMR (300 MHz, DMSO-$d_6$) δ 9.49 (s, 1H), 9.33 (s, 1H), 8.80 (s, 1H), 8.73 (d, J = 14.7 Hz, 1H), 8.02 (d, J = 9.0 Hz, 1H), 7.56 (s, 1H), 7.49 (s, 1H), 7.23 (d, J = 6.6 Hz, 1H), 4.02 (s, 3H), 1.71 (d, J = 13.5 Hz, 6H). LC-MS m/z: 402.1 $[M + H]^+$. |
| A24 | 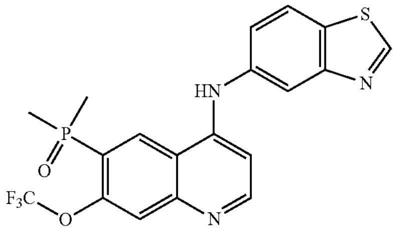 [SMILES: CP(C)(=O)c1cc2c(Nc3ccc4scnc4c3)ccnc2cc1OC(F)(F)F] | C | $^1$H NMR (300 MHz, DMSO-$d_6$) δ 9.78 (s, 1H), 9.44 (s, 1H), 8.97 (d, J = 13.2 Hz, 1H), 8.56 (d, J = 5.4 Hz, 1H), 8.22 (d, J = 8.7 Hz, 1H), 8.05 (s, 1H), 7.75 (s, 1H), 7.54 (d, J = 9.0 Hz, 1H), 7.04 (d, J = 5.1 Hz, 1H), 1.83 (d, J = 13.8 Hz, 6H). LC-MS m/z: 438.0 $[M + H]^+$. |
| A25 | 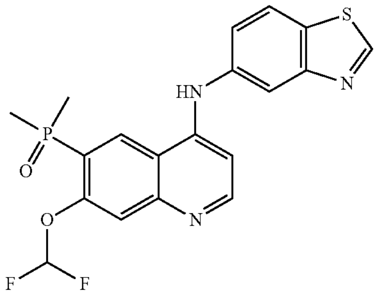 [SMILES: CP(C)(=O)c1cc2c(Nc3ccc4scnc4c3)ccnc2cc1OC(F)F] | C | $^1$H NMR (300 MHz, DMSO-$d_6$) δ 9.70 (s, 1H), 9.42 (s, 1H), 8.92 (d, J = 13.8 Hz, 1H), 8.53 (d, J = 5.1 Hz, 1H), 8.19 (d, J = 8.7 Hz, 1H), 8.03 (s, 1H), 7.64 (t, J = 73.2 Hz, 1H), 7.62 (d, J = 3.6 Hz, 1H), 7.54 (d, J = 8.1 Hz, 1H), 7.01 (d, J = 5.1 Hz, 1H), 1.80 (d, J = 13.8 Hz, 6H). LC-MS m/z: 420.0 $[M + H]^+$. |
| A26 | 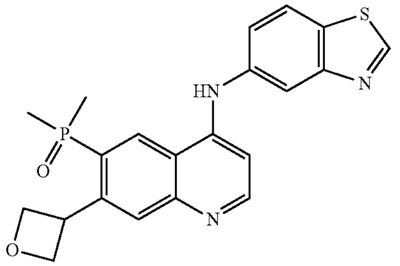 [SMILES: CP(C)(=O)c1cc2c(Nc3ccc4scnc4c3)ccnc2cc1C1COC1] | H | $^1$H NMR (300 MHz, DMSO-$d_6$) δ 9.89 (s, 1H), 9.46 (s, 1H), 8.72-8.58 (m, 1H), 8.54 (d, J = 5.7 Hz, 1H), 8.34-8.22 (m, 2H), 8.08 (s, 1H), 7.56 (d, J = 8.4 Hz, 1H), 6.93 (d, J = 5.7 Hz, 1H), 5.29-5.14 (m, 1H), 5.06 (t, J = 6.0 Hz, 2H), 4.71 (t, J = 6.0 Hz, 2H), 1.84 (d, J = 12.9 Hz, 6H). LC-MS m/z: 410.1 $[M + H]^+$. |

TABLE 1-continued

| Selected compounds (A1-A29, B1-B2) of the present invention. | | | |
|---|---|---|---|
| NO. | Structure | Method | $^1$HNMR&LC-MS |
| A27 | 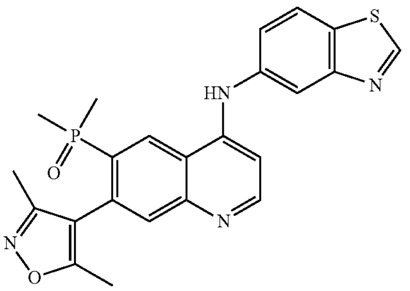 [SMILES: Cc1noc(C)c1-c1cc2nccc(Nc3ccc4scnc4c3)c2cc1P(C)(C)=O] | E | $^1$H NMR (300 MHz,DMSO-$d_6$) δ 9.67 (s, 1H), 9.45 (s, 1H), 8.78 (d, J = 14.4 Hz, 1H), 8.57-8.53 (m, 1H), 8.25 (d, J = 7.2 Hz, 1H), 8.06 (s, 1H), 7.72 (s, 1H), 7.60-7.51 (m, 1H), 6.99 (s, 1H), 2.26 (s, 3H), 2.07 (s, 3H), 1.82-1.51 (m, 6H). LC-MS (m/z): 449.1 $[M + H]^+$. |
| A28 | 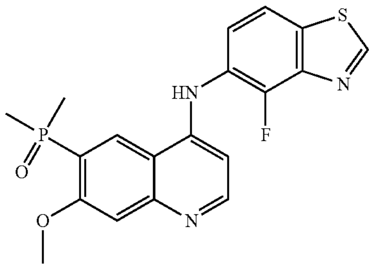 [SMILES: COc1cc2nccc(Nc3ccc4scnc4c3F)c2cc1P(C)(C)=O] | A,C | $^1$H NMR (300 MHz, DMSO-$d_6$) δ 9.47 (s, 2H), 8.82 (d, J = 14.4 Hz, 1H), 8.41 (s, 1H), 8.04 (s, 1H), 7.56 (s, 1H), 7.37 (s, 1H), 6.32 (s, 1H), 4.00 (s, 3H), 1.74 (d, J = 14.1 Hz, 6H).LC-MS m/z: 402.0 $[M + H]^+$. |
| A29 | 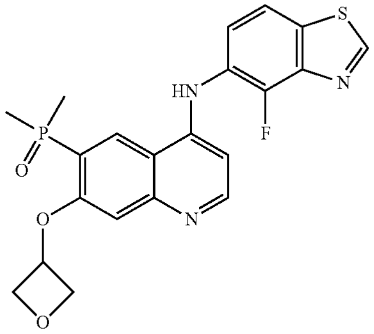 [SMILES: CP(C)(=O)c1cc2c(Nc3ccc4scnc4c3F)ccnc2cc1OC1COC1] | A,D | $^1$H NMR (300 MHz, DMSO-$d_6$) δ 9.53 (s, 1H), 9.47 (s, 1H), 8.88 (d, J = 14.1 Hz, 1H), 8.37 (s, 1H), 8.05 (d, J = 8.7 Hz, 1H), 7.63-7.47 (m, 1H), 6.99 (s, 1H), 6.32 (s, 1H), 5.65-5.51 (m, 1H), 5.10-5.01 (m, 2H), 4.71-4.61 (m, 2H), 1.82 (d, J = 13.8 Hz, 6H). LC-MS m/z: 444.1 $[M + H]^+$. |
| B1 | 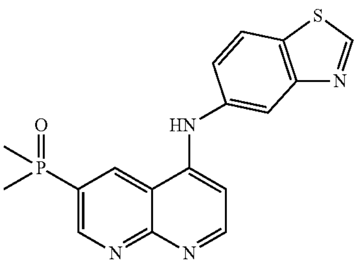 [SMILES: CP(C)(=O)c1cnc2nccc(Nc3ccc4scnc4c3)c2c1] | I | $^1$H NMR (400 MHz, DMSO-$d_6$) δ 10.57 (s, 1H), 9.56-9.43 (m, 2H), 9.31 (s, 1H), 8.60 (s, 1H), 8.30 (d, J = 8.4 Hz, 1H), 8.12 (s, 1H), 7.57 (d, J = 8.0 Hz, 1H), 6.99 (s, 1H), 1.88 (s, 3H), 1.85 (s, 3H). LC-MS m/z: 355.1 $[M + H]^+$. |
| B2 | 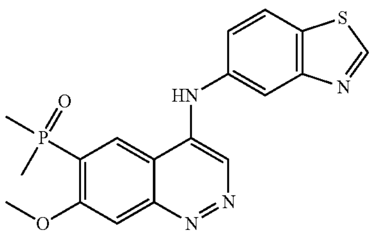 [SMILES: COc1cc2nncc(Nc3ccc4scnc4c3)c2cc1P(C)(C)=O] | J | $^1$H NMR (400 MHz, DMSO-$d_6$) δ 9.18-9.06 (m, 2H), 8.88 (s, 1H), 8.16 (s, 1H), 8.07 (d, J = 8.4 Hz, 1H), 7.68 (s, 1H), 7.51 (d, J = 8.4 Hz, 1H), 4.04 (s, 3H), 1.69 (s, 3H), 1.66 (s, 3H). LC-MS m/z: 385.1 $[M + H]^+$. |

EXAMPLE 11. BINDING AFFINITY ASSAY

For most assays, kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 111× stocks in 100% DMSO. Kds were determined using an 11-point 3-fold compound dilution series with three DMSO control points. All compounds for $K_d$ measurements are distributed by acoustic transfer (non-contact dispensing) in 100% DMSO. The compounds were then diluted directly into the assays such that the final concentration of DMSO was 0.9%. All reactions performed in polypropylene 384-well plate. Each was a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM nonbiotinylated affinity ligand) and incubated at room temperature with shaking for 30 minutes. The kinase concentration in the eluates was measured by qPCR.

An 11-point 3-fold serial dilution of each test compound was prepared in 100% DMSO at 100× final test concentration and subsequently diluted to 1× in the assay (final DMSO concentration=1%). Most Kds were determined using a compound top concentration=30,000 nM. If the initial Kd determined was <0.5 nM (the lowest concentration tested), the measurement was repeated with a serial dilution starting at a lower top concentration. A Kd value reported as 40,000 nM indicates that the Kd was determined to be >30,000 nM.

Binding constants (Kds) were calculated with a standard dose-response curve using the Hill equation:

$$\text{Response} = \text{Background} + \frac{\text{Signal} - \text{Background}}{1 + \left(Kd^{\text{Hill Slope}} / \text{Dose}^{\text{Hill Slope}}\right)}$$

The Hill Slope was set to −1.

Curves were fitted using a non-linear least square fit with the Levenberg-Marquardt algorithm.

TABLE 2

The binding affinity of test compounds on RIP2 kinase

| NO. | RIP2 Kd (nM) | NO. | RIP2 Kd (nM) |
|---|---|---|---|
| A1 | 28 | A2 | 89 |
| A3 | 430 | A4 | 89 |
| A5 | 120 | A6 | 3.1 |
| A7 | 5.8 | A8 | 2.0 |
| A9 | 2.1 | A10 | 1.8 |
| A11 | 3.0 | A12 | 2.3 |
| A13 | 1.4 | A14 | 3.0 |
| A15 | 3.0 | A16 | 3.8 |
| A20 | 8.7 | A21 | 1.5 |
| A24 | 5.2 | A25 | 6.4 |
| A26 | 12 | B1 | 3200 |

Conclusion: As shown in table 2, compounds A1-A16, A20-A21, A24-A26 may have high affinity with RIP2 kinase while B1 exhibited low affinity.

EXAMPLE 12. THP-1 CELL ASSAY

Acute monoblastic and monocytic leukemia (THP-1) was obtained from ATCC (item NO. TIB-202™). The temperature of the sterile incubator is 37~38° C., the osmotic pressure is 260~320 mmol/L, the pH range is 7.2~7.4, and the ratio of carbon dioxide gas is 5%.

Cells were seeded in 96-well plates. After an hour, cells were incubated with test compounds for 2 hours. MDP (10 μL) was added and incubated for 6 hours. The samples were centrifuged (3000 rmp/min) for 5 minutes. The concentration of IL-8 in the supernatants was detected by IL-8 ELISA.

TABLE 3

Inhibition of IL-8 of test compounds (10 nM)

| NO. | IL-8 inhibition % | NO. | IL-8 inhibition % |
|---|---|---|---|
| A6 | 50 | A7 | 25 |
| A8 | 51 | A9 | 55 |
| A10 | 51 | A11 | 37 |
| A17 | 11 | A18 | 12 |
| A19 | 13 | A22 | 60 |
| A23 | 5 | A27 | 37 |
| A28 | 63 | A29 | 85 |
| B2 | 0 | | |

Conclusion: From table 3, compounds A6-A11, A17-A19, A22-A23 and A27-29 may inhibit IL-8 in THP-1 induced by MDP effectively while B2 may have no effect.

EXAMPLE 13. THERMODYNAMIC SOLUBILITY TEST

Experimental Procedure a. Add assay buffer into compound powder to make 4 mg/mL solution.
b. Sample tubes are shaken for 1 hour (1000 rpm), then equilibrated over night at room temperature.
c. Samples are centrifuged (10 min-12000 rpm) to precipitate un-dissolved particles.
d. Supernatants are transferred to new tubes.
e. Concentrations of the supernatants after centrifugation are determined by LCMSMS detection.

TABLE 4

Thermodynamic solubility of test compounds

| NO. | Solubility FaSSIF (pH 6.5) |
|---|---|
| A6 | 6115 μM |
| A7 | 5310 μM |
| A8 | 1038 μM |
| A9 | 283 μM |
| A13 | 4325 μM |

Conclusion: Table 4 shows that compounds A6-A9, A13 have favorable solubility.

EXAMPLE 14. CYP INHIBITION TEST

Experimental Procedure

Preheat 0.1 M potassium phosphate buffer (K-buffer), pH 7.4:

100 mM K-Buffer: mix 9.5 mL Stock A into 40.5 mL Stock B, bring total volume to 500 mL with Milli-Q water, titrate the buffer with KOH or $H_3PO_4$ to pH 7.4.

Stock A (1 M monobasic potassium phosphat): 136.5 g of monobasic potassium phosphate in 1 L of Milli-Q water.

Stock B (1 M dibasic potassium phosphate): 174.2 g of dibasic potassium phosphate in 1 L of Milli-Q water.

Prepare test compound and reference inhibitors (400×) in a 96-well plate:

a. Transfer 8 μL of 10 mM test compounds to 12 μL of ACN.

b. Prepare inhibitor spiking solution for CYP1A2, $CYP2C_9$ and CYP2D6 in cocktail: 12 μL of 1 mM α-Naphthoflavon+10 μL of 40 mM Sulfaphenazole+10 μL of 10 mM Quinidine+8 μL of DMSO c. Prepare individual inhibitor spiking solution for CYP3A4, CYP2B6, CYP2C8 and CYP2C19: 8 μL of DMSO stock to 12 μL of ACN.

Prepare 4×NADPH cofactor (66.7 mg NADPH in 10 mL 0.1 M K-buffer, pH7.4)

Prepare 4× substrate (2 mL for each isoform) as indicated in the table below (add HLM where required on ice).

Prepare 0.2 mg/mL HLM solution (10 μL of 20 mg/mL to 990 μL of 0.1 M K-buffer) on ice.

Add 400 μL of 0.2 mg/mL HLM to the assay wells and then add 2 μL of 400× test compound (see step 2.1) into the designated wells (see table 1) on ice.

Add 200 μL of 0.2 mg/mL HLM to the assay wells and then add 1 μL of reference inhibitor solution (see step 2.2 and 2.3) into the designated wells (see table 1) on ice.

Add following solutions (in duplicate) in a 96-well assay plate on ice:

a. Add 30 μL of 2× test compound and reference compound in 0.2 mg/mL HLM solution (see step 6 and 7);

b. Add 15 μL of 4× substrate solution (see step 4).

Pre-incubate the 96-well assay plate and NADPH solution at 37° C. for 5 minutes.

Add 15 μL of pre-warmed 8 mM NADPH solution to into the assay plates to initiate the reaction. (See step 3)

Incubate the assay plate at 37° C. 5 min for 3A4, 10 min for 1A2, 2B6, 2C8, 2C9 and 2D6, and 45 min for 2C19.

Stop the reaction by adding 120 μL of ACN containing IS (see IS preparation in Table 2).

After quenching, shake the plates at the vibrator (IKA, MTS 2/4) for 10 min (600 rpm/min) and then centrifuge at 5594 g for 15 min (ThermoMultifuge×3R).

Transfer 50 μL of the supernatant from each well into a 96-well sample plate containing 50 μL of ultra pure water (Millipore, ZMQS50F01) for LC/MS analysis.

Table 5. System for CYP Inhibition

See FIG. 4.

TABLE 6

| CYP inhibition of test compounds | | | | | | |
|---|---|---|---|---|---|---|
| | CYP inhibition (10 μM) | | | | | |
| NO. | 1A2 | 2C9 | 2C19 | 2D6 | CYP3A4 (Midazolam) | CYP3A4 (Testosterone) |
| A6 | 12.84 | −2.15 | 4.72 | 2.69 | −6.48 | −4.01 |
| A14 | 2.40 | −6.07 | −0.37 | −0.68 | −7.95 | 1.73 |
| A15 | 8.38 | −3.76 | 2.17 | 2.04 | −3.98 | 2.31 |
| A16 | 11.08 | −6.42 | −10.34 | 0.68 | 1.17 | 2.12 |

Conclusion: As shown in table 6. compounds A6, A14-A16 (10 NM) have no obvious effect on CYP isozymes. The favorable inhibition suggested low drug/drug interaction of these compounds.

EXAMPLE 15. CACO-2 PERMEABILITY TEST

Experimental Procedure

1. Prewarm HBSS Buffer in 37° C. water bath
2. Take compounds from −20° C., sonicate for a few minutes (no less than 1 minute)
3. Solution preparation For A-to-B direction:

HBSS buffer with 0.3% DMSO and 5 μM LY: add 150 μL DMSO and 50 μL LY (5 mM) into 50 ml HBSS buffer (pH7.4).

HBSS buffer with 0.1% DMSO and 5 μM LY: add 50 μL DMSO and 50 μL LY (5 mM) into 50 mL HBSS buffer (pH7.4).

For B-to-A direction:

HBSS buffer with 0.3% DMSO: add 150 μL DMSO into 50 ml HBSS buffer (pH7.4)

HBSS buffer with 0.1% DMSO: add 50 μL DMSO into 50 ml HBSS buffer (pH7.4).

Receiver Solution Buffer:

For A-to-B direction:

Prepare HBSS buffer with 0.4% DMSO: add 200 μL DMSO into 50 ml HBSS buffer (pH7.4).

For B-to-A direction:

Prepare HBSS buffer with 0.4% DMSO and 5 uM LY: add 200 μL DMSO and 50 μL LY (5 mM) into 50 ml HBSS buffer (pH7.4).

Table 7. Preparation of donor solution

See FIG. 5.

4. Take cell culture plate out of incubator, wash the cell monolayers with HBSS buffer, and then measure TEER values at Rm temperature.
5. Centrifuge the compound solution (from step 3) at 4000 rpm for 5 min before loading to donor chambers.
6. Add solution based on the volumes listed in the following table (make sure to take extra 100 uL of donor sample for T0 as Backup).

TABLE 8

| Solution volume | | | |
|---|---|---|---|
| Position | Transport Direction | Volume Added | Final Volume |
| Apical | A-B (Donor chamber) | 600 μL of A-to-B dosing solution (100 μL for LY measurement and 100 L for Backup) | 400 L |
| Basolateral | A-B (Receiver chamber) | 800 μL 0.4% DMSO HBSS | 800 L |
| Basolateral | B-A (Donor chamber) | 900 μL B-to-A dosing solution (100 μL for Backup) | 800 μL |
| Apical | B-A (Receiver chamber) | 500 μL 0.4% DMSO HBSS + LY (100 μL for LY measurement) | 400 μL |

7. To determine LY concentration in the apical chamber, take 100 μL sample from apical chambers into an opaque plate for LYT0.
8. Prewarm apical and basolateral plates at 37° C. for about 5 min, then begin transport by placing the apical plate onto basolateral plate.
9. Keep the plates in incubator at 37° C. for 90 min
10. Prepare 20× solution

TABLE 9

| Preparation of working solutions | | | | |
|---|---|---|---|---|
| Compound solution (μM) | Solution (μL) | $MeOH/H_2O$ (μL) | | Final solution (μM) |
| 300 | 100 | 400 | → | 60 |
| 60 | 100 | 200 | → | 20 |
| 20 | 100 | 400 | → | 4 |
| 4 | 100 | 400 | → | 0.8 |
| 0.8 | 100 | 300 | → | 0.2 |
| 0.2 | 100 | 100 | → | 0.1 |

11. Separate the apical plate from the basolateral plate after 90-min incubation.
12. Take 100 μL samples from basolateral plate to an opaque plate as LYT90.
13. Measure LY concentrations for LYT0 and LYT90 by Fluorometer (at excitation of 485 nm/emission of 535 nm).
14. Sample preparation for LC-MS/MS: Donor or receiver samples are diluted by 0.4% DMSO HBSS, then mix with ACN with IS (Osalmid or Imipramine)

TABLE 10

| Caco-2 permeability of test compounds | | | |
|---|---|---|---|
| | Caco-2 Permeability | | |
| NO. | A-B ($10^{-6}$ cm · $s^{-1}$) | B-A ($10^{-6}$ cm · $s^{-1}$) | B-A/A-B |
| A6 | 15.15 | 32.98 | 2.18 |
| A7 | 0.5 | 10.22 | 20.52 |
| A8 | 11.95 | 35.62 | 2.98 |
| A9 | 7.85 | 46.48 | 5.92 |
| A13 | <0.14 | 0.27 | >1.93 |
| A14 | 7.00 | 35.93 | 5.13 |
| A15 | 5.36 | 35.04 | 6.53 |
| A16 | 2.16 | 31.07 | 14.40 |
| A24[a] | 16.9 | 26.6 | 1.58 |

[a]Test at 2 μM

Conclusion: As can be seen from table 10, compounds A6, A24 had high permeability and no obvious efflux. Compound A8 also had favorable permeability but is an efflux substrate. Permeability of Compounds A9, A14, A15 is moderate while compounds A7, A13, A16 is low. It can be seen that minor changes in substituents will significantly change the permeability and even cause efflux.

EXAMPLE 16. PROTEIN BINDING TEST

Experimental Procedure

1. Spiking Solutions of Test and Reference Compounds
1.1 Solution A (0.5 mM): Add 10 μL of 10 mM stock solution into 190 μL of DMSO.
1.2 Solution B (0.02 mM): Add 8 μL of Solution A into 192 μL of 0.05 M sodium phosphate buffer. The final DMSO concentration in Solution B is 4%.
2. Preparation of Test and Reference Compounds
2.1 Preload a 96-well plate with 380 μL aliquots of plasma in the wells designated for plasma and buffer, respectively.
2.2 Spike 20 μL of Solution B (0.02 mM of test and reference compounds) into the pre-loaded plasma in the 96-well plate. The final test concentration is 1 μM containing 0.2% DMSO.

3. Dialysis Sample Loading
3.1 Preparing plasma against buffer system (duplicate): Apply aliquots of 100 μL of blank dialysis buffer to the receiver side of dialysis chambers. Then apply aliquots of 100 μL of the plasma spiked with test and reference compounds to the donor side of the dialysis chambers.
3.2 Preparing T0 plasma samples for initial concentrations (duplicate):
3.2.1 Aliquot 25 μL of the plasma spiked with test and reference compounds into a 96-well sample preparation plate as T0 plasma samples
3.2.2 Mix the aliquots with same volume of blank buffer (50:50, v/v).
3.2.3 Quench the samples with 200 μL of acetonitrile containing internal standard (IS).
3.3 Cover the dialysis block with a plastic lid and place the entire apparatus in a shaker (60 rpm) for 5 hours at 37° C.
3.4 Preparing dialyzed samples after 5-hour incubation:
3.4.1 Aliquot 25 μL from both the donor sides and receiver sides of the dialysis apparatus into new sample preparation plates and mix the aliquots with same volume of opposite matrixes (blank buffer to plasma and vice versa).
3.4.2 Quench the samples with 200 μL acetonitrile containing internal standard (IS). Vortex all the samples (from 0 h and 5 h) at 600 rpm for 10 min followed by centrifugation at 5594 g for 15 minutes (ThermoMultifuge×3R).
3.4.3 Transfer 50 μL of the supernatants to a new 96-well plate and mix the samples with 50 μL of Milli-Q water. Cover the sample plate and store it in a freezer (−20° C.) until LC/MS/MS analysis.

TABLE 11

| Results of compounds protein binding | | | |
|---|---|---|---|
| | Protein binding (%) | | |
| NO. | human | rat | dog |
| A6 | 87.6 | 98.1 | 86.2 |
| A14 | 82.3 | 92.7 | 83.5 |
| A15 | 81.2 | 94.1 | 87.1 |
| A16 | 80.5 | 93.1 | 85.5 |
| A24 | 98.7 | 99.9 | 99.0 |
| A25 | 96.8 | 99.4 | 95.0 |

Conclusion: As shown in table 11, compounds A6, A14-A16 have moderate protein binding in human, rat and dog while compound A24 has high protein binding. Compound A25 has high protein binding in rat and moderate in human, dog.

EXAMPLE 17. METABOLIC STABILITY TEST

Experimental Procedure

1. Buffers:
Buffer A: 1.0 L of 0.1 M monobasic Potassium Phosphate buffer containing 1.0 mM EDTA
Buffer B: 1.0 L of 0.1 M Dibasic Potassium Phosphate buffer containing 1.0 mM EDTA
Buffer C: 0.1 M Potassium Phosphate buffer, 1.0 mM EDTA, pH 7.4 by titrating 700 mL of buffer B with buffer A while monitoring with the pH meter.
2. Reference compounds (Ketanserin) and test compounds spiking solution:

500 μM spiking solution: add 10 μL of 10 mM DMSO stock solution into 190 μL ACN.

1.5 μM spiking solution in microsomes (0.75 mg/mL): add 1.5 μL of 500 μM spiking solution and 18.75 μL of 20 mg/mL liver microsomes into 479.75 μL of Buffer C on ice.

3. Prepare NADPH stock solution (6 mM) by dissolving NADPH into buffer C.
4. Dispense 30 μL of 1.5 μM spiking solution containing 0.75 mg/mL microsomes solution to the assay plates designated for different time points (0-, 5-, 15-, 30-, 45-min) on ice.
5. For 0-min time point, add 135 μL of ACN containing IS to the wells of 0-min plate and then add 15 μL of NADPH stock solution (6 mM).
6. Pre-incubate all other plates at 37° C. for 5 minutes.
7. Add 15 μL of NADPH stock solution (6 mM) to the plates to start the reaction and timing.
8. At 5-min, 15-min, 30-min, and 45-min, add 135 μL of ACN containing IS to the wells of corresponding plates, respectively, to stop the reaction.
9. After quenching, shake the plates at the vibrator (IKA, MTS 2/4) for 10 min (600 rpm/min) and then centrifuge at 5594 g for 15 min (ThermoMultifuge×3R).
10. Transfer 50 μL of the supernatant from each well into a 96-well sample plate containing 50 μL of ultra pure water (Millipore, ZMQS50F01) for LC/MS analysis.

TABLE 12

Metabolic stability of test compounds

| | $T_{1/2}$ (min) | | | Cl (mL/min/kg) | | |
|---|---|---|---|---|---|---|
| NO. | HLM | RLM | DLM | HLM | RLM | DLM |
| A6 | 585.85 | 95.74 | 663.70 | 2.97 | 25.94 | 5.21 |
| A7 | 420.88 | 146.12 | 1337.59 | 4.13 | 17.00 | 2.58 |
| A8 | 109.21 | 95.69 | 253.01 | 15.92 | 25.95 | 13.66 |
| A9 | 51.95 | 38.89 | 114.69 | 33.46 | 63.87 | 30.12 |
| A13 | 2523.60 | 78.70 | 198.29 | 0.69 | 31.56 | 17.42 |
| A14 | 75.79 | 64.37 | 618.90 | 22.94 | 38.58 | 5.58 |
| A15 | 88.56 | 50.16 | 830.65 | 19.63 | 49.51 | 4.16 |
| A16 | 174.16 | 147.05 | / | 9.98 | 16.89 | 0.00 |

Conclusion: Table 12 shown that compounds A6-A9 and A13-A16 displayed low to moderate clearance in human, rat and dog.

EXAMPLE 18. PHARMACOKINETIC EVALUATION

Purpose 1. Evaluation of Pharmacokinetic Profile of Candidate Compounds in Mice

Experimental Procedure

The mice pharmacokinetic characteristics of compounds were tested by standard protocols. The candidate compounds were made into clear solution for single intravenous injection (i.v.) and suspension for oral administration (p.o.). Intravenous vehicle is 5% DMSO+95% Saline while oral vehicle is 0.5% CMCNa. The experiment used 48 male mice and 24 mice for intravenous at a dose of 2 mg/kg. Plasma samples were collected at 0 h (before dosing) and 0.083 h, 0.25 h, 0.5 h, 1 h, 2 h, 4 h, 8 h, 24 h after dosing. Another 24 mice were orally administrated with a dose of 10 mg/kg. Plasma samples were collected at 0 h (before dosing) and 0.25 h, 0.5 h, 1 h, 2 h, 4 h, 6 h, 8 h, 24 h after dosing.

Blood samples were placed in tubes containing K2-EDTA and stored on ice until centrifuged. The blood samples were centrifuged at 6800 g for 6 minutes at 2-8° C. within 1 h after collected and stored frozen at approximately −80° C.

The analytical results were confirmed using quality control samples for intra-assay variation. The accuracy of >66.7% of the quality control samples and 50% of all QC samples at each concentration level were between 80-120% of the known value(s).

Standard set of parameters including Area Under the Curve (AUC(0-t) and AUC(0-∞)), elimination half-live (T1/2), maximum plasma concentration (Cmax), time to reach maximum plasma concentration (Tmax) were calculated using noncompartmental analysis modules in FDA certified pharmacokinetic program Phoenix WinNonlin 7.0 (Pharsight, USA) by the Study Director.

TABLE 13

Mice PK of test compounds

| Compounds | | A6 | A24 | A25 |
|---|---|---|---|---|
| i.v.: 2 mg/kg | Cl (mL/kg/min) | 11.1 | 1.5 | 4.3 |
| | Vd (L/kg) | 1.1 | 0.27 | 0.59 |
| | AUC(ng · h/mL) | 2989 | 22597 | 6513 |
| | $T_{1/2}$ (h) | 1.2 | 2.2 | 1.6 |
| p.o.: 10 mg/kg | Cmax (ng/mL) | 9610 | 16172 | 19178 |
| | Tmax (h) | 0.5 | 0.8 | 0.7 |
| | AUC (ng · h/mL) | 19236 | 89091 | 68337 |
| | F (%) | 129 | 79 | 210 |

Conclusion: Compounds A6, A24, and A25 had excellent plasma exposure and bioavailability in mice.

Purpose 2. Evaluation of Pharmacokinetic Profile of Candidate Compounds in Rats

Experimental Procedure

The rat pharmacokinetic characteristics of compounds were tested by standard protocols. The candidate compounds were made into clear solution for single intravenous injection (i.v.) and suspension for oral administration (p.o.). Intravenous vehicle is 5% DMSO+95% Saline while oral vehicle is 0.5% CMCNa. The experiment used 9 male rats and 3 rats for intravenous at a dose of 2 mg/kg. Plasma samples were collected at 0 h (before dosing) and 0.083 h, 0.25 h, 0.5 h, 1 h, 2 h, 4 h, 8 h, 24 h after dosing. 3 rats were orally administrated at a dose of 10 mg/kg and 3 rats were orally administrated at a dose of 100 mg/kg. Plasma samples were collected at 0 h (before dosing) and 0.25 h, 0.5 h, 1 h, 2 h, 4 h, 6 h, 8 h, 24 h after dosing.

Blood samples were placed in tubes containing K2-EDTA and stored on ice until centrifuged. The blood samples were centrifuged at 6800 g for 6 minutes at 2-8° C. within 1 h after collected and stored frozen at approximately −80° C.

The analytical results were confirmed using quality control samples for intra-assay variation. The accuracy of >66.7% of the quality control samples and 50% of all QC samples at each concentration level were between 80-120% of the known value(s).

Standard set of parameters including Area Under the Curve (AUC(0-t) and AUC(0-∞)), elimination half-live (T1/2), maximum plasma concentration (Cmax), time to reach maximum plasma concentration (Tmax) were calculated using noncompartmental analysis modules in FDA certified pharmacokinetic program Phoenix WinNonlin 7.0 (Pharsight, USA) by the Study Director.

TABLE 14

Rat PK of test compounds

| Compounds | | A6 | A24 |
|---|---|---|---|
| i.v.: 2 mg/kg | Cl (mL/kg/min) | 4.2 | 1.2 |
| | Vd (L/kg) | 0.6 | 0.19 |
| | AUC(ng · h/mL) | 7889 | 26543 |
| | $T_{1/2}$ (h) | 1.7 | 18 |
| p.o.: 10 mg/kg | Cmax (ng/mL) | 3323 | 20436 |
| | Tmax (h) | 3.3 | 1.8 |
| | AUC (ng · h/mL) | 18803 | 247712 |
| | F (%) | 48 | 187 |
| p.o.: 100 mg/kg | Cmax (ng/mL) | 68433 | 196807 |
| | Tmax (h) | 4.7 | 24 |
| | AUC (ng · h/mL) | 729373 | / |
| | F (%) | 185 | 244 |

Conclusion: Compounds A6, A24 had excellent plasma exposure and bioavailability in rat.

Purpose 3. Evaluation of Pharmacokinetic Profile of Candidate Compounds in Beagle Dog Experimental Procedure:

The beagle dog pharmacokinetic characteristics of compounds were tested by standard protocols. The candidate compounds were made into clear solution for single intravenous injection (i.v.) and suspension for oral administration (p.o.). Intravenous vehicle is 5% DMSO+95% Saline while oral vehicle is 0.5% CMCNa. The experiment used 9 dogs. The dogs for intravenous at a dose of 1 mg/kg. Plasma samples were collected at 0 h (before dosing) and 0.083 h, 0.25 h, 0.5 h, 1 h, 2 h, 4 h, 8 h, 24 h after dosing. Three dogs were orally administrated at a dose of 5 mg/kg. Another 3 dogs were orally administrated at a dose of 15 mg/kg or 30 mg/kg. Plasma samples were collected at 0 h (before dosing) and 0.25 h, 0.5 h, 1 h, 2 h, 4 h, 6 h, 8 h, 24 h after dosing.

Blood samples were placed in tubes containing K2-EDTA and stored on ice until centrifuged. The blood samples were centrifuged at 6800 g for 6 minutes at 2-8° C. within 1 h after collected and stored frozen at approximately −80° C.

The analytical results were confirmed using quality control samples for intra-assay variation. The accuracy of >66.7% of the quality control samples and 50% of all QC samples at each concentration level were between 80-120% of the known value(s).

Standard set of parameters including Area Under the Curve (AUC(0-t) and AUC(0-∞)), elimination half-live (T1/2), maximum plasma concentration (Cmax), time to reach maximum plasma concentration (Tmax) were calculated using noncompartmental analysis modules in FDA certified pharmacokinetic program Phoenix WinNonlin 7.0 (Pharsight, USA) by the Study Director.

TABLE 15

Beagle dog PK of A6

| Compound | | A6 |
|---|---|---|
| i.v.: 1 mg/kg | Cl (mL/kg/min) | 9.5 |
| | Vd (L/kg) | 1.7 |
| | AUC(ng · h/mL) | 1645 |
| | $T_{1/2}$ (h) | 2.1 |

TABLE 15-continued

Beagle dog PK of A6

| Compound | | A6 |
|---|---|---|
| p.o.: 5 mg/kg | Cmax (ng/mL) | 2192 |
| | Tmax (h) | 0.7 |
| | AUC (ng · h/mL) | 10800 |
| | F (%) | 131 |
| p.o.: 30 mg/kg | Cmax (ng/ml) | 8632 |
| | Tmax (h) | 2.7 |
| | AUC (ng · h/mL) | 90827 |
| | F (%) | 184 |

TABLE 16

Beagle dog PK of A24

| Compound | | A24 |
|---|---|---|
| i.v.: 1 mg/kg | Cl (mL/kg/min) | 4.3 |
| | Vd (L/kg) | 0.7 |
| | AUC(ng · h/mL) | 3801 |
| | $T_{1/2}$ (h) | 1.9 |
| p.o.: 5 mg/kg | Cmax (ng/mL) | 9717 |
| | Tmax (h) | 1.1 |
| | AUC (ng · h/mL) | 40337 |
| | F (%) | 212 |
| p.o.: 15 mg/kg | Cmax (ng/mL) | 13264 |
| | Tmax (h) | 3.0 |
| | AUC (ng · h/mL) | 50408 |
| | F (%) | 88 |

Conclusion: Compounds A6 and A24 had excellent plasma exposure and bioavailability in beagle dog.

EXAMPLE 19. VIVO PHARMACODYNAMICS STUDY OF MDP (MURAMYL DIPEPTIDE) INDUCED PERITONITIS

Purpose: To Evaluate Vivo Activity of RIP2 Kinase Inhibitors.

Experimental Procedure

Mice were divided into four groups Including normal group, DMSO group, positive control group (GSK2983559) and compound group. Mice were dosed by gavage with either GSK2983559 at 10 mg/kg or candidate compounds at 3, 10 mg/kg 30 minutes prior to MDP injection (100 μg/mouse, ip). At 3 hours post MDP administration, the blood sample was collected from ocular vein after anesthesia. IL-6 levels were detected by ELISA.

Figure 2:
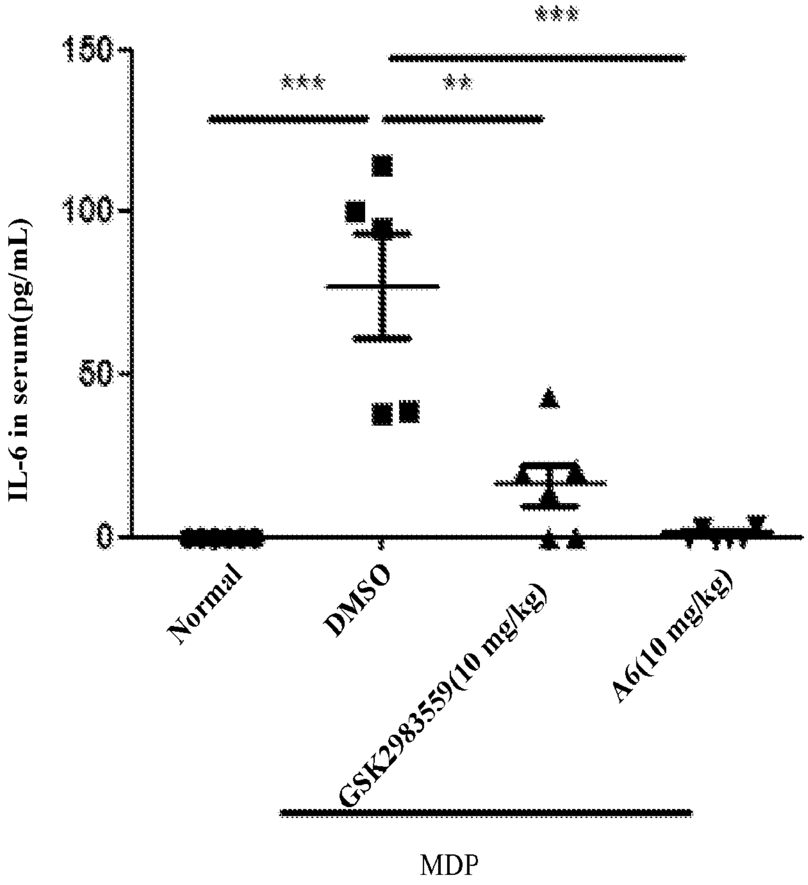
FIG. 2 depicts depicts the experimental results of the protective effect of compound A6 against muramyl dipeptide (MDP) induced peritonitis in Example 19.
Figure 3:
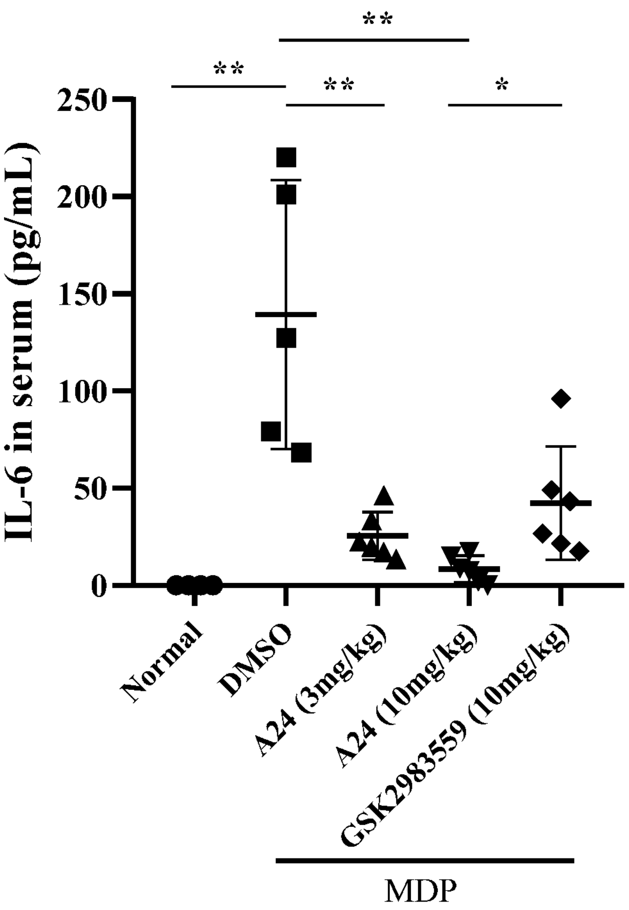
FIG. 3 depicts depicts the experimental results of the protective effect of compound 24 against muramyl dipeptide (MDP) induced peritonitis in Example 19.

Results: The experimental results were shown in FIGS. 2 and 3.

Conclusion: IL-6 levels were significantly increased after MDP injection compared with normal group. Suggesting that inflammation pathway downstream was activated and the model was successful established. IL-6 levels in each administration group had declined compared with the model group. Among them, Compounds A6 and A24 inhibited the level of IL-6 more effectively than positive control GSK2983559 at the same dosage. These two compounds can inhibit the activity of RIP2 kinase more effectively than GSK2983559.

What is claimed is:

1. A compound of Formula (I):

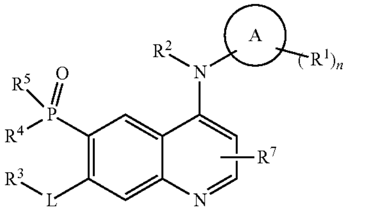

(I)

or a pharmaceutically acceptable salt, ester, solvate, prodrug, isotope-labeled derivative, stereoisomer or tautomer thereof, wherein:

n is 0, 1, 2 or 3;

L is a bond, —O—, —N($R^6$)—, or

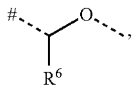

wherein # denotes a connection to $R^3$;

ring A is $C_{6-10}$ aryl and 5-10 membered heteroaryl;

$R^1$ is independently H, deuterium, halide, —OH, amino, —CN, $C_{1-6}$ alkyl, $C_{3-6}$ cycloalkyl, —O($C_{1-6}$ alkyl), —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{2-6}$ alkenyl and $C_{2-6}$ alkynyl are unsubstituted or substituted with 1 to 3 groups independently selected from $R^a$;

$R^2$ is independently H, deuterium, $C_{1-3}$ alkyl or $C_{3-6}$ cycloalkyl, wherein $C_{1-3}$ alkyl and $C_{3-6}$ cycloalkyl are unsubstituted or substituted with 1 to 3 groups independently selected from $R^b$;

$R^3$ is independently H, halide, —OH, amino, $C_{1-6}$ alkyl, $C_{3-6}$ cycloalkyl, —O($C_{1-6}$ alkyl), 3-6 membered cycloheteroalkyl, $C_{6-10}$ aryl or 5-10 membered heteroaryl, wherein $C_{1-6}$ alkyl, $C_{3-6}$ cycloalkyl, 3-6 membered cycloheteroalkyl, $C_{6-10}$ aryl and 5-10 membered heteroaryl are unsubstituted or substituted with 1 to 3 groups independently selected from $R^c$;

$R^4$ is $C_{1-3}$ alkyl, wherein $C_{1-3}$ alkyl is unsubstituted or substituted with 1 to 3 groups independently selected from $R^d$, $R^5$ is $C_{1-3}$ alkyl, wherein $C_{1-3}$ alkyl is unsubstituted or substituted with 1 to 3 groups independently selected from $R^e$, or $R^4$ and $R^5$ together with the phosphorus atom attached thereto form 5-6 membered cycloheteroalkyl or 5-8 members cycloheteroalkenyl, wherein 5-6 membered cycloheteroalkyl and 5-8 members cycloheteroalkenyl are unsubstituted or substituted with 1 to 3 groups independently selected from $R^d$, $R^6$ is H, $C_{1-3}$ alkyl, or $C_{3-6}$ cycloalkyl, wherein $C_{1-3}$ alkyl and $C_{3-6}$ cycloalkyl are unsubstituted or substituted with 1 to 3 groups independently selected from $R^f$, $R^7$ is independently H, deuterium, F, Cl, Br, —OH, amino, —CN, $C_{1-6}$ alkyl, $C_{3-6}$ cycloalkyl, —O($C_{1-6}$ alkyl), —NH($C_{1-6}$ alkyl), —N($C_{1-6}$ alkyl)$_2$, $C_{2-6}$ alkenyl or $C_{2-6}$ alkynyl, wherein $C_{1-6}$ alkyl, $C_{3-6}$ cycloalkyl, $C_{2-6}$ alkenyl and $C_{2-6}$ alkynyl are unsubstituted or substituted with 1 to 3 groups independently selected from $R^a$, $R^a$, $R^b$, $R^d$, $R^e$ and $R^f$ are independently F, Cl, Br, I, —OH, amino, methyl or methoxy; and $R^c$ is independently deuterium, F, Cl, Br, I, —OH, amino, methyl, methoxy or

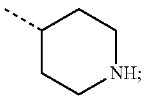

wherein each of 3-6 membered cycloheteroalkyl 5-6 membered cycloheteroalkyl, 5-8 members cycloheteroalkenyl, and 5-10 membered heteroaryl comprises 1 to 3 heteroatoms or heteroatom groups independently selected from N, NH, O, S and P(═O).

2. The compound of claim 1, or the pharmaceutically acceptable salt, ester, solvate, prodrug, isotope-labeled derivative, stereoisomer or tautomer thereof, wherein:

$R^2$ is H.

3. The compound of claim 1, or the pharmaceutically acceptable salt, ester, solvate, prodrug, isotope-labeled derivative, stereoisomer or tautomer thereof, wherein:

L is a bond, —O, or

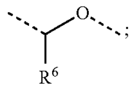

and $R^6$ is defined in claim 1.

4. The compound of claim 1, or the pharmaceutically acceptable salt, ester, solvate, prodrug, isotope-labeled derivative, stereoisomer or tautomer thereof, wherein

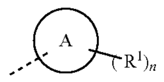

is selected from the group consisting of:

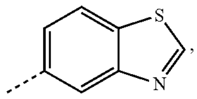,
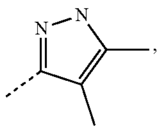,
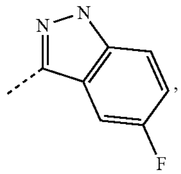,
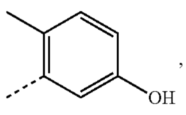,
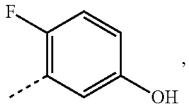,
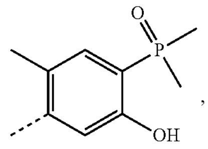, and -continued

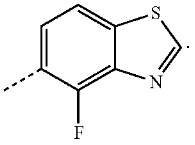

5. The compound of claim 1, or the pharmaceutically acceptable salt, ester, solvate, prodrug, isotope-labeled derivative, stereoisomer or tautomer thereof, wherein

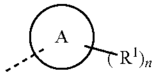

is selected from the group consisting of:

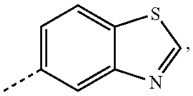, 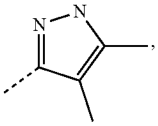, 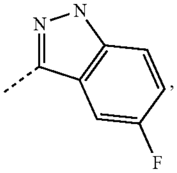, 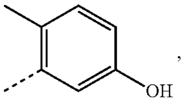, 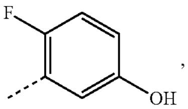, and 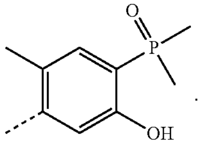.

6. The compound of claim 1, or the pharmaceutically acceptable salt, ester, solvate, prodrug, isotope-labeled derivative, stereoisomer or tautomer thereof, wherein

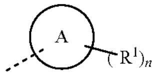

is selected from the group consisting of:

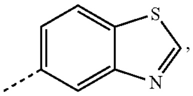, 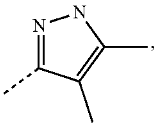, 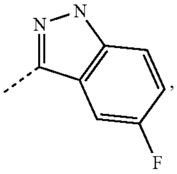, 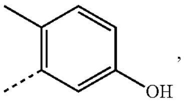,

-continued

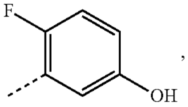, and 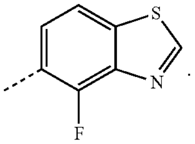.

7. The compound of claim 1, or the pharmaceutically acceptable salt, ester, solvate, prodrug, isotope-labeled derivative, stereoisomer or tautomer thereof, wherein:

$R^3$ is independently H, halide, —OH, amino, $C_{1-6}$ alkyl, $C_{3-6}$ cycloalkyl, —O($C_{1-6}$ alkyl), 3-6 membered cycloheteroalkyl, and 5-10 membered heteroaryl, wherein $C_{1-6}$ alkyl, $C_{3-6}$ cycloalkyl, 3-6 membered cycloheteroalkyl, or 5-10 membered heteroaryl are unsubstituted or substituted with 1 to 3 groups independently selected from $R^c$; and $R^c$ is defined in claim 1.

8. The compound of claim 1, or the pharmaceutically acceptable salt, ester, solvate, prodrug, isotope-labeled derivative, stereoisomer or tautomer thereof, wherein:

$R^3$ is independently H, F, methyl, ethyl, n-propyl, i-propyl, methoxy, —$OCD_3$, —$OCF_3$, —$OCHF_2$, —$OCH_2CH_2OH$, —$OCH_2CH_2OCH_3$,

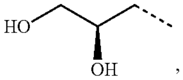, 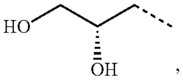, 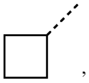, 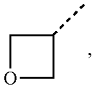, 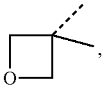, 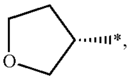, 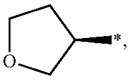, 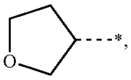, 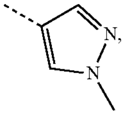, 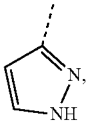, 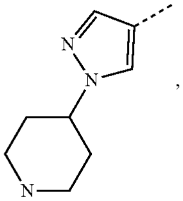, 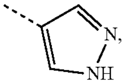, 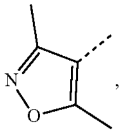, or 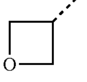, wherein * denotes a connection to L.

9. The compound of claim 1, or the pharmaceutically acceptable salt, ester, solvate, prodrug, isotope-labeled derivative, stereoisomer or tautomer thereof, wherein:

$R^3$ is independently H, methyl, ethyl, n-propyl, i-propyl, methoxy, —$OCH_2CH_2OH$, —$OCH_2CH_2OCH_3$,

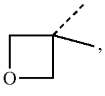, 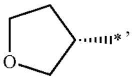, 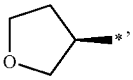, 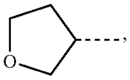, 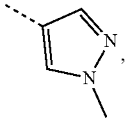, 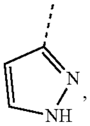, , or -continued

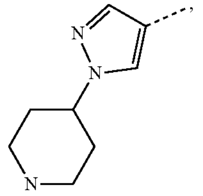

wherein * denotes a connection to L.

10. The compound of claim 1, or the pharmaceutically acceptable salt, ester, solvate, prodrug, isotope-labeled derivative, stereoisomer or tautomer thereof, wherein:

$R^3$ is independently H, F, methyl, methoxy, —$OCD_3$, —$OCF_3$, —$OCHF_2$, —$OCH_2CH_2OH$, —$OCH_2CH_2OCH_3$,

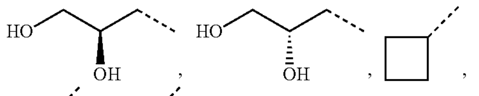

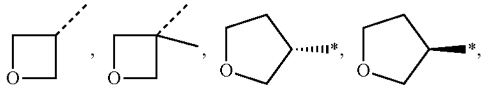

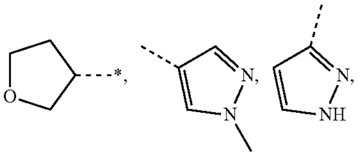

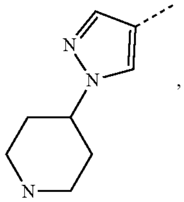

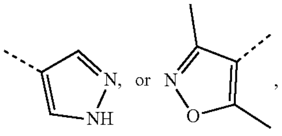

wherein * denotes a connection to L.

11. The compound of claim 1, or the pharmaceutically acceptable salt, ester, solvate, prodrug, isotope-labeled derivative, stereoisomer or tautomer thereof, wherein:

$R^3$ is independently F, methoxy, —$OCD_3$, —$OCF_3$, —$OCHF_2$, —$OCH_2CH_2OH$, —$OCH_2CH_2OCH_3$,

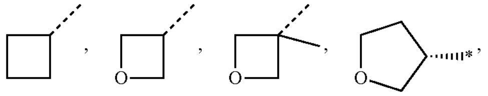

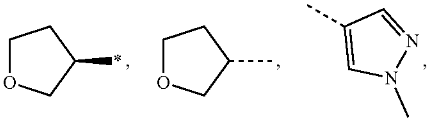

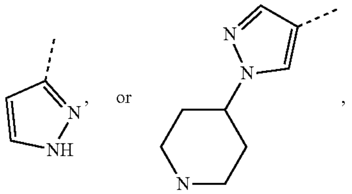

wherein * denotes a connection to L.

12. The compound of claim 1, or the pharmaceutically acceptable salt, ester, solvate, prodrug, isotope-labeled derivative, stereoisomer or tautomer thereof, wherein:

$R^3$ is independently methoxy, —$OCD_3$, —$OCF_3$, and —$OCHF_2$, wherein * denotes a connection to L.

13. The compound of claim 1, or the pharmaceutically acceptable salt, ester, solvate, prodrug, isotope-labeled derivative, stereoisomer or tautomer thereof, wherein:

$R^3$-L is independently H, F, methyl, ethyl, n-propyl, i-propyl, methoxy, —$OCD_3$, —$OCF_3$, —$OCHF_2$, —$OCH_2CH_2OH$, —$OCH_2CH_2OCH_3$,

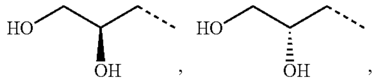

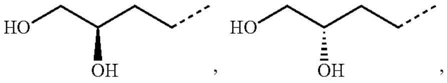

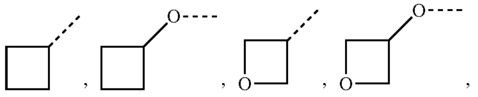

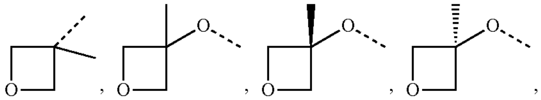

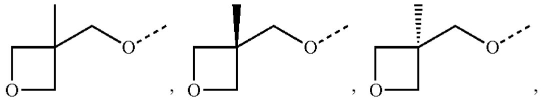

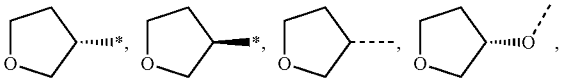

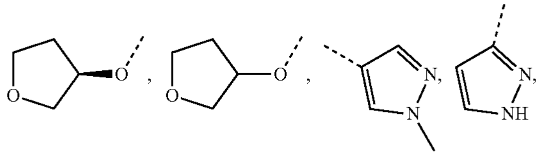

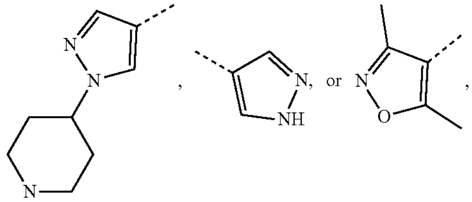

wherein * denotes a connection to quinoline.

14. The compound of claim 1, or the pharmaceutically acceptable salt, ester, solvate, prodrug, isotope-labeled derivative, stereoisomer or tautomer thereof, wherein:

$R^4$ is methyl;

$R^5$ is methyl; and $R^6$ is H or $C_{1-3}$ alkyl.

15. The compound of claim 1, or the pharmaceutically acceptable salt, ester, solvate, prodrug, isotope-labeled derivative, stereoisomer or tautomer thereof, wherein:

$R^7$ is H, deuterium, F, Cl or Br.

16. The compound of claim 1, or the pharmaceutically acceptable salt, ester, solvate, prodrug, isotope-labeled derivative, stereoisomer or tautomer thereof, wherein the compound is selected from the group consisting of:

A1
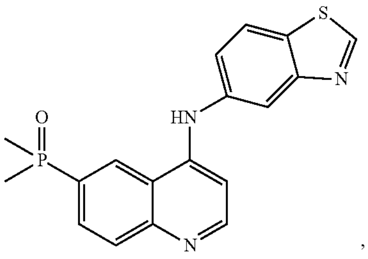
,
A2
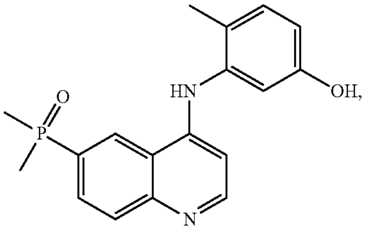
,
A3
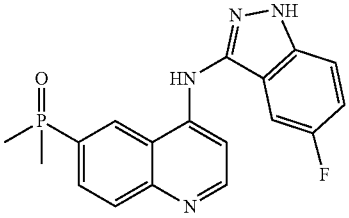
,
A4
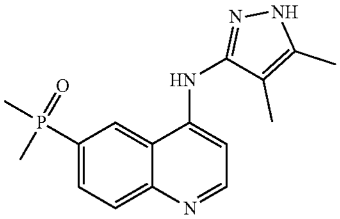
,
A5
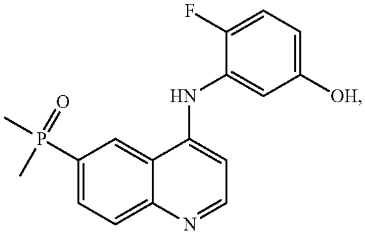
,
A6
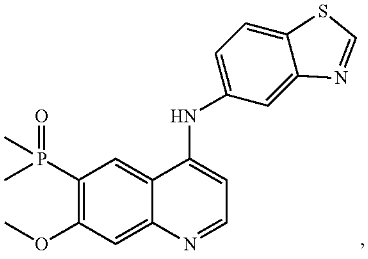
,
-continued
A7
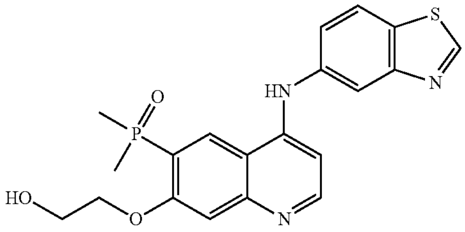
,
A8
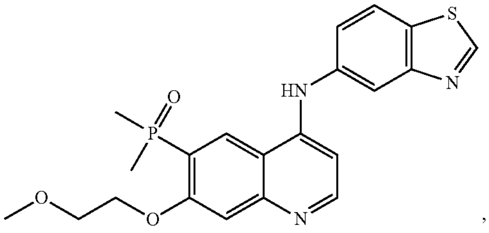
,
A9
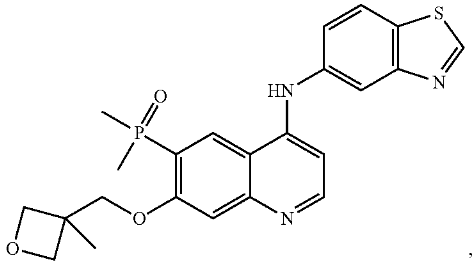
,
A10
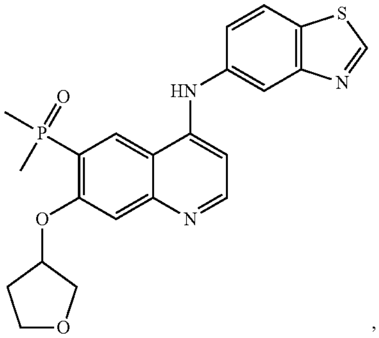
,
A11
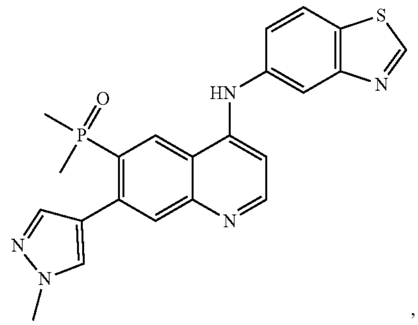
, A12
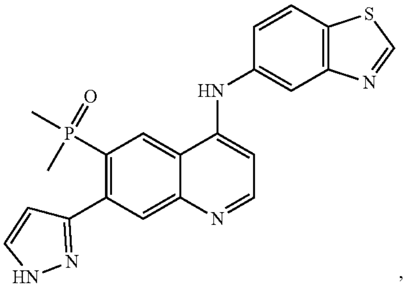
,
A13
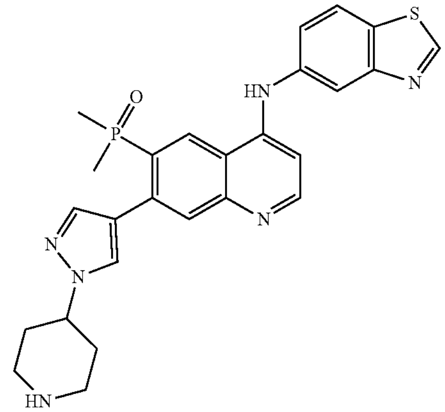
,
A14
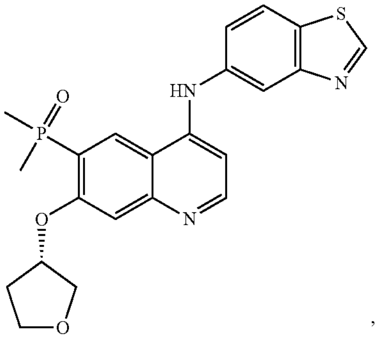
,
A15
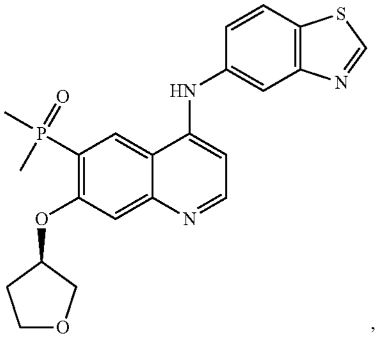
,
A16
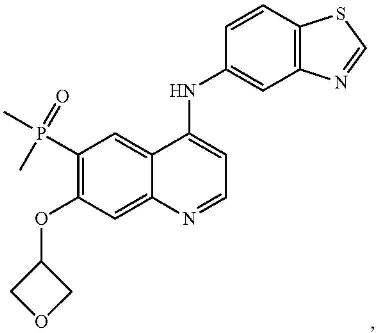
,
A17
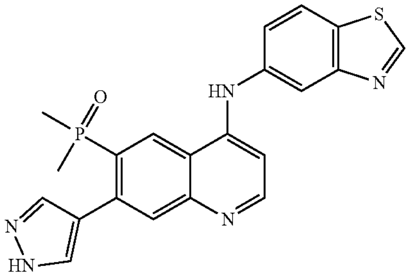
,
A18
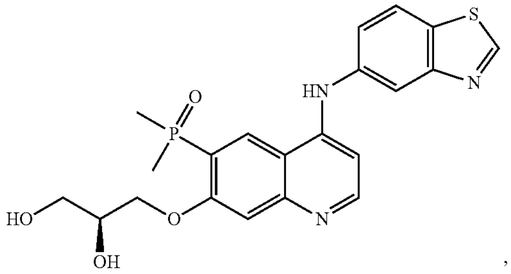
,
A19
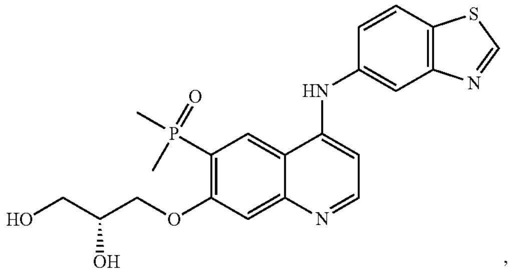
,
A20
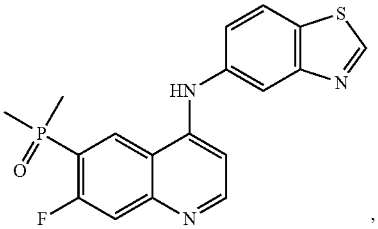
, -continued

A21

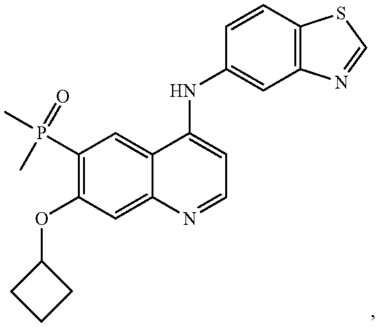

,

A22

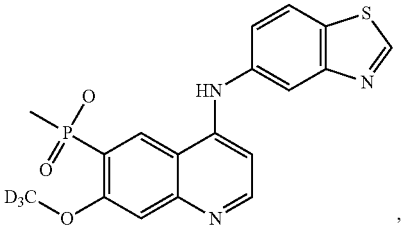

,

A23

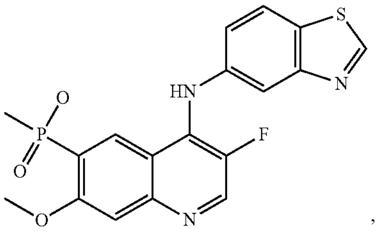

,

A24

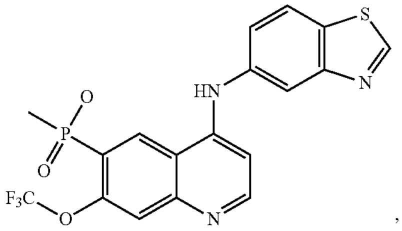

,

A25

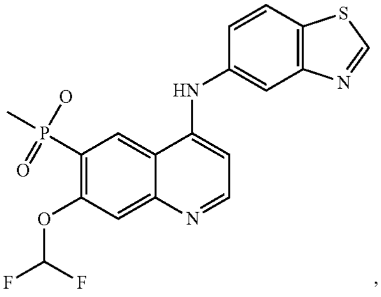

,

-continued

A26

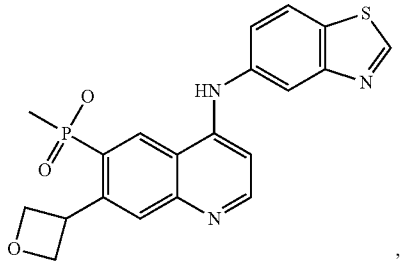

,

A27

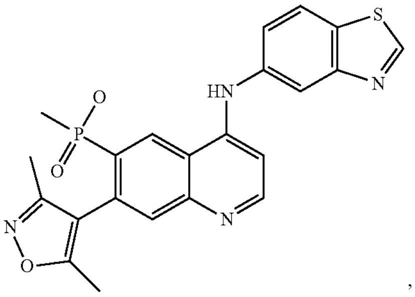

,

A28

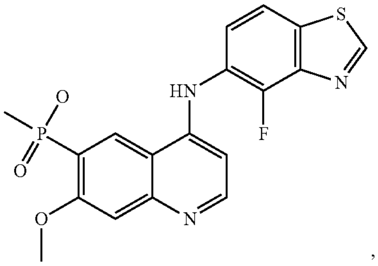

, and

A29

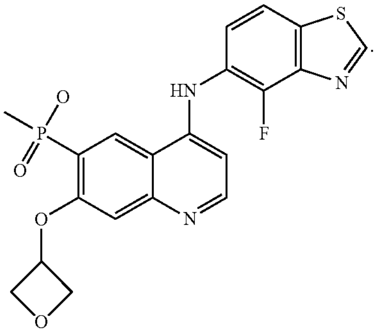

17. A pharmaceutical composition comprising a therapeutically effective amount of the compound of claim 1 or the pharmaceutically acceptable salt, ester, solvate, prodrug, isotope-labeled derivative, stereoisomer or tautomer thereof, and a pharmaceutically acceptable carrier.

18. A composition comprising:

(i) the compound of claim 1 or the pharmaceutically acceptable salt, ester, solvate, prodrug, isotope-labeled derivative, stereoisomer or tautomer thereof; and (ii) at least one additional therapeutic agent selected from the group consisting of anti-tumor agent, agent treating autoimmune disease, anti-neurodegenerative agent, agent treating metabolic disease, and agent treating genetic disease.

* * * * *